US012575968B2

(12) United States Patent
Mansour et al.

(10) Patent No.: US 12,575,968 B2
(45) Date of Patent: Mar. 17, 2026

(54) OPHTHALMIC DEVICE

(71) Applicant: New World Medical, Inc., Rancho Cucamonga, CA (US)

(72) Inventors: Khalid Mansour, Corona, CA (US); Malik Y. Kahook, Denver, CO (US); John Koontz, Chino, CA (US); Jason Mohr, Fontana, CA (US); Eric Porteous, Corona, CA (US); Dustin Tobey, San Dimas, CA (US)

(73) Assignee: NEW WORLD MEDICAL, INC., Rancho Cucamonga, CA (US)

( * ) Notice: Subject to any disclaimer, the term of this patent is extended or adjusted under 35 U.S.C. 154(b) by 561 days.

(21) Appl. No.: 18/123,433

(22) Filed: Mar. 20, 2023

(65) Prior Publication Data

US 2023/0301832 A1      Sep. 28, 2023

Related U.S. Application Data

(60) Provisional application No. 63/412,072, filed on Sep. 30, 2022, provisional application No. 63/322,904, filed on Mar. 23, 2022.

(51) Int. Cl.
| | |
|---|---|
| *A61F 9/007* | (2006.01) |
| *A61F 9/00* | (2006.01) |

(52) U.S. Cl.
CPC ............ *A61F 9/007* (2013.01); *A61F 9/0017* (2013.01)

(58) Field of Classification Search
CPC .. A61F 9/0017; A61F 9/00781; A61F 9/0008; A61F 9/00736; A61F 9/007
See application file for complete search history.

(56) References Cited

U.S. PATENT DOCUMENTS

| | | | |
|---|---|---|---|
| 5,462,527 A | * | 10/1995 | Stevens-Wright .......................... A61M 25/0147 |
| | | | 604/95.04 |
| 5,484,401 A | | 1/1996 | Rodriguez et al. |
| 6,299,131 B1 | | 10/2001 | Ryan |

(Continued)

FOREIGN PATENT DOCUMENTS

| | | |
|---|---|---|
| WO | WO-2016159999 A1 | 10/2016 |
| WO | WO-2022150684 A1 | 7/2022 |

OTHER PUBLICATIONS https://www.newworldmedical.com/product-information/ ; New Worl Medical, VIA 360 TM Surgical System animation; 7 pages, Year 2025.*

(Continued)

*Primary Examiner* — William H Rodriguez
(74) *Attorney, Agent, or Firm* — MASCHOFF BRENNAN

(57) ABSTRACT

Ophthalmic devices include a housing and a cannula extending from the housing, the cannula having a lumen for fluid flow, a reservoir for holding fluid and an activation assembly. The activation assembly includes a rotatable wheel and a moveable housing ring coupled to the wheel, the coupled rotatable wheel and moveable housing ring configured to move inward together towards an interior of the housing when an inward force is applied to the wheel and to move outward together away from the interior of the housing when an outward force is applied to the coupled wheel and the moveable housing ring. Methods of operating ophthalmic devices are also provided.

20 Claims, 49 Drawing Sheets

(56) References Cited

U.S. PATENT DOCUMENTS

| | | | | |
|---|---|---|---|---|
| 6,530,897 | B2 * | 3/2003 | Nardeo | A61M 25/0147 |
| | | | | 604/95.04 |
| 6,899,717 | B2 * | 5/2005 | Weber | A61B 17/3468 |
| | | | | 606/107 |
| 7,967,772 | B2 | 6/2011 | McKenzie et al. | |
| 8,298,196 | B1 | 10/2012 | Mansour | |
| 8,348,924 | B2 | 1/2013 | Christian et al. | |
| 9,241,832 | B2 * | 1/2016 | Schaller | A61M 25/0905 |
| 9,339,631 | B2 * | 5/2016 | Graham | A61M 25/01 |
| 9,675,369 | B2 * | 6/2017 | Teague | A61B 17/221 |
| 9,855,167 | B2 | 1/2018 | Badawi et al. | |
| 10,143,826 | B2 * | 12/2018 | Castro | A61M 25/0113 |
| 10,219,936 | B2 * | 3/2019 | Ko | A61F 9/0008 |
| 10,722,397 | B2 * | 7/2020 | Kahook | A61M 5/3134 |
| 10,729,584 | B2 * | 8/2020 | Kahook | A61M 5/3148 |
| 10,857,027 | B2 | 12/2020 | Badawi et al. | |
| 11,504,270 | B1 * | 11/2022 | Badawi | A61F 9/0008 |
| 11,540,940 | B2 * | 1/2023 | Noda | A61F 9/00781 |
| 11,654,262 | B2 * | 5/2023 | Furnish | A61M 25/0147 |
| | | | | 604/95.04 |
| D1,037,439 | S * | 7/2024 | Williams | D24/113 |
| 12,127,974 | B2 * | 10/2024 | Badawi | A61F 9/00736 |
| 2005/0101967 | A1 * | 5/2005 | Weber | A61F 9/0017 |
| | | | | 606/107 |
| 2005/0203542 | A1 * | 9/2005 | Weber | A61F 2/167 |
| | | | | 606/107 |
| 2013/0158462 | A1 * | 6/2013 | Wardle | A61F 9/0017 |
| | | | | 604/8 |
| 2013/0253438 | A1 * | 9/2013 | Badawi | A61F 9/007 |
| | | | | 604/239 |
| 2016/0074211 | A1 | 3/2016 | Ko et al. | |
| 2017/0245984 | A1 * | 8/2017 | Germann | A61M 5/31595 |
| 2020/0129334 | A1 | 4/2020 | Kahook et al. | |
| 2020/0138628 | A1 * | 5/2020 | Kahook | A61M 5/3146 |
| 2021/0177652 | A1 * | 6/2021 | Chen | A61F 9/00736 |
| 2021/0361477 | A1 | 11/2021 | Johnson et al. | |
| 2022/0096271 | A1 * | 3/2022 | Wardle | A61F 9/00781 |
| 2022/0193347 | A1 * | 6/2022 | Roth | A61M 5/31511 |
| 2022/0280339 | A1 * | 9/2022 | Badawi | A61F 9/00736 |
| 2023/0181355 | A1 * | 6/2023 | Badawi | A61M 5/002 |
| | | | | 604/294 |
| 2023/0233372 | A1 * | 7/2023 | Badawi | A61F 9/0017 |
| | | | | 606/167 |
| 2024/0074898 | A1 * | 3/2024 | Palko | A61F 9/00781 |
| 2024/0173251 | A1 * | 5/2024 | Badawi | A61K 9/0051 |
| 2024/0225894 | A1 * | 7/2024 | Needleman | A61F 9/00781 |
| 2024/0366424 | A1 * | 11/2024 | Badawi | A61M 5/002 |
| 2025/0025334 | A1 * | 1/2025 | Mathias | A61F 9/0017 |
| 2025/0057696 | A1 * | 2/2025 | Liu | A61F 9/00781 |
| 2025/0090374 | A1 * | 3/2025 | Liu | A61F 9/0017 |
| 2025/0268752 | A1 * | 8/2025 | O'Keeffe | A61F 9/00781 |
| 2025/0325401 | A1 * | 10/2025 | Needleman | A61F 9/00736 |

OTHER PUBLICATIONS

International Search Report and Written Opinion for Application No. PCT/US2023/015816, dated Jul. 25, 2023, 15 pages.

* cited by examiner 44    40    41

42

43

36

35

1302

1300

1304

1300

1306

2600
2115    2120
2154
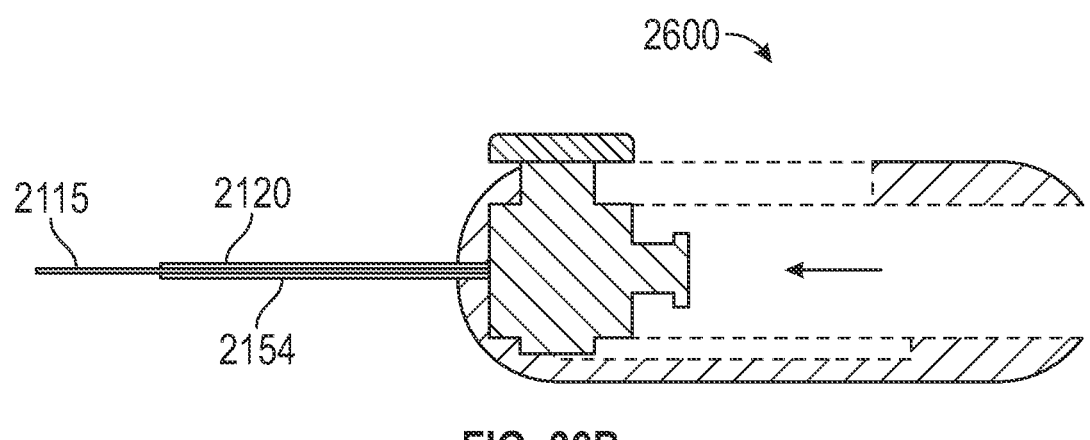
FIG. 36B
2701    2115    2700
2702
2120
2704
FIG. 37A
2701
2702
2115
2704
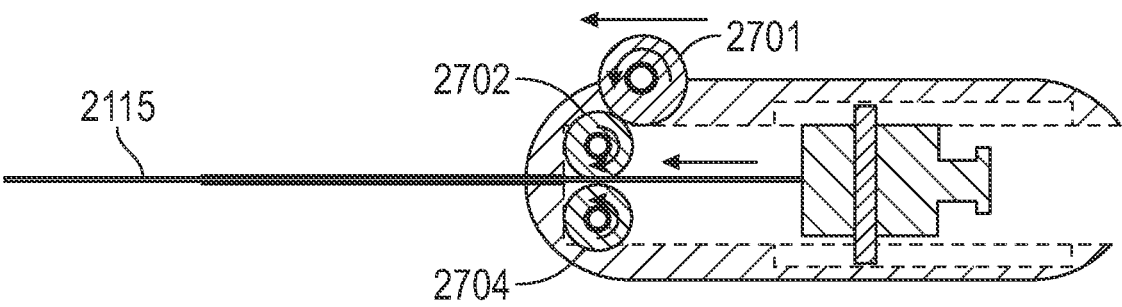
FIG. 37B

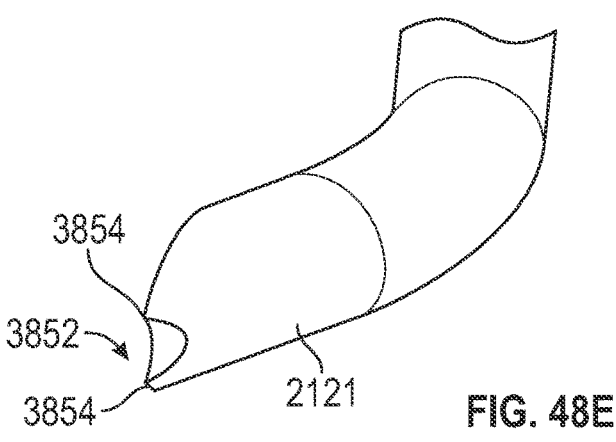
FIG. 48E
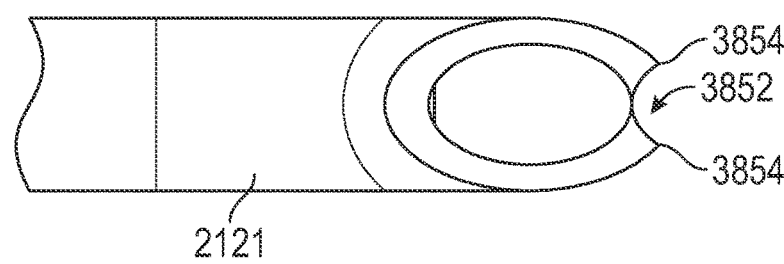
FIG. 48F
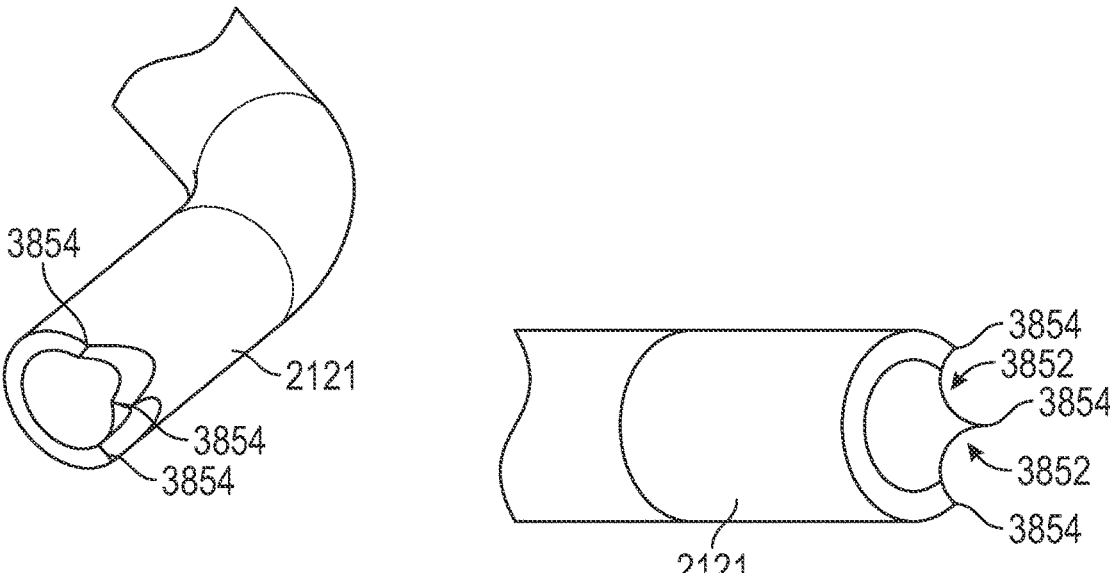
FIG. 48G
FIG. 48H

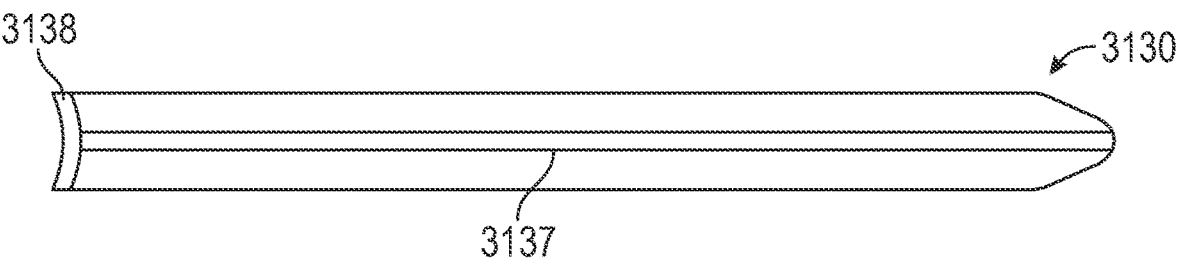
3138
3137
3130
FIG. 54
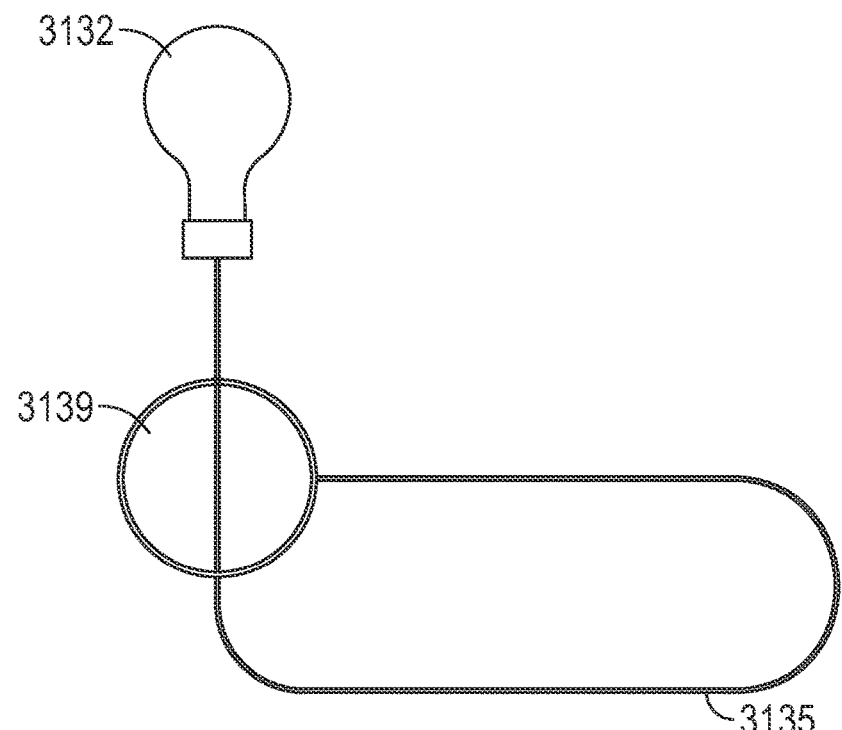
3132
3139
3135
FIG. 55
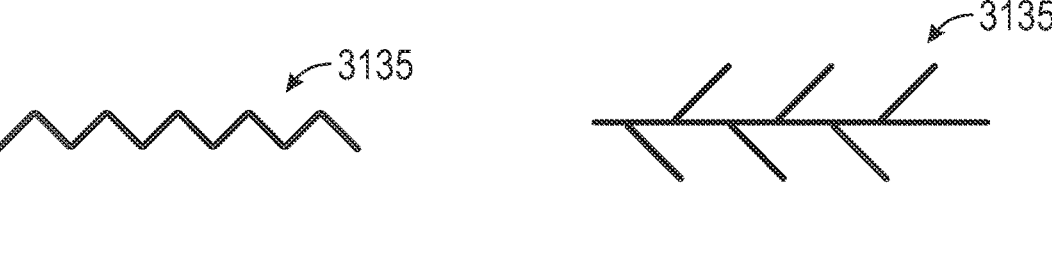
3135
3135
FIG. 56
FIG. 57

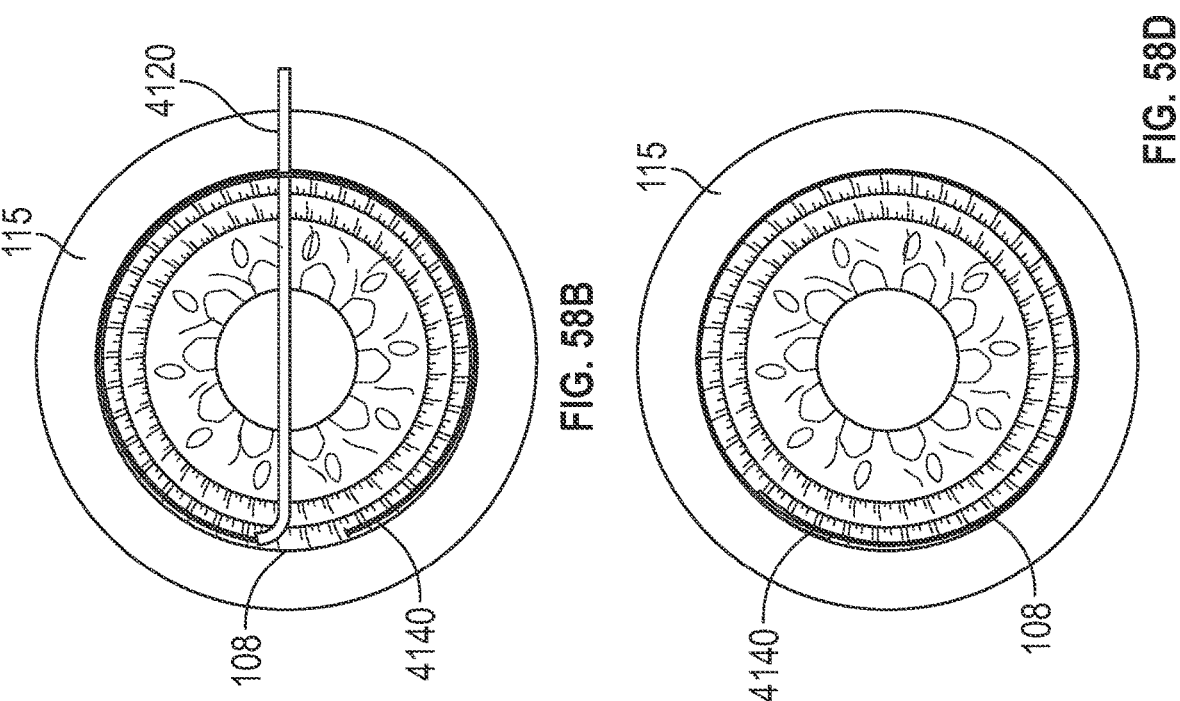
FIG. 58B
FIG. 58D
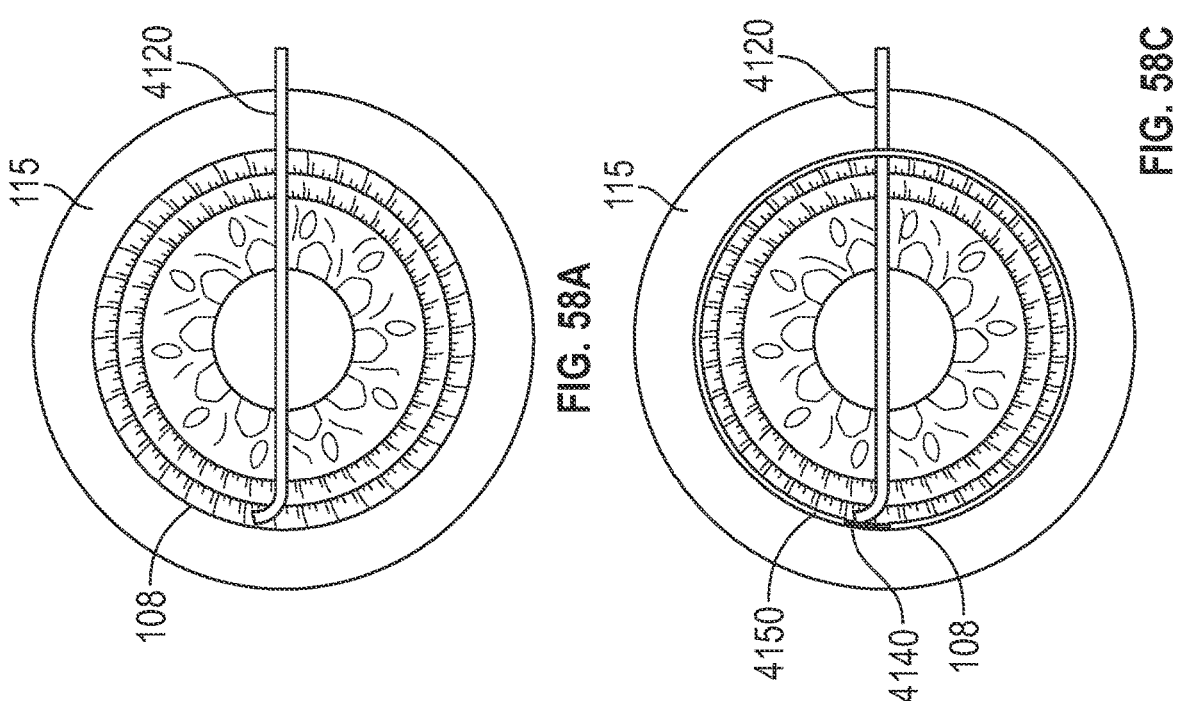
FIG. 58A
FIG. 58C

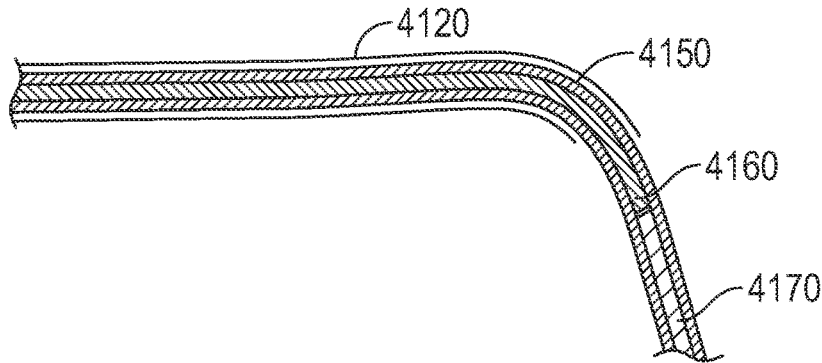
FIG. 59
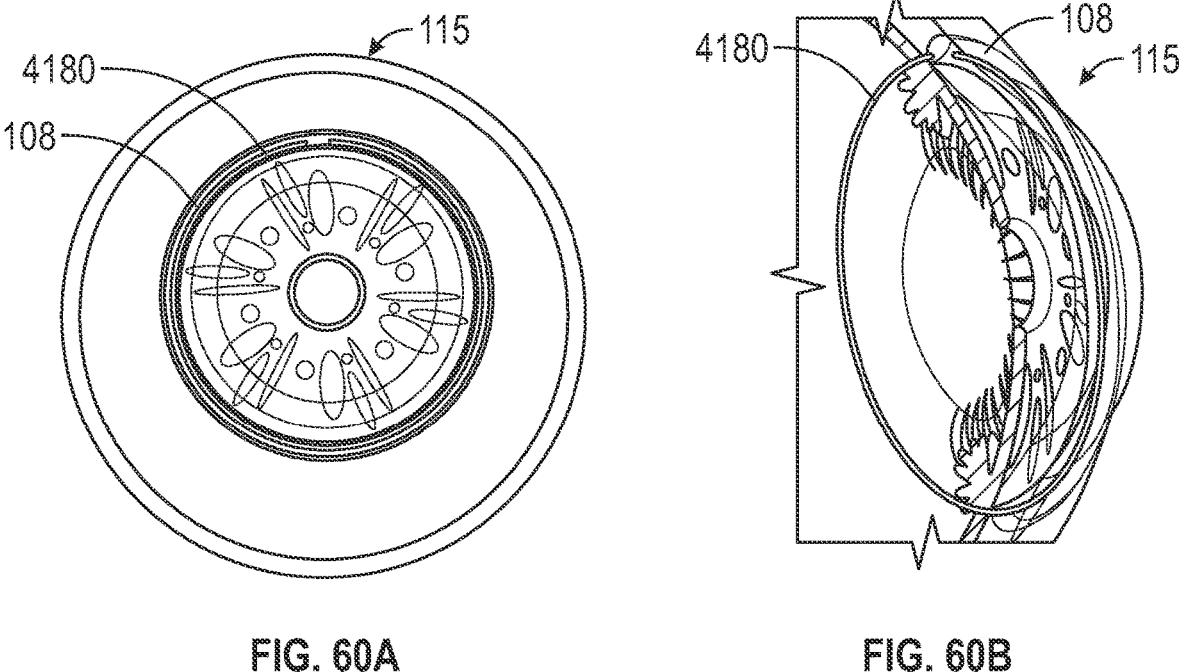
FIG. 60A                    FIG. 60B

4180b 4180a     4185

4180a     4185

4180a     4185

4180c

4180c

4180c

OPHTHALMIC DEVICE

CROSS REFERENCE TO RELATED APPLICATIONS

This application claims the benefit of priority under 35 U.S.C. § 119 to U.S. Provisional Patent Application Ser. No. 63/412,072, entitled "OPHTHALMIC DEVICE," filed on Sep. 30, 2022, and to Provisional Patent Application Ser. No. 63/322,904, entitled "OPHTHALMIC DEVICE," filed on Mar. 23, 2022, the entire contents of each which is incorporated herein by reference.

TECHNICAL FIELD

The present disclosure generally relates to an ophthalmic device, in particular an ophthalmic device for delivering viscous fluid to the eye.

BACKGROUND

In ophthalmic surgery, a high viscosity material often called a surgical viscoelastic is injected into the eye as a surgical aid. Viscoelastic materials used in ophthalmic surgery include compositions containing hyaluronic acid, chondroitin sulfate or chemically modified cellulose. Due to the unusual shear thinning or thixotropic properties of such materials, viscoelastics are injectable through a small bore needle or cannula, then recoil to a material providing stiff gel-like properties after injection. A viscoelastic is often injected into the anterior chamber of the eye during cataract surgery to maintain the intraocular space and protect the corneal endothelium from mechanical damage. The injection of viscoelastic is used to dilate tissue spaces such as Schlemm's canal during glaucoma surgery. Injection of viscoelastic is also used to dissect tissues such as the lens capsule or retinal membranes. Accordingly, it is desirable to provide an ophthalmic device to penetrate the eye and to inject viscous fluid within the eye.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

FIG. 311 depicts a top view of a system that includes the cannula adapter of FIG. 31A in combination with an additional adapter coupled to a proximal end of the standard ophthalmic viscosurgical device of FIG. 31C to facilitate controlled fluid delivery.

FIGS. 35A-38B depict various embodiments of an internal support mechanism that may be incorporated into any of the embodiments of the cannula adapters.

FIGS. 48E-48H depict various views of examples of a distal tip of a cannula of a fluid delivery device.

FIG. 54 depicts a schematic example of a catheter with a suture disposed on the outside of the catheter.

FIG. 55 depicts a schematic example of a suture bulb merged with a suture ring to form a suture loop.

FIGS. 56 and 57 depict schematic examples of suture structures.

FIGS. 58A-58D depict steps for placing a guidewire and a tension suture in an eye.

FIG. 59 depicts a push wire being deployed from a catheter.

FIGS. 60A and 60B depict front and perspective cross-sectional views of a tensioning device deployed within the canal.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The ophthalmic device of the present disclosure comprises a syringe body with a proximal end and an opposing distal end, with a hollow bore between the two ends. A plunger is disposed within the hollow bore and is coupled to a mechanism that provides positive displacement of the plunger upon actuation. The positive displacement mechanism allows high precision in delivery of viscous and in particular, viscoelastic materials from the syringe body from the distal end. By "positive displacement" it is meant that force is applied to the plunger and/or the linear translation of the plunger is incrementally restricted in such a way as to provide a constant or incrementally precise, controllable delivery of the materials from the distal end of the syringe body. The positive displacement mechanism may be configured to allow progressive linear translation of the plunger in discrete increments to control delivery. The syringe body has a fluid outlet at the distal end that may terminate in a connector such as a luer fitting for attachment of a needle or cannula.

Figure 1:
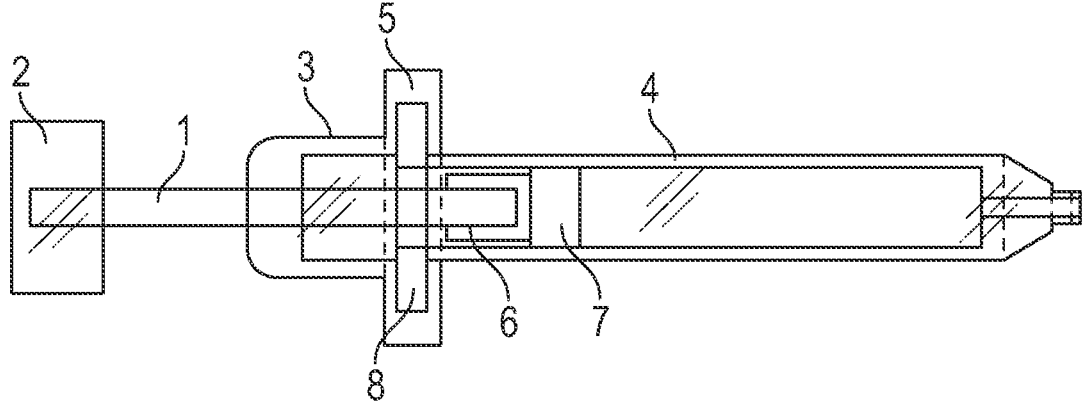
FIG. 1 depicts a cross-sectional front view of an ophthalmic device.

Referring to FIG. 1, in one embodiment of the ophthalmic device 3, a threaded rod 1 is attached at its distal end to a plunger 6. The plunger 6 is located within a syringe body 4 having a proximal flange 8. A cap 5 is connected to the flange 8. At the proximal end of the rod 1 is a handle 2 which can serve as a thumbwheel to turn the rod to advance the plunger 6. A stopper 7 is located within the syringe body 4 to form an air tight seal when force of the advancing plunger is applied against the viscous material within the syringe body. The viscous material is ejected through the distal end of the syringe body into an appropriate receiving device.

Figure 2:
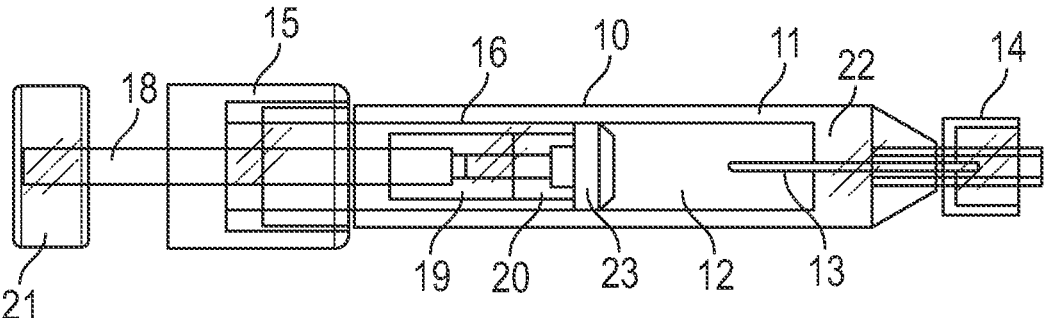
FIG. 2 depicts a cross-sectional front view of an ophthalmic device.

In another embodiment of an ophthalmic device 10, referring to FIG. 2, a cartridge 12 prefilled with viscoelastic material and comprising a rubber septum 22 at the distal end can be loaded into the syringe body 11 and then injected in a controlled manner using a screw mechanism comprising a threaded rod 18 attached to a distal plunger assembly 16 comprising a plunger 19, thrust bushing 20 and rubber stopper 23 that move slidably within the syringe body 11. The ophthalmic device 10 comprises a cap assembly 15 and the syringe body 11. The plunger 19 may have a seal such as an O ring or rubber flange (not shown) to assist in forming a fluid tight seal between the plunger 19 and the syringe body 11. The threaded rod 18 extends out through a mating threaded orifice in the cap assembly 15 at the proximal end of the syringe body 11. Turning the end of the rod 18 advances the plunger 19 to eject the viscous material loaded within a cartridge 12. The cap 15 may be removed to insert the prefilled cartridge 12 into the bore of the syringe body 11. The syringe body incorporates an internal needle 13, at the distal end of the ophthalmic device to penetrate into the cartridge. The needle provides a flow path from the cartridge to a male luer fitting 14 on the distal end of the ophthalmic device. The rubber septum 22 provides fluid tight sealing of the cartridge to the internal needle. The internal thrust bushing 20 and rubber stopper 23 at the end of the plunger assembly 16 interface to the proximal end of the cartridge 12. When the ophthalmic device handle 21 is turned, the threaded rod 18 acts upon the plunger assembly 16 to provide a positive displacement action to the cartridge to deliver the cartridge contents through the distal luer fitting 14.

The use of a positive displacement mechanism insures the precise and repeatable delivery characteristics due to the lack of a compressible component. Ophthalmic devices according to the disclosure precisely deliver small increments (microquantities) of a viscous fluid, typically in the range of 5 to 25 microliters. The subject technology is advantageous particularly because the delivery of small amounts of viscous fluids is difficult when attempting to deliver through a small bore needle, microcannula or microcatheter. The precise delivery of small amounts of a viscous fluid is especially critical in microsurgery where the fluid is used to dilate or dissect delicate tissue structures.

Figure 3:
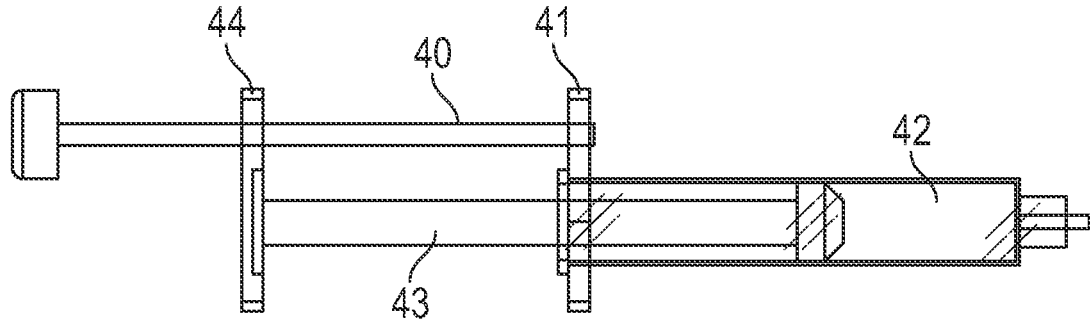
FIG. 3 depicts a cross-sectional front view of an ophthalmic device.

Referring to FIG. 3, in another embodiment, the positive displacement mechanism comprises a threaded rod 40 that attaches syringe body plate 41 to a plunger plate 44 parallel thereto. Turning of the rod 40 moves the plates 41 and 44 toward or away from each other. Attachment of the plate 41 to the syringe body 42 of the plate 44 to the plunger shaft 43, the plunger is moved to allow precision control of the delivery of material from the syringe body.

In another embodiment, the positive displacement mechanism comprises a plunger with a series of spaced mechanical stops having predetermined spacing arranged to allow linear advancement of the plunger from one mechanical stop to the next. A release mechanism or additional advancement force may be utilized to continue to advance the plunger to the next stop. The amount of plunger translation allowed by each stop may be tailored to set the precision of ophthalmic device delivery.

In another embodiment, the positive displacement mechanism is attached to a conventional syringe body, allowing it to be used with a variety of prepackaged viscoelastic syringe kits. For example, the mechanism may be attached to the syringe flange and act on or replace the provided plunger. It is thus also a feature that the ophthalmic device may be provided in kits including an ophthalmic device, one or more microcannulae for delivery of materials from the ophthalmic device to a surgical site, and/or prepackaged cartridges containing viscoelastic material useful in surgical or medical applications The ophthalmic device may be fabricated from any suitable high strength material such as metals and polymers. Preferred are materials with may be sterilized by conventional means such as by autoclaving, ethylene oxide gas treatment or exposure to ionizing radiation. Suitable materials include metals such as steel and titanium, polymers such as polysulfone, polyethylene, nylon, polymethylmethacrylate, polyethylene terephthalate, polypropylene and polycarbonate.

Figure 4:
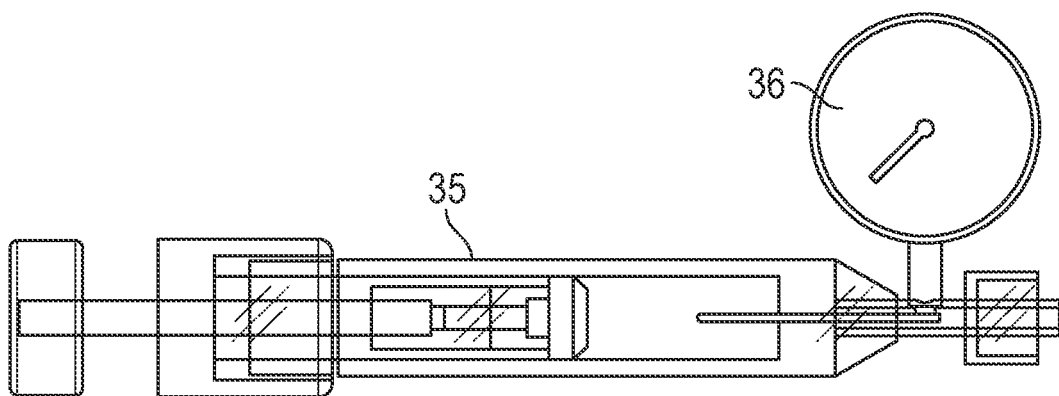
FIG. 4 depicts a cross-sectional front view of an ophthalmic device with a pressure gauge.
Figure 5:
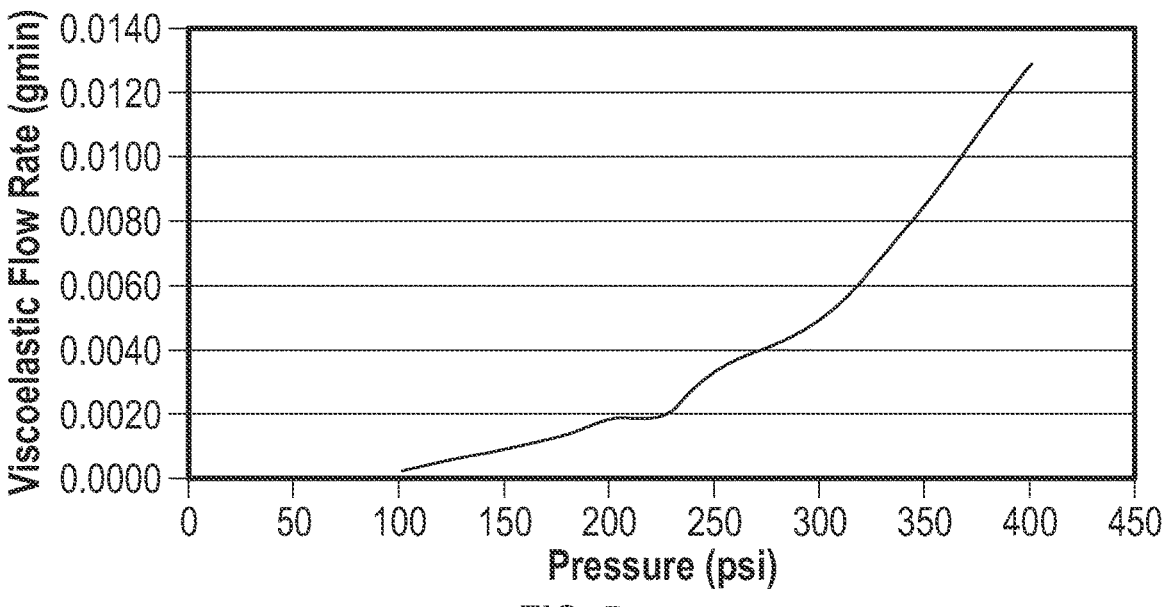
FIG. 5 depicts graph of pressure v. flow rate of delivery of viscoelastic material from an ophthalmic device.

The ophthalmic device may also be used for rate-controlled delivery to precisely deliver viscous fluids at a slow and predetermined flow rate by maintaining a predetermined varied or constant injection pressure. When injecting through a small bore device such as a microcannula or a microcatheter with controlled injection pressure, a constant or predetermined profiled flow rate of viscous fluid results. Regulation of injection pressure measured at the ophthalmic device output or within the ophthalmic device allows control of the flow rate. Referring to FIG. 4, pressure regulation may be accomplished by attaching a pressure gauge 36 or trans-ducer to an ophthalmic device 35. A constant injection pressure may be maintained by manual control of the positive displacement mechanism while monitoring injec-tion pressure or alternatively by electrical feedback to a powered actuator driving the injection mechanism. In an alternate embodiment, pressure regulation may also be accomplished by mechanical means by limiting applied force by the positive displacement mechanism. For example, a clutch mechanism may be integrated into a screw drive mechanism to limit the maximum force applied to delivery the viscous material.

The ophthalmic device may also incorporate a pressure relief valve into the ophthalmic device to prevent over pressurization or pressure spike during viscous fluid deliv-ery. The pressure relief valve may consist of a ball and spring assembly, where the ball is pressed across an orifice by spring force until the injection pressure overcomes the spring force to allow fluid flow and pressure release. The relief valve may be designed to allow user adjustment of the maximum injection pressure.

Figure 6:
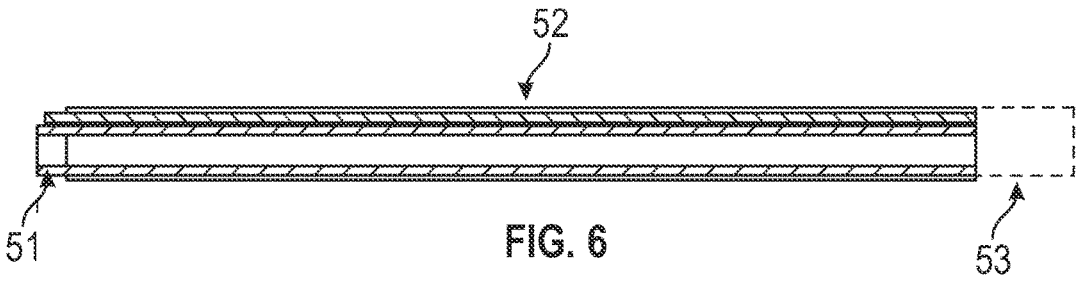
FIG. 6 depicts a cross-sectional front view of a composite microcannula having a tapered reinforcing element.

The disclosure comprises a microcannula designed to be advanced into very small tissue spaces during surgery. In particular for ophthalmic surgery, the microcannula may be used to cannulate Schlemm's Canal, aqueous humor collec-tor channels, aqueous veins, retinal veins and the suprachor-oidal space. Such structures range from 50 to 250 microns in diameter, thereby restricting the outer diameter of the microcannula to similar dimensions. The microcannula comprises a flexible elongated element with a connector at the proximal end 53, a distal tip, and a communicating channel 51 therebetween, as seen in FIG. 6. The communi-cating channel 51 of the microcannula may be used to deliver fluids, materials, energy, gases, suction, surgical tools and implants to a distal surgical site for a variety of surgical tasks. The communicating channel 51 may be the lumen of a tube-like elongated element to transport materi-als, an optical fiber to transport light energy, or a wire to transport electrical signals. The flexible elongated element with a communicating channel 51 is referred to as the communicating element. A single communicating element may have more than one communicating channel.

The microcannula of the present disclosure incorporates specific design features that enable it to be placed into very small tissue spaces. A key feature is the use of a composite microcannula design that has the appropriate combination of axial stiffness and compliance. The microcannula is desired to be flexible to allow it to be advanced along a curved or tortuous tissue space with minimal tissue trauma, but with sufficient axial stiffness or "pushability" to allow transfer of force to advance the microcannula. For a fixed outer dimen-sion, the mechanical properties of the microcannula may be tailored by the selection of materials of construction and cross-sectional dimensions. In one embodiment, a reinforc-ing element 52 is attached to the outside of a communicating element. Typically, the reinforcing element 52 comprises a material with higher flexural modulus than the communi-cating element. The communicating element may be a thin wall polymer or metallic tube. The reinforcing element 52 may be formed of any high modulus material such as, but not limited to, metals including stainless steel and nickel tita-nium alloys, ceramic fibers and high modulus polymers, filled or reinforced polymers, and polymer-polymer com-posites.

For optimal use in small tissue spaces, the microcannula is desired to be flexible at the distal tip, but transitioning to more rigid mechanical properties toward the proximal end.

Figure 7:
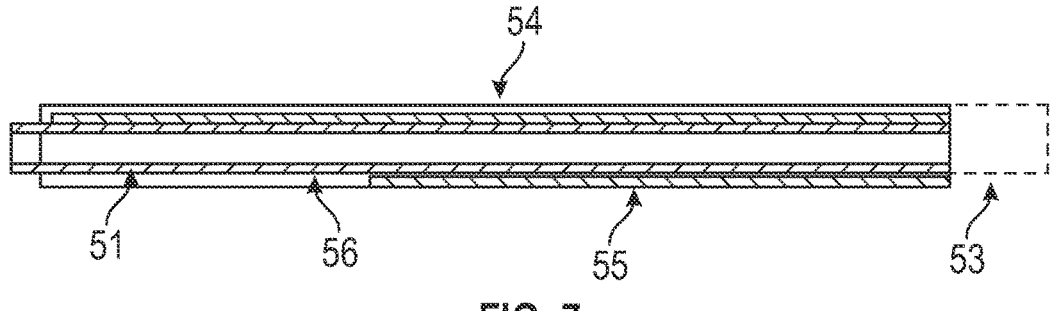
FIG. 7 depicts a cross-sectional front view of a composite microcannula having two reinforcing elements, one full length and one partial length.

The transition may comprise one or more steps in mechani-cal compliance, or a gradient of compliance along the length of the microcannula. The transition in mechanical properties may be accomplished by a change in the cross-sectional area or material properties of the microcannula along its length, the incorporation of one or more stiffening members, or a combination thereof. In one embodiment of the disclosure, the microcannula incorporates a communicating element 51 forming the communicating channel 51 fabricated from a flexible polymer with two reinforcing members 54, 55 attached along the length, as seen in FIG. 7. One of the reinforcing members 55 extends along the communicating element but not completely to the distal tip, while the other reinforcing member 54 extends completely to the distal tip to provide a transition in flexural compliance. The reinforc-ing members 54, 55 may be formed of a high modulus polymer or metal. In a similar embodiment, a single rein-forcing member with a transition in flexural stiffness, such as a tapered wire 52, may be used to reinforce the commu-nicating element. Alternatively, a reinforcing member may be formed of sequential segments of varying modulus or cross-sectional dimensions. The reinforcing elements may be held in place by an outer sheath 56 which may comprise a tight fitting polymer tube or polymer shrink tubing. Alter-natively, the reinforcing elements may be adhered or bonded to the communicating element, or may be fully or partially contained within the communicating element.

The reinforcing element may also provide kink resistance to the communicating element. This is especially advanta-geous for use with communicating elements fabricated from high modulus polymers, such as polyimide, polysulfone, ultra-high molecular weight polyethylene and fiber rein-forced polymer composites, which kink or deform under high loads, forming a permanent mechanical defect. The reinforcing element may also comprise a malleable material to allow the shape of the microcannula to be adjusted manually to better accommodate a curved shape of the tissue space. Possible malleable materials for the reinforcing ele-ment include but are not limited to steel, silver and platinum alloys.

Figure 8:
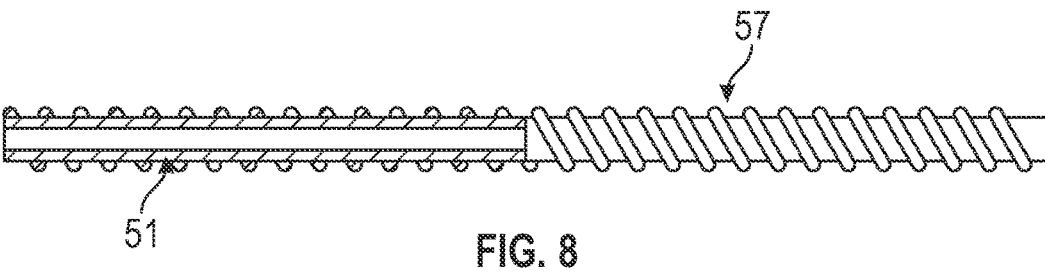
FIG. 8 depicts a partial cross-sectional front view of a composite microcannula having a spiral wound reinforcing element in the form of a round wire.
Figure 9:
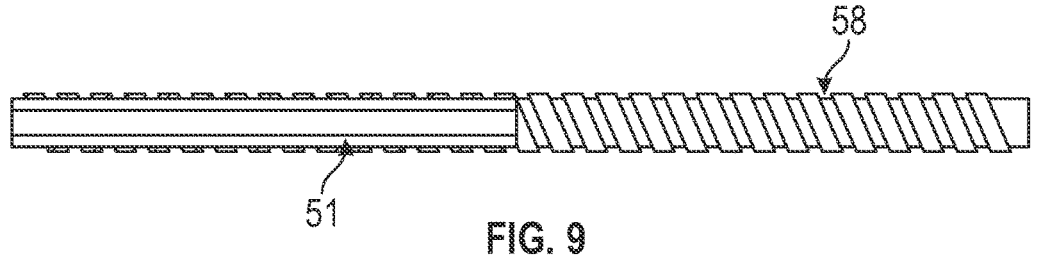
FIG. 9 depicts a partial cross-sectional front view of a composite microcannula having a spiral wound reinforcing element in the form of a flat ribbon.

The reinforcement of the communicating element may also be accomplished by the incorporation of coil-like members to provide high flexural compliance but also high axial stiffness for pushability, as seen in FIGS. 8 & 9. A reinforcing member 57, 58 attached to an outer sheath may be a coiled or wound element on or formed into the exterior surface of the sheath. The reinforcing member 57, 58 may be any suitable high modulus material including metals such as, but not limited to, stainless steel, titanium and superelastic alloys, ceramics such as ceramic fibers, and high modulus polymers or composite polymer structures such as carbon fiber reinforced epoxy. The members may have any suitable cross-section such as round or semi-circular or rectangular, as in the case of a flat wire winding. The winding pitch of the reinforcing members may be constant, or it may be varied to achieve differential flexural properties along the length of the microcannula. Multiple wound elements may be incorporated, with the elements being formed of like or different materials. The reinforcing element or multiple reinforcing elements may also be configured to provide a preferred deflection orientation of the microcannula.

The composite microcannula of the present disclosure may also include multiple communicating elements. In one embodiment, the microcannula may include two or more elongated communicating elements with a reinforcing mem-ber to form a composite structure. The components may be adhered together, placed within an outer sheath, such as heat shrink tubing or an outer communicating element may contain one or more other communicating elements. One of the communicating elements may be used for transport of materials, another for transport of light or energy, thus providing a multifunctional surgical tool. The communicating elements may be aligned side-by-side or arranged around one or more reinforcing elements. In one embodiment, one communicating element with an annular cross-section forming a lumen may be fitted with a second communicating element within the lumen. Such concentric alignment of communicating elements may also be used in combination with other communicating elements that are not in concentric alignment.

In one particular embodiment, the composite microcannula may be used only to transfer mechanical energy. For example, the microcannula may be used to advance into a tissue space and used to snare a foreign object or area of tissue. In such cases, the elongated communicating element may be a material such as a wire, polymer, or fiber composite of appropriate mechanical properties. An inner member, which fits and slides within the communicating element, may also be incorporated, the inner member having at least a proximal end and a distal tip. Advancement or withdrawal of the inner member may be used to change the shape of the distal tip of the microcannula, or alternatively to effect a mechanical action at the distal tip.

In one embodiment, the microcannula also comprises a proximal connecter for the communicating element. The connector may serve to connect a supply of material or energy, such as an infusion syringe or light source to the communicating channel 51 of the communicating element. Additionally, the microcannula may contain a central section comprising a single or multiple side connectors to allow the attachment of ancillary equipment such as syringes, vacuum or pressure sources, sensing means and the like. The attachment connectors may use standard designs such as Luer fittings or may be designed to only accept connection with specific components. In another embodiment, the composite microcannula may incorporate fenestrations or windows along the length. The fenestrations may be used to deliver materials from the sides of the microcannula, for instance the delivery of therapeutic agents to the tissues of Schlemm's Canal. Alternately, with the connection of a vacuum generating device to the proximal connector of the communicating element, the fenestrations may be used to provide suction against soft tissues. The suction may be used for the removal of tissue or may be used to anchor the microcannula in place while another element is advanced through the microcannula. For example, a composite suction microcannula may be used to strip the juxtacanicular tissues from the inner wall of Schlemm's Canal.

The communicating element may be formed of a thin walled polymer or metallic tube of sufficient stiffness to allow it to be advanced into tissues or along a tissue space such as Schlemm's Canal, and of sufficient flexibility to follow the circular tract of Schlemm's Canal. Due to the small size of the target tissue spaces, the microcannula must be appropriately sized. Typically, the microcannula is sized in the range of 50 to 350 microns outer diameter with a wall thickness from 10-100 microns. The cross-section of the microcannula may be round or oval or other bound shape to approximate the shape of a tissue space such as Schlemm's Canal. In some embodiments, a predetermined curvature may be applied to the device during fabrication.

Suitable materials for the communicating element include metals, polyetheretherketone (PEEK), polyethylene, polypropylene, polyimide, polyamide, polysulfone, polyether block amide (PEBAX), fluoropolymers or similar materials. The outer sheath may also have surface treatments such as lubricious coatings to assist in tissue penetration and ultrasound or light interactive coatings to aid in location and guidance. The microcannula may also have markings on the exterior for assessment of depth in the tissue space. For example, the markings may take the form of rings around the outer shaft located at regular intervals along the length of the microcannula. The external markings allow user assessment of the length of the tissue space or channel accessed by the microcannula, and the approximate location of the microcannula tip.

Figure 10:
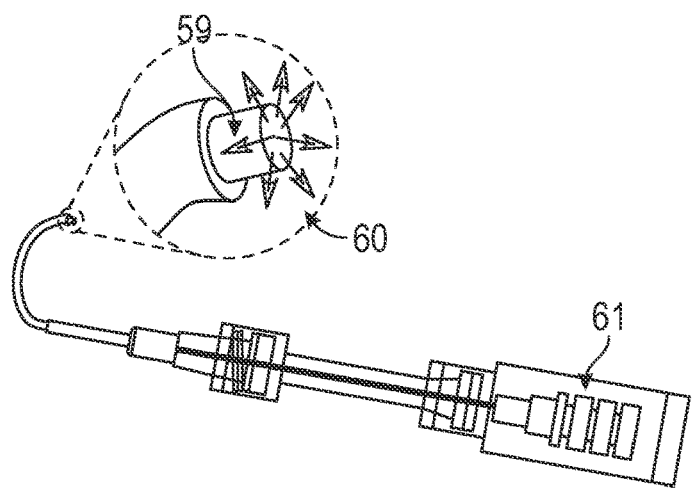
FIG. 10 depicts a perspective view and close up view of a curved composite microcannula having a signaling beacon tip extending beyond the distal tip of outer sheath.

In an embodiment of the disclosure, a first communicating element used for initial placement of the microcannula has a signaling beacon to identify the location of the microcannula distal tip relative to the target tissues, as seen in FIG. 10. The signaling means may comprise an echogenic material for ultrasound guidance, an optically active material for optical guidance or a light source for visual guidance placed at the microcannula tip or placed to indicate the position of the microcannula tip. In one embodiment, a plastic optical fiber (POF) 59 is used as a communicating element to provide a bright visual light source at the distal tip 60. The distal tip 60 of the POF 59 is positioned proximal to, near or slightly beyond the distal end of the microcannula sheath and the emitted signal may be detected through tissues visually or using sensing means such as infrared imaging. The POF 59 may also have a tip that is beveled, mirrored or otherwise configured to provide for a directional beacon. The beacon may be illuminated by a laser, laser diode, light-emitting diode, or an incandescent source such as a mercury halogen lamp. In an alternate embodiment, the signaling means may comprise visualization aids along the length of the microcannula, for example a side emitting optical fiber of discrete length leading up to the distal end or at a known point along the microcannula may be used to indicate the position of the microcannula and the distal tip. Upon placement of the microcannula at the target tissues, the beacon assembly 61 and POF 59 may be removed. The connection point may be sealed with a cap or with a self-sealing mechanism such as a one-way valve or an elastomer seal. Alternatively, the POF may be placed co-linear to or within the lumen of a delivery communicating channel, allowing for delivery of fluids or gases through the delivery communicating channel without requiring removal of the beacon assembly.

Alternate embodiments of the microcannula may use other imaging technologies to locate the signal beacon. Other possible imaging technologies include but are not limited to magnetic resonance imaging, fluoroscopy and ultrasound. In these embodiments, the beacon signal may take other forms to match the imaging technology such as a radiopaque marker attached to or embedded at or near the distal tip of the microcannula. Alternatively, or in addition, an echogenic material or coating may be added to the distal tip, etc.

Figure 11:
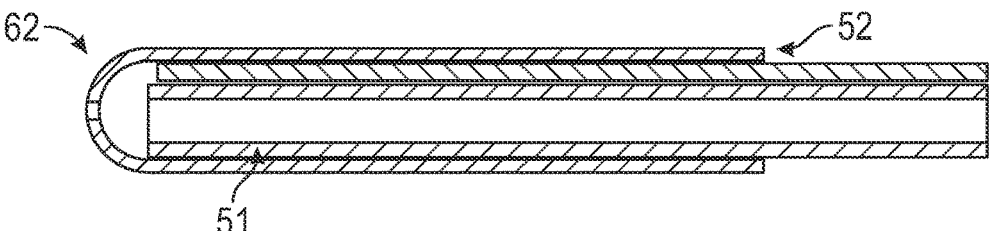
FIG. 11 depicts a cross-sectional front view of a composite microcannula having a tapered reinforcing element and a rounded distal tip.
Figure 12:
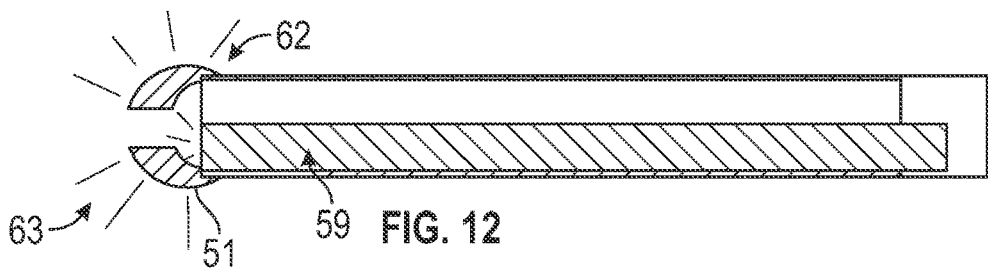
FIG. 12 depicts a cross-sectional front view of a composite microcannula having a ball-end distal tip formed separately from the communicating element and an optical fiber to provide for a beacon with light dispersed at the tip.

It is also preferred for the microcannula to have a rounded distal tip 62 to minimize tissue trauma and aid the ability of the microcannula to be advanced into small tissue spaces, as seen in FIGS. 11 and 12. The rounded tip 62 may be the same outer diameter as the microcannula or larger, depending on the specific properties desired. The rounded tip 62 may be formed and attached to the microcannula during assembly or alternatively, the microcannula tip may be processed by a secondary operation to form a rounded contour. When the rounded tip 62 is used in conjunction with a light emitting signaling beacon 59 such that the light is delivered proximal to the rounded tip, the tip acts to disperse the light 63. The dispersed light aids visualization when viewing the microcannula off axis, for example when advancing the microcannula in Schlemm's Canal.

Another key feature of the disclosure is the use of a communicating element to deliver fluid to the distal tip during advancement of the microcannula within the tissue space. The injection of small amounts of fluid may serve to open the tissue space ahead of the microcannula tip and lubricate the channel to greatly increase the ability to advance the microcannula atraumatically. Delivery of surgical viscoelastic materials such as hyaluronic acid solutions and gels are especially efficacious in aiding advancement and placement of the microcannula. Delivery of fluids, especially gel-like viscoelastic materials, allows for the dilation of the tissue space in the circumstance that a constriction or partial blockage is reached during advancement of the microcannula. A particularly effective embodiment comprises a microcannula with a communicating element such as an optical fiber to provide a signaling beacon at the microcannula tip and a second communicating element to deliver a fluid such as a solution of hyaluronic acid to the microcannula tip while the signaling beacon is active. Such a microcannula may be manually manipulated and used to deliver fluids to aid microcannula advancement while simultaneously observing the microcannula tip location along the tissue space. The combination of fluid delivery in the path of the microcannula and the observation of the microcannula tip when advanced, retracted and torsioned allows precisely controlled manipulation and advancement in tight tissue spaces. The ease of manipulation is further aided with the addition of a reinforcing member to the communicating element of the microcannula.

Described here are systems and methods for accessing Schlemm's canal and for delivering an ocular device and/or fluid composition therein to reduce intraocular pressure and thereby treat conditions of the eye. The fluids and certain components of the system, e.g., the slidable conduit, may be used to provide a force for disrupting trabeculocanalicular tissues, which include the trabecular meshwork, juxtacanalicular tissue, Schlemm's canal, and the collector channels. As used herein, the term "disrupting" refers to the delivery of a volume of fluid or a system component that alters the fluid in a manner that improves flow through the trabeculocanalicular outflow pathway. Examples of tissue disruption include, but are not limited to, dilation of Schlemm's canal, dilation of collector channels, increasing the porosity of the trabecular meshwork, stretching the trabecular meshwork, forming microtears in juxtacanalicular tissue, removing septae from Schlemm's canal, cutting or removal of trabeculocanalicular tissues, or a combination thereof.

Figure 13:
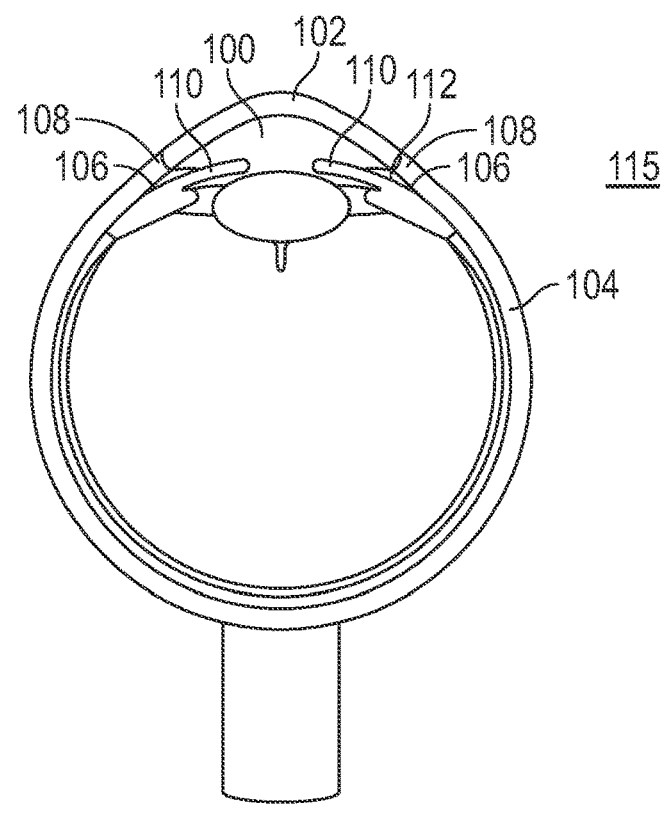
FIG. 13 depicts a stylized, cross-sectional view of the eye and some of the structures involved in the flow of aqueous humor out of the eye.

To better understand the systems and methods described here, it may be useful to explain some of the basic eye anatomy. FIG. 13 is a stylized depiction of a normal human eye 115. The anterior chamber 100 is shown as bounded on its anterior surface by the cornea 102. The cornea 102 is connected on its periphery to the sclera 104, which is a tough fibrous tissue forming the white shell of the eye 115. Trabecular meshwork 106 is located on the outer periphery of the anterior chamber 100. The trabecular meshwork 106 extends 360 degrees circumferentially around the anterior chamber 100. Located on the outer peripheral surface of the trabecular meshwork 106 is Schlemm's canal 108. Schlemm's canal 108 extends 360 degrees circumferentially around the meshwork 106. At the apex formed between the iris 110, meshwork 106, and sclera 104, is angle 112.

The systems are generally configured for single-handed manipulation and for control by a single operator, and include one or more features useful for easily accessing Schlemm's canal with minimal trauma. Once access to the canal has been obtained, the system may deliver an ocular device, a fluid composition, or both. In some variations, the system advances a tool that disrupts Schlemm's canal and surrounding tissues without delivery of an ocular device or a fluid composition. For example, the tool may be a conduit, slidable within, and extendable from, the cannula used to access the canal, having an outer diameter sized to disrupt the canal and surrounding tissues. The distal end of the conduit may also be provided with a disruptive component to aid in the disruption of trabeculocanalicular tissues.

The device that is implanted into the canal will generally be configured to maintain the patency of Schlemm's canal without substantially interfering with transmural fluid flow across the canal. Ocular implants may be delivered. In some variations, the implants include a support having a least one fenestration that completely traverses a central core of Schlemm's canal without substantially interfering with transmural fluid flow or longitudinal fluid flow across or along the canal. The ocular device may also disrupt the juxtacanalicular trabecular meshwork or adjacent inner wall of Schlemm's canal. The ocular devices may also be coated with a drug useful for treating ocular hypertension, glaucoma, or pre-glaucoma, infection, or scarring or inflammation postoperatively. The ocular device may also be formed to be solid, semi-solid, or bioabsorbable.

The systems may also be used to deliver a fluid composition, e.g., saline or a viscoelastic fluid. The saline may be used for irrigation. The viscoelastic fluid may be employed in ab-interno versions of viscocanalostomy or canaloplasty procedures to disrupt the canal and surrounding tissues.

The systems described herein may be single-handed, single-operator controlled devices that generally include a universal handle having a grip portion and a housing that has an interior and a distal end. A cannula is typically coupled to and extends from the housing distal end. The cannula may include a proximal end and a distal curved portion, where the distal curved portion has a proximal end and a distal end, and a radius of curvature defined between the ends. The cannula may also be configured to include a body; a distal tip having a bevel; and a lumen extending from the proximal end through the distal tip. The bevel may directly engage the distal end of the curved portion of the cannula (i.e., the bevel may directly engage the radius of curvature). The systems may also generally include a drive assembly partially contained within the housing comprising gears that translate rotational movement to linear movement. When an ocular device is to be implanted into Schlemm's canal, the systems may further include a slidable positioning element having a proximal end and a distal end that is coaxially disposed within the cannula lumen. The system may also be configured to include a fluid assembly in the handle and a slidable conduit coaxially disposed within the cannula lumen when a fluid composition is to be delivered into Schlemm's canal. Fluid compositions such as saline, viscoelastic fluids, including viscoelastic solutions, air, and gas may be delivered using the system. Suitable markings, colorings, or indicators may be included on any portion of the system to help identify the location or position of the distal end of the cannula, the positioning element, the engagement mechanism, the ocular device, or the slidable conduit.

The ocular delivery systems described herein may include a universal handle capable of single-handed use. For example, the handle may be configured to be capable for use with the right hand in one orientation, and then with a simple flip of the handle (or by rotating the cannula itself 180 degrees) to a second orientation, use with the left hand. The handle generally includes a grip portion and a housing. The grip portion may be raised, depressed, or grooved in certain areas, or textured to improve hold of the handle by the user or to improve comfort of the user. The housing may include an interior portion and a distal end. The interior portion of the housing may contain a drive assembly and a positioning element (both further described below). In some variations, the distal end of the housing includes a fluid port that can provide fluids for irrigation of the operative field or to purge air from the system.

The universal handle may be made from any suitable material, including without limitation, fluoropolymers; thermoplastics such as polyetheretherketone, polyethylene, polyethylene terephthalate, polyurethane, nylon, and the like; and silicone. In some variations, the housing or portions thereof may be made from transparent materials. Materials with suitable transparency are typically polymers such as acrylic copolymers, acrylonitrile butadiene styrene (ABS), polycarbonate, polystyrene, polyvinyl chloride (PVC), polyethylene terephthalate glycol (PETG), and styrene acrylonitrile (SAN). Acrylic copolymers that may be particular useful include, but are not limited to, polymethyl methacrylate (PMMA) copolymer and styrene methyl methacrylate (SMMA) copolymer (e.g., Zylar 631® acrylic copolymer).

The length of the universal handle may generally be between about 4 inches (10.2 cm) and 10 inches (25.4 cm). In some variations, the length of the universal handle is about 7 inches (17.8 cm).

The cannula of the ocular delivery system is typically coupled to and extends from the housing distal end, and is generally configured to provide easy and minimally traumatic access to Schlemm's canal using a minimally invasive ab-interno approach. Some variations of the cannula may include a proximal end and a distal curved portion, where the distal curved portion has a proximal end and a distal end, and a radius of curvature defined between the ends. The cannula may also be configured to include a body; a distal tip having a bevel; and a lumen extending from the proximal end through the distal tip. The bevel may directly engage the distal end of the curved portion of the cannula (i.e., the bevel may directly engage the radius of curvature).

The cannula may be made from any suitable material with sufficient stiffness to allow it to be advanced through the eye wall and anterior chamber. For example, the cannula may be formed of a metal such as stainless steel, nickel, titanium, aluminum, or alloys thereof (e.g., Nitinol® metal alloy) or a polymer. Exemplary polymers include without limitation, polycarbonate, polyetheretherketone (PEEK), polyethylene, polypropylene, polyimide, polyamide, polysulfone, polyether block amide (PEBAX), and fluoropolymers. In some instances, it may be advantageous to coat the cannula with a lubricious polymer to reduce friction between the ocular tissue and the cannula during the procedure. Lubricious polymers are well known in the art, and include, without limitation, polyvinyl alcohol, polyethylene glycol, polyvinyl pyrrolidone, fluorinated polymers (including poly tetrafluoroethylene (PTFE or Teflon®)), and polyethylene oxide.

The cannula generally has an outer diameter sized to gain access to the lumen of Schlemm's canal while minimally obstructing the surgeon's view. Accordingly, the outer diameter may range from about 150 microns to about 800 microns. The cannula also has an inner diameter, which may range from about 50 microns to about 400 microns. The cannula may also be formed to have any suitable cross-sectional profile, e.g., circular, elliptical, triangular, square, rectangular, etc.

The cannula may be configured to include multiple portions or parts. A cannula having a body, a distal curved portion having a proximal end and a distal end, a radius of curvature defined between the ends, and a bevel at the distal tip of the cannula that directly engages the distal end of the curved portion of the cannula may be particularly useful for accessing the lumen of Schlemm's canal. Here the body (straight portion of the cannula) may have a length ranging from about 5 mm to about 50 mm, about 10 mm to about 30 mm, or from about 14 mm to about 20 mm. In some variations, the body may have a length of about 18 mm. The distal curved portion of the cannula may be uniform in cross-sectional shape or it may taper closer to the distal end to facilitate entry into Schlemm's canal. The radius of curvature of the distal curved portion may be adapted to facilitate tangential entry, as well as precise and minimally traumatic entry into Schlemm's canal, and may range from about 1 mm to about 10 mm or from about 2 mm to about 5 mm. In one variation, the radius of curvature is about 2.5 mm. The cannula may also have an angular span suitable for facilitating entry into Schlemm's canal, and may range from about 70 degrees to about 170 degrees, or about 100 degrees to about 150 degrees. In one variation, the angular span is about 120 degrees.

The size, shape, geometry, etc., of the bevel at the distal end of the curved portion of the cannula may be beneficial in allowing easy and minimally traumatic access to Schlemm's canal. In this respect, and as described in further detail below, having a bevel that directly engages the radius of curvature of the distal end of the cannula may be particularly useful.

In other variations, the cannula may include a short straight segment coupled to the distal end of the distal curved portion of the cannula (e.g., at the end of the radius of curvature). Here the bevel engages the straight segment and not the radius of curvature. The length of the straight segment may range from about 0.5 mm to about 5 mm. In some variations, the length of the straight segment ranges from about 0.5 mm to about 3 mm, or from about 0.5 mm to about 1 mm. The length of the straight segment may also less than about 0.5 mm, e.g., it may be about 0.1 mm, about 0.2 mm, about 0.3 mm, or about 0.4 mm. In variations where the bevel directly engages the distal end of the curved portion of the cannula (i.e., the bevel directly engages the radius of curvature), the cannula lacks a straight segment (length of the straight segment is zero).

It may also be useful to have a bevel that is sharp and short to minimize the distance that any ocular device will have to travel when being implanted into the canal. Exemplary bevel angles may range from about 10 degrees to about 90 degrees. In one variation, the bevel angle is about 35 degrees. The bevel may also be oriented in suitable direction. For example, the bevel may be oriented so that it opens up towards the surgeon, or it may be reversed to open away from the surgeon or in any plane in between.

Figure 27:
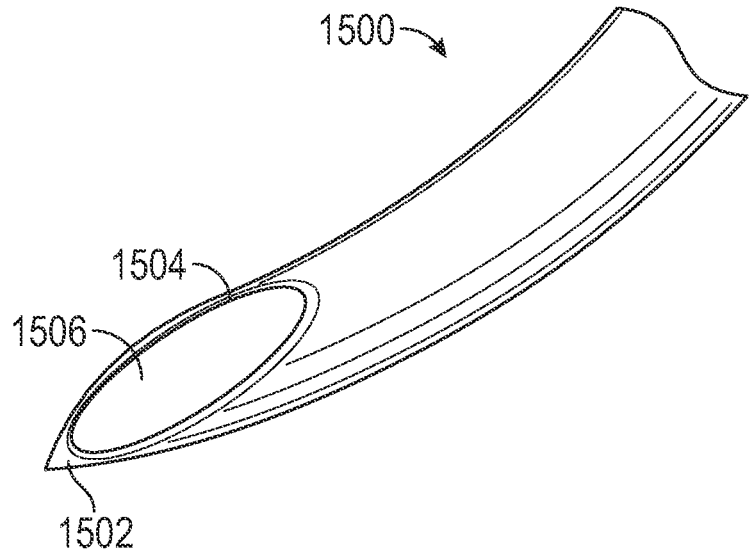
FIG. 27 depicts an exemplary cannula according to another variation.

In yet further variations, the cannula is configured to include one section that is sharp, and another section that is blunt (e.g., deburred). The dual surface configuration of such a cannula may be advantageous since it may provide easier canal access by piercing the meshwork while also providing a gentle, dispersed force on the conduit during conduit retraction into the cannula to avoid cutting or breaking the conduit due to retraction force. For example, as shown in FIG. 27, the distal end of cannula 1500 may have a sharp, piercing tip 1502 and a smooth edge 1504 that define portions of opening 1506, through which 1600 a slidable conduit (FIG. 28) may be advanced and retracted. The sharp tip 1502 may be formed by compounding multiple bevels. The smooth edge 1504 may be created by laser ablation or deburring an inner bevel edge.

The drive assembly of the delivery system is generally configured to move an ocular device, conduit, and/or fluid composition out of the universal handle and into Schlemm's canal. The drive assembly may also be configured to position an ocular device within the canal, including advancing the device into the canal and retracting the device from the canal. The drive assembly may be at least partially contained within the housing and may include any suitable component or combination of components capable of providing the handle with universal functionality. In some variations, the drive assembly includes components that translate rotational motion into linear motion. For example, the drive assembly may include a linear gear and a pair of pinion gear mechanisms. The linear gear may have teeth on its surface that engage corresponding teeth on the pinion gears. Each of the pinion gear mechanisms may also be coupled to a rotatable component (e.g., a wheel). Such coupling may be accomplished with a pin that can be threaded through a central opening in the rotatable component and pinion gear, and a nut that secures the rotatable component and pinion gear in a manner so that rotation of the rotatable component also rotates the pinion gear and vice versa. The wheels may be attached to the pinion gear by one of the following methods: 1) the wheels and pinion gears are molded as one part using plastic injection molding technology; 2) the wheels slide onto the pinion gear and secured with adhesive; or 3) the wheels slide on the pinion gear and are mechanically fixed with a fastener or a "press fit", where the wheels are forced onto the pinion gear and friction holds them secure. In all of the mentioned situations, the wheels and pinion gears may rotate coaxially, in the same direction, and at the same angular rate. In some variations, each of the pinion gear mechanisms is coupled to at least two rotatable components. In other variations, the drive assembly may be configured to include a single rotatable component, a plurality of rotatable components, or no rotatable component. The wheel may have markings or colorings to indicate degree of advancement or direction of advancement.

One variation of the drive assembly useful to include in the universal handle comprises a linear gear, a pair of pinion gear mechanisms, and two rotatable components coupled to each pinion gear (for a total of four rotatable components). Here the pinion gear mechanisms and associated wheels would be disposed on either side of the linear gear. The pinion gears and linear gear would contact each other, i.e., the teeth of the pinion gears would directly engage corresponding teeth on the linear gear, and the wheels on one side of the linear gear would contact the wheels on the opposite side of the linear gear. In this variation, the drive assembly can be manipulated with one hand when in a first configuration, and then manipulated with the other hand when flipped over to a second configuration. A drive assembly having such flexible capability can be easily used by a surgeon who is right hand dominant or left hand dominant. In a further variation, the drive assembly may include one rotatable component on one side of the handle and the "universal" feature of the handle provided by a cannula that itself can rotate instead of flipping the handle.

One or both pinion gear mechanisms can be disengaged from the linear gear by biasing their position off axis from the linear gear. This action de-couples the pinion gear teeth to the linear gear teeth to prevent linear gear movement. The pinion gear mechanism can also be locked to prevent rotation by engaging an intersecting pin or feature that prevents wheel rotation.

In other variations, the drive assembly includes a linear gear and a single pinion gear mechanism with two associated wheels. Further variations of the drive assembly may not employ translation of rotational motion to linear motion. For example, a slide (e.g., a finger slide) on the handle that is fixed or detachably coupled to a gear within the housing of the handle (e.g., a linear gear as previously described) could be used to deliver an ocular device or fluid composition. Here the drive assembly may be configured so that advancement of the slide correspondingly advances components that deliver an ocular device or fluid composition into Schlemm's canal, and retraction of the slide correspondingly retracts those components. In yet further variations, a button that can be pressed by one finger or squeezed by two fingers could be employed instead of a slide.

The ocular delivery systems may further include a slidable positioning element coaxially disposed within the lumen of the cannula for controlled implantation of an ocular device within Schlemm's canal. The positioning element generally comprises a proximal end, a distal end, and an engagement mechanism at the distal end. The ocular device is generally releasably coupled to the engagement mechanism. The positioning element may be advanced to deploy an ocular device within the cannula into Schlemm's canal, or it may be retracted to help with positioning and/or repositioning of an ocular device, or disengagement of an ocular device from the engagement mechanism.

Some variations of the engagement mechanism include a proximal coiled portion and a distal hook. When an implant having at least one fenestration (e.g., a proximal fenestration) is to be implanted, the hook may be releasably engaged to the fenestration. The ocular device may be disengaged from the hook by the application of gentle force on the coil or by another component that can be advanced over the coil to push the device off the hook or by using shape memory materials that passively disengages when exiting the cannula. It may be advantageous to use the hook when retraction of the ocular device is desired. The surgeon may simply move the delivery system and engagement mechanism so that it disengages any fenestration or notch on the implant.

In another variation, the engagement mechanism includes opposing jaws. Here the engagement mechanism may include a first jaw and a second jaw, where the jaws have a closed configuration and an open configuration. The jaws may be used to grip and manipulate the ocular device, and releasably couple the ocular device to the positioning element. The jaws may be formed by splitting or bifurcating the distal end of a wire, e.g., by laser cutting. The grasping force of the jaws may be achieved by constraining the jaws within the cannula. The ocular device may be released once the jaws are advanced out of the cannula and expand. The jaws may also be pivotally connected. In yet another variation, the first jaw may include at least one tine, and the second jaw may include at least one aperture for receiving the tine when the jaws are in the closed configuration.

In further variations, the engagement mechanism comprises a looped portion. This variation of the engagement mechanism will typically be used with an ocular device comprising a spring-like clasp at its proximal end, where the clasp has a collapsed configuration and an expanded configuration. The clasp is generally fabricated in the expanded position. Thus, when a device having a clasp is disposed within the cannula, the first and second arms or tabs of the clasp may collapse around the looped portion of the engagement mechanism. Once the clasped portion of the device has exited the cannula, the arms or tabs may expand to release the ocular device from the looped portion.

Still another variation of the engagement mechanism includes a female to male interface. For example, the engagement mechanism may comprise a notch configured to interface with a complimentary mating element (e.g., a tab) on the ocular device. The notch (female component) may be formed within hypodermic tubing or may be made by creating a fenestration through the distal end of a positioning element made from a solid wire or element, and the tab or hook (male component) may be formed as part of the ocular device and may be inserted into the fenestration or notch in the positioning element. With this configuration, the ocular device may be released from the positioning element as it is advanced out of the cannula either by the surgeon's manipulation or by shape setting of the positioning element that causes it to passively detach from the ocular device or both.

The systems generally include a reservoir when a fluid composition is to be delivered into Schlemm's canal. As further described below, the reservoir may be at least partially defined by a fluid assembly and the housing, and the linear gear within the handle. The fluid assembly may be made from any suitable material previously mentioned for the cannula and the housing. The volume of fluid (in microliters) contained within the reservoir may range from about 2 µl to about 1000 µl, or from about 2 µl to about 500 µl. In some variations, the reservoir volume may range from about 50 µl to about 100 µl Some variations of the fluid assembly include a locking mechanism for preventing movement of the assembly within the handle, e.g., when the linear gear is being advanced or retracted. The locking mechanism may comprise a ratchet pawl, a combination of ratchet pawls or any other suitable mechanism that can be locked to prevent movement of the fluid assembly, and unlocked to allow movement of the fluid assembly.

The fluid composition may be preloaded in the reservoir or loaded into the reservoir prior to use of the system, e.g., at the start of an ocular procedure, so that the fluid can be delivered by a single device and by a single user. Again, this is in contrast to other systems that use forceps or other advancement tools to advance a fluid delivery catheter into Schlemm's canal and/or devices containing viscoelastic fluid that are separate or independent from a delivery catheter or catheter advancement tool, and which require connection to the delivery catheter or catheter advancement tool during a procedure by, e.g., an assistant, or by the hand of the surgeon while the delivery catheter or catheter advancement tool is held by another hand of the surgeon. For example, a loading component may be provided on the fluid assembly for transfer of a fluid composition into the reservoir. The loading component may have any suitable configuration that provides reversible securement of a fluid container, e.g., a syringe, cartridge, etc., to the system, and loading of a fluid composition into the reservoir. The loading component may be a luer fitting or include a one-way valve. A slidable conduit coaxially disposed within the cannula lumen may be operatively connected to the reservoir for delivery of a fluid composition into Schlemm's canal. The slidable conduit generally has a proximal end, a distal end, and a wall that defines a conduit lumen extending therethrough. However, in some instances, the delivery system lacks a slidable conduit, and the fluid composition is delivered solely through the cannula. In other instances, two slidable conduits may be employed that each simultaneously advance through the canal in both clockwise and counterclockwise directions to more rapidly cannulate Schlemm's canal and deliver therapy. As previously stated, the fluid may be delivered in a volume that provides sufficient force to disrupt Schlemm's canal and surrounding trabeculocanalicular tissues. Exemplary disruptive volumes may be about 1 µl, about 2 µl, about 3 µl, about 4 µl, about 5 µl, about 6 µl, about 7 µl, about 8 µl, about 9 µl, about 10 µl, about 11 µl, about 12 µl, about 13 µl, about 14 µl, about 15 µl, about 16 µl, about 17 µl, about 18 µl, about 19 µl, or about 20 µl. In some variations, the disruptive volume fluid may range from about 1 µl to about 50 µl, or from about 20 µl to about 50 µl.

The slidable conduit may be made from any suitable material that imparts the desired flexibility and pushability for introduction through the eye wall, accessing Schlemm's canal, and/or navigation through other ocular tissue structures. For example, the conduit may comprise a polymer; a polymer reinforced with metal wire, braid or coil; composites of polymers and metal; or metals such as stainless steel, titanium, nitinol, or alloys thereof. The slidable conduit may be straight with enough flexibility and pushability to navigate the ring-shaped Schlemm's canal or may be pre-shaped to about a 2-10 mm radius of curvature or about a 6 mm radius of curvature (i.e. the approximate radius of curvature of Schlemm's canal in an adult human) to more easily circumnavigate Schlemm's canal, partially or in its entirety. In some other variations, the slidable conduit includes a plurality of openings through its wall that are spaced along the axial length of the conduit. In this variation, the fluid composition may be delivered from the reservoir through the openings in the conduit and into Schlemm's canal. This lateral ejection of fluid (e.g., a viscoelastic fluid) would further enhance disruption of outflow tissues and enhance permeability to aqueous humor. It is understood that the openings can be of any suitable number, size and shape, and spaced along the axial length of the conduit (including the distal end) in any suitable manner. In other variations, the distal end of the slidable conduit may be configured or modified to aid delivery of the fluid composition into Schlemm's canal. For example, the distal end of the conduit may comprise a cut out configured as a half tube. The distal end of the conduit may also be configured as a blunt bevel, an atraumatic tip, an enlarged atraumatic tip, or a rough surface that disrupts the juxtatrabecular portion of Schlemm's canal or juxtatrabecular meshwork. Additionally, the conduit may have one or more projections emanating from it to further disrupt the juxtatrabecular portion of Schlemm's canal or juxtatrabecular meshwork and thus increase permeability of aqueous humor through the trabecular meshwork into Schlemm's canal. In some instances, the conduit may also deliver energy to the trabeculocanalicular tissues. In other instances, the conduit may be an off the shelf commercially available or customized polypropylene suture (or other material). The suture may be sized so that it can be advanced through the cannula and into a portion of Schlemm's canal (e.g., 0 to 360 degrees of the canal) to disrupt, stent, and/or apply tension to the canal, and/or to tear the trabeculocanalicular tissues. An exemplary range of suture size may range from about 50 microns to about 300 microns. The suture may be removed from the canal or left within the canal to continuously deliver tension on the meshwork and maintain patency of the canal.

The cannula of the systems described herein may also deliver various surgical tools by ab-interno methods. For example, catheters, wires, probes, and other tools may also be employed ab-interno to access Schlemm's canal and then to create holes, partial thickness disruptions, or perforations in discreet locations or all along the trabecular meshwork or inner wall of Schlemm's canal. The surgeon may also advance the tools all the way across the canal and through the collector channel outer wall to access the sclera and subconjunctival space (again all from an ab-interno approach) to make incisions that create a scleral lake into which aqueous can drain to the scleral veins or subconjunctival space or to deliver an ocular device ab-interno that resides and drains into the scleral lake or sub conjunctival space from the anterior chamber or Schlemm's canal.

The reservoir may contain various fluid compositions for delivery into Schlemm's canal. Exemplary fluid compositions include saline and viscoelastic fluids. The viscoelastic fluids may comprise hyaluronic acid, chondroitin sulfate, cellulose, derivatives or mixtures thereof, or solutions thereof. In one variation, the viscoelastic fluid comprises sodium hyaluronate. In another variation, the viscoelastic composition may further include a drug. For example, the viscoelastic composition may include a drug suitable for treating glaucoma, reducing or lowering intraocular pressure, reducing inflammation, and/or preventing infection. Drugs such as an antimetabolite, steroid, heparin, other anticoagulants, and fibrinolytic compounds may also be delivered in combination with the viscoelastic composition. Examples of glaucoma drugs include prostaglandins, beta blockers, miotics, alpha adrenergic agonists, or carbonic anhydrase inhibitors. Anti-inflammatory drugs such as corticosteroids or other steroids may be used. For example, steroids such as prednisolone, prednisone, cortisone, cortisol, triamcinolone, or shorter acting steroids may be employed. Examples of antimetabolites include 5-fluorouracil or mitomycin C. In still another variation, the system delivers the drug alone, without the viscoelastic composition. Saline solution may also be the fluid employed.

In other variations, the devices/systems may include a slidable conduit that does not deliver a fluid, but which is sized to have an outer diameter sufficient to disrupt Schlemm's canal and surrounding trabeculocanalicular tissues. The outer diameter may range from about 50 microns to about 500 microns, from about 300 microns to about 500 microns, from about 200 microns to about 250 microns, or from about 180 microns to about 300 microns. In some instances it may be beneficial for the conduit to have an outer diameter of about 240 microns. Furthermore, a distal portion of the conduit may include a disruptive component, e.g., a notch, hook, barb, or combination thereof, to disrupt tissues.

Figure 14:
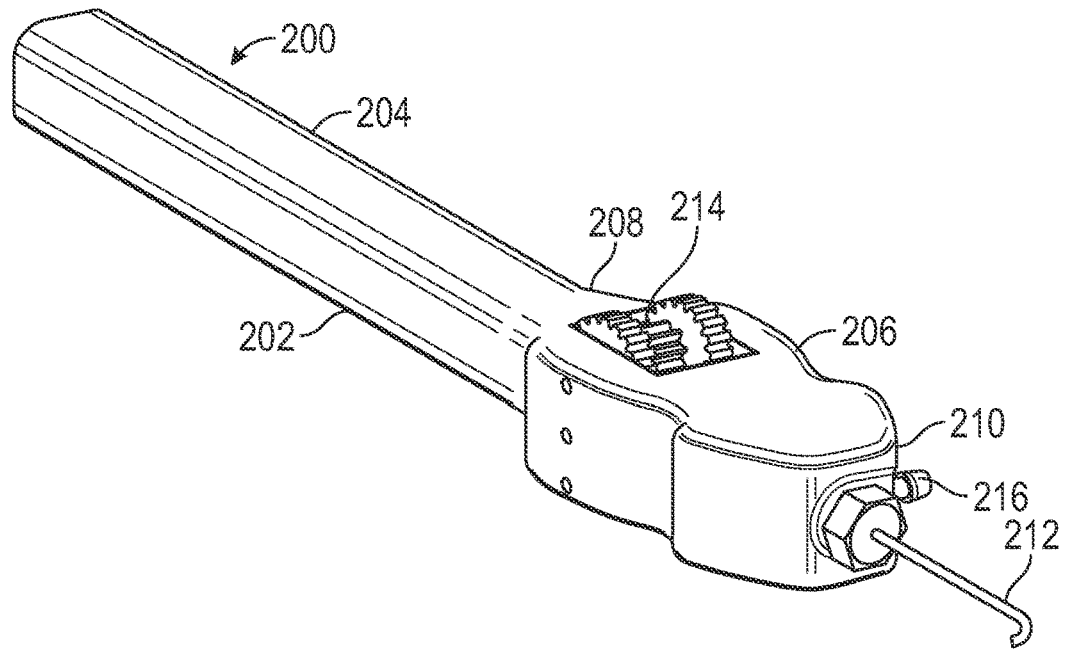
FIG. 14 depicts a perspective view of an exemplary delivery system for implanting an ocular device.

An exemplary ocular delivery system is depicted in FIG. 14. In the figure, delivery system 200 includes a universal handle 202 having a grip portion 204 and a housing 206. The housing has a proximal end 208 and a distal end 210. A cannula 212 is coupled to and extends from the housing distal end 210. A drive assembly 214 is substantially contained within the housing 206 that actuates movement of a positioning element (not shown). Port 216 is provided on the distal end of the housing 210 for removable connection to a source of irrigation fluid.

Figure 15:
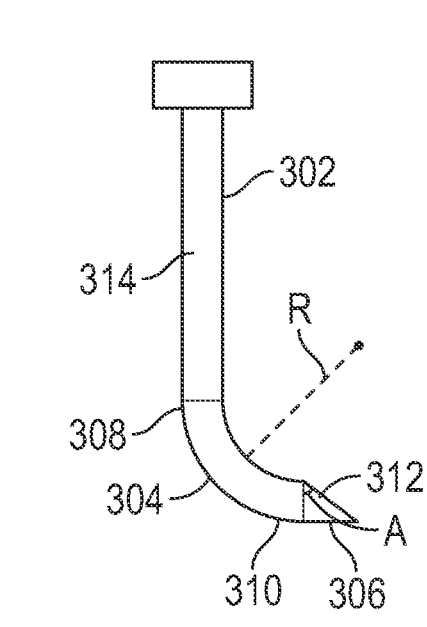
FIG. 15 depicts a side view of an exemplary cannula of the delivery system.

The cannula of an exemplary delivery system is shown in more detail in FIG. 15. Here the cannula 300 comprises a proximal end 302 a distal curved portion 304, a body 314, and a distal tip 306. The distal curved portion 304 has a proximal end 308 and a distal end 310, and a radius of curvature R that is defined between the ends 308, 310. A bevel 312 at the distal tip 306 directly engages the distal end of the curved portion of the cannula 310. In other words, the bevel 312 may be contiguous with the distal end of the curved portion of the cannula 310. As previously stated, this configuration of the distal curved portion 304 and bevel 312 may be beneficial or advantageous for allowing easy, atraumatic, and controlled access into Schlemm's canal. The angle of the bevel may also be important. In general, a short bevel may be beneficial. Here the bevel angle A is about 35 degrees.

Figure 16A:
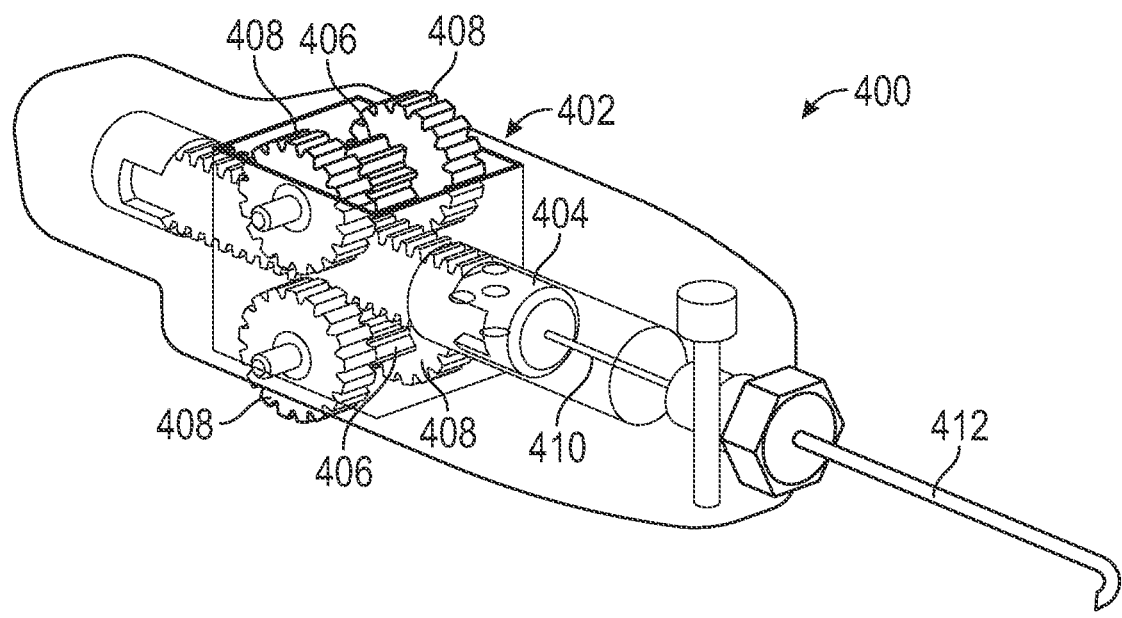
FIG. 16A depicts a perspective view of an exemplary drive assembly in the handle of the system in a first orientation for use with one hand.
Figure 16B:
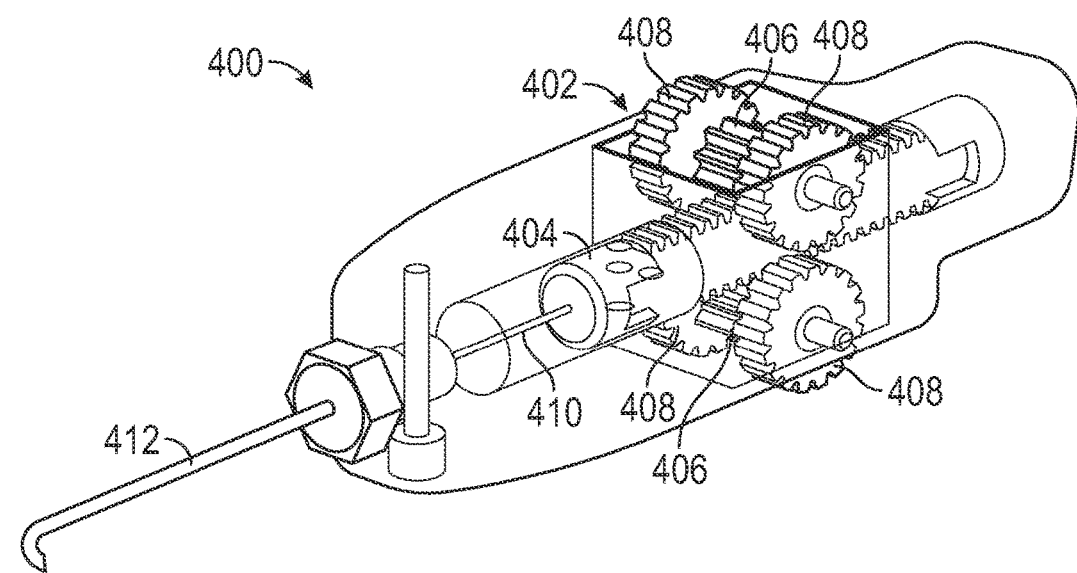
FIG. 16B depicts a perspective view of FIG. 16A with the handle in a second, flipped orientation that can be used with the other hand.

The ocular delivery systems generally include a drive assembly substantially contained within the housing. In the variation shown in FIG. 16A, delivery system 400 includes a drive assembly 402 having a linear gear 404 (e.g., a rack) and a pair of pinion gear mechanisms 406. Both the linear gear and the pinion gear mechanisms have teeth that engage each other to translate rotational motion (of the pinion gear mechanisms 406) to linear motion (of the linear gear 404). Each of the pinion gear mechanisms 406 are coupled to two rotatable components, shown in the figure as wheels 408, for a total of four rotatable components. The wheels 408 may be rotated by one or more of the surgeon's fingers to correspondingly rotate the pinion gear mechanism 406 and thus advance or retract the linear gear 404. The wheels 408 are coaxial with the pinion gear mechanism 406 and rotate in unison with the pinion gear mechanism. Movement of the linear gear 404 advances or retracts a positioning element 410 that is coaxially disposed and slidable within cannula 412. FIG. 16B shows the system of FIG. 16A in a second, flipped orientation that can be used with the opposite hand (e.g., by the left hand if the system of FIG. 16A was used with the right hand), or that can be used by the same hand, but a different direction of cannulation is desired (e.g., clockwise cannulation if counterclockwise cannulation was performed with the system in FIG. 16A).

When the delivery system is used to implant an ocular device, the cannula may have a slidable positioning element coaxially disposed within the cannula lumen. The slidable positioning elements generally include an engagement mechanism for manipulating, e.g., releasably engaging, advancing and/or retracting, an ocular device. Exemplary engagement mechanisms are depicted in FIGS. 17-21.

Figure 17A:
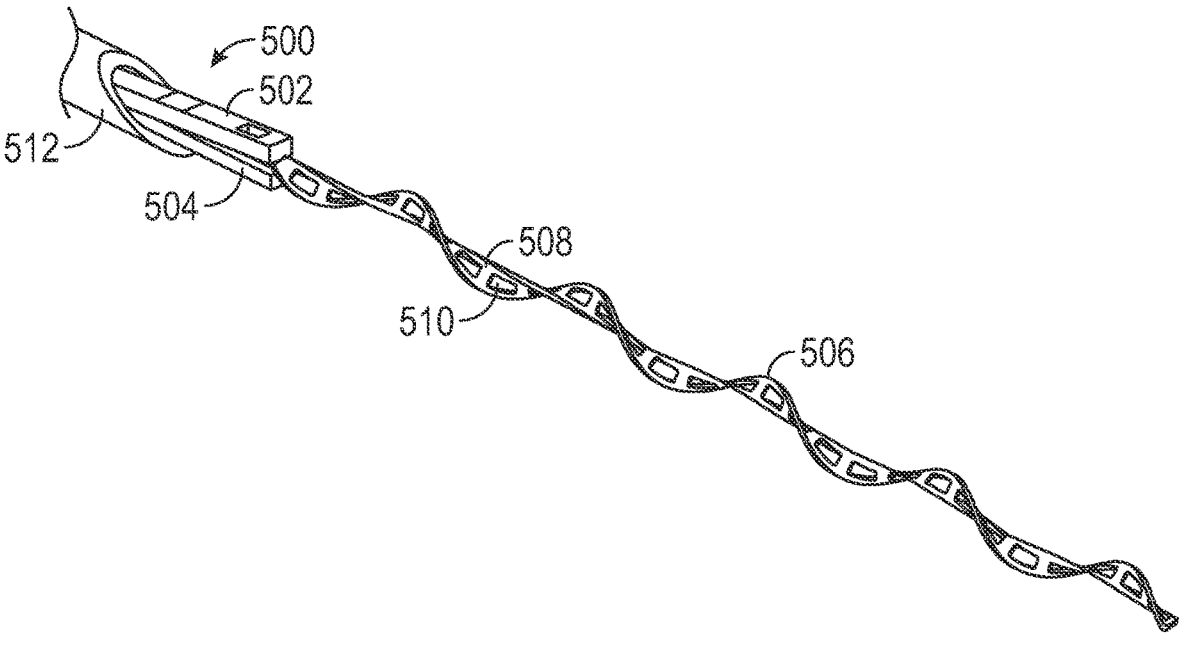
FIGS. 17A-17B depict perspective views of an exemplary engagement mechanism.
Figure 17B:
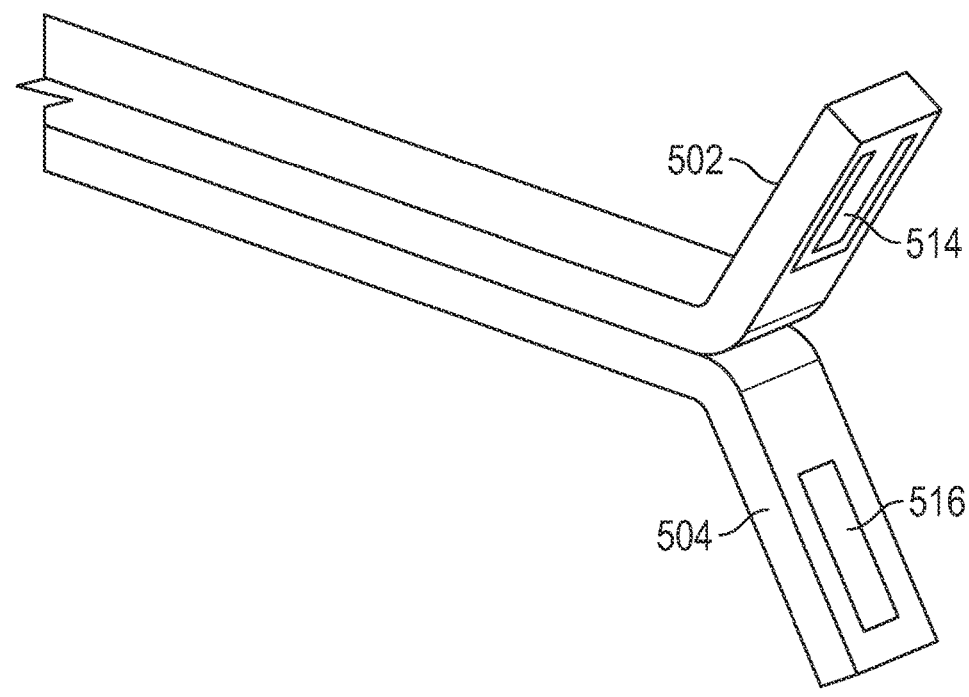
Figure 18:
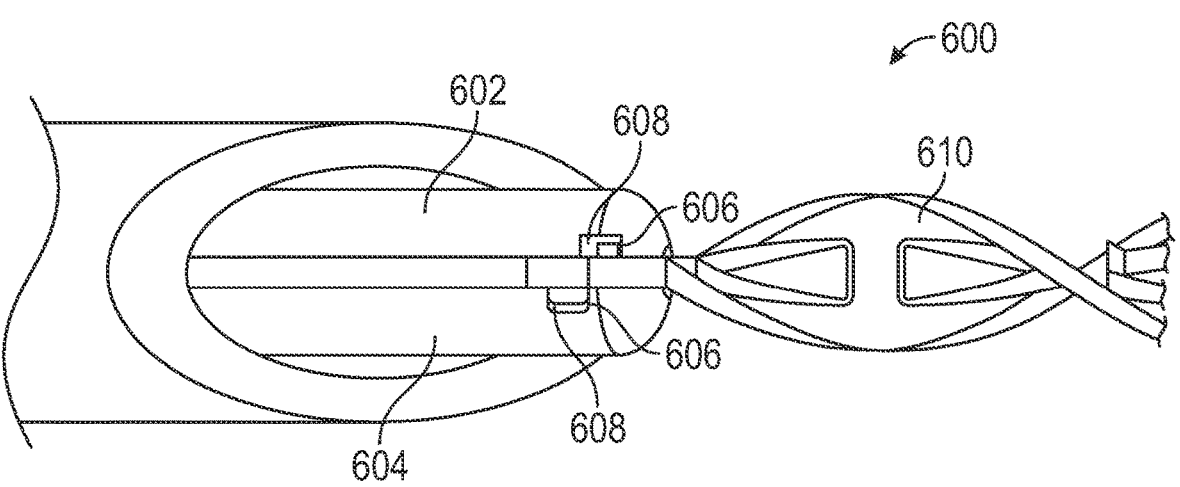
FIG. 18 depicts a perspective view of an engagement mechanism according to one variation.

In FIG. 17A, the engagement mechanism 500 comprises a first jaw 502 and a second jaw 504. In their closed configuration (as shown in FIG. 17A), the jaws 502, 504 are constrained within cannula 512 and hold an ocular device 506 comprising a support 508 and at least one fenestration 510. When the jaws 502, 504 are advanced out of cannula 512 they are no longer constrained, and thus take the form of their open configuration, as shown in FIG. 17B. Opening of the jaws 502, 504 releases ocular device 506 from the engagement mechanism 500. At least one tine 514 may be provided in the first jaw 502 and at least one aperture 516 may be provided in the second jaw 504 to help secure a fenestrated ocular device when the jaws are in their closed configuration. In FIG. 18, a variation of an engagement mechanism 600 is shown where a first jaw 602 and a second jaw 604 include both a tine 606 and an aperture 608 to help grasp a fenestrated ocular device 610.

Figure 19A:
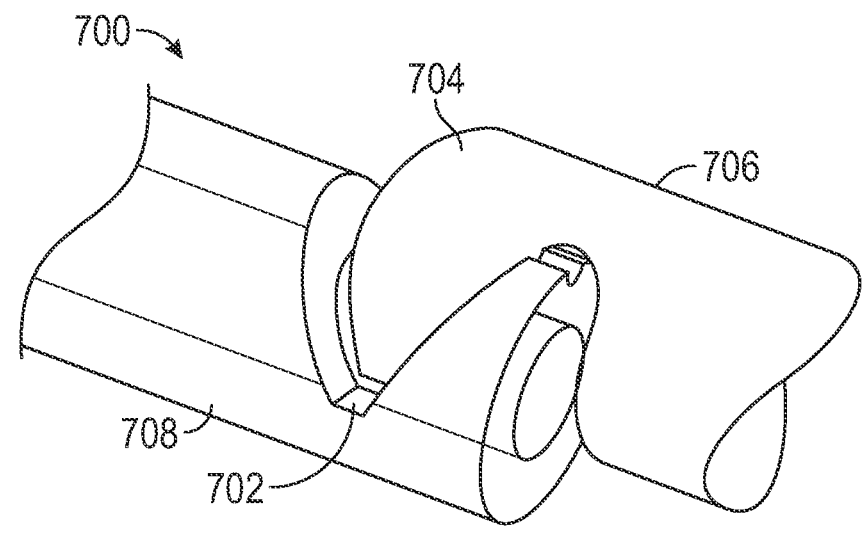
FIG. 19A-19B depict perspective views of engagement mechanisms according to other variations.
Figure 19B:
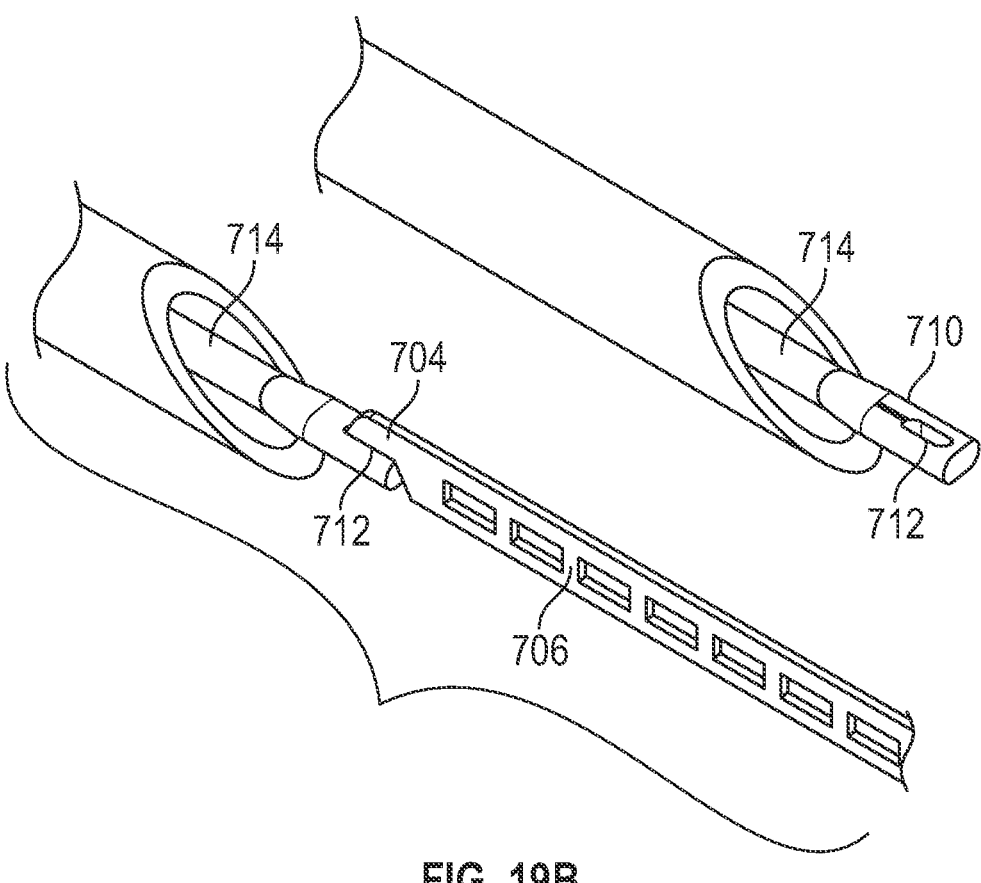

Referring to FIGS. 19A-19B, further exemplary engagement mechanisms are depicted. In FIG. 19A, engagement mechanism 700 comprises complementary mating elements. Specifically, engagement mechanism 700 includes a female element, notch 702 that is configured to interface with a complimentary male element 704, shown as a hook-like projection on the ocular device 706. Here the notch 702 may be fabricated at the end of a hypodermic tube 708 (which would serve as the positioning element). Instead of notch 702, the female element of the engagement mechanism 710 may include an opening 712, as shown FIG. 19B, which interfaces with male element 704 on the ocular device 706. In FIG. 19B, the positioning element 714 may be fabricated from a metal wire or rod and the opening 712 created via laser machining or other processes known in the art.

Figure 20A:
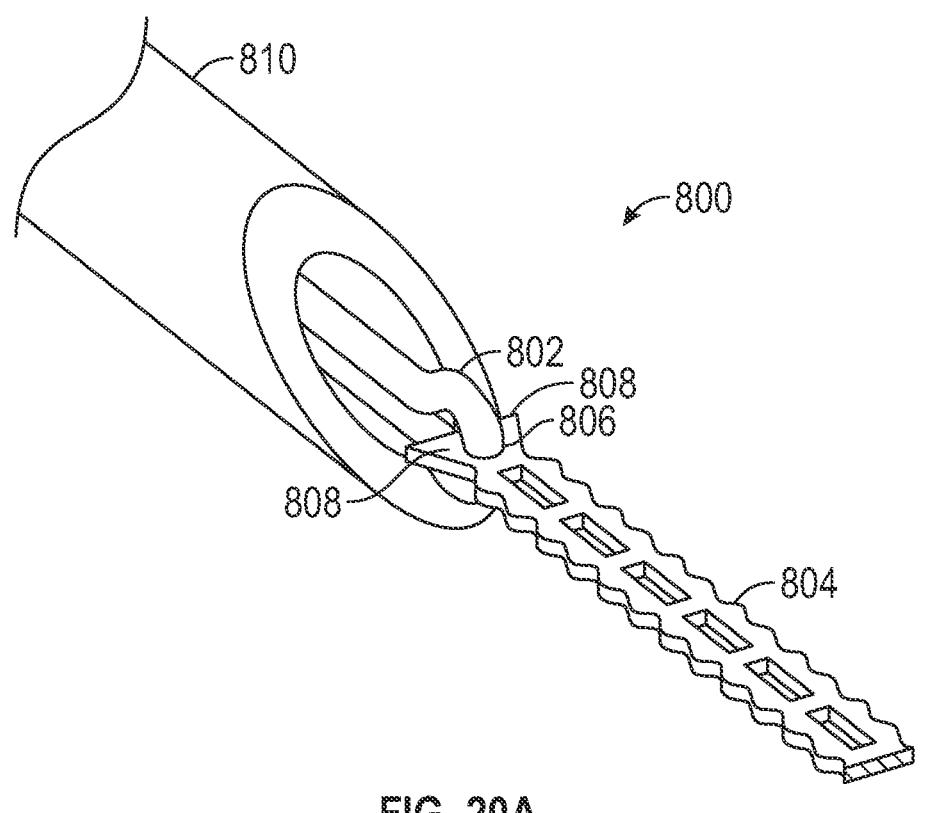
FIG. 20A-20B depict perspective views of an engagement mechanism according to yet a further variation.
Figure 20B:
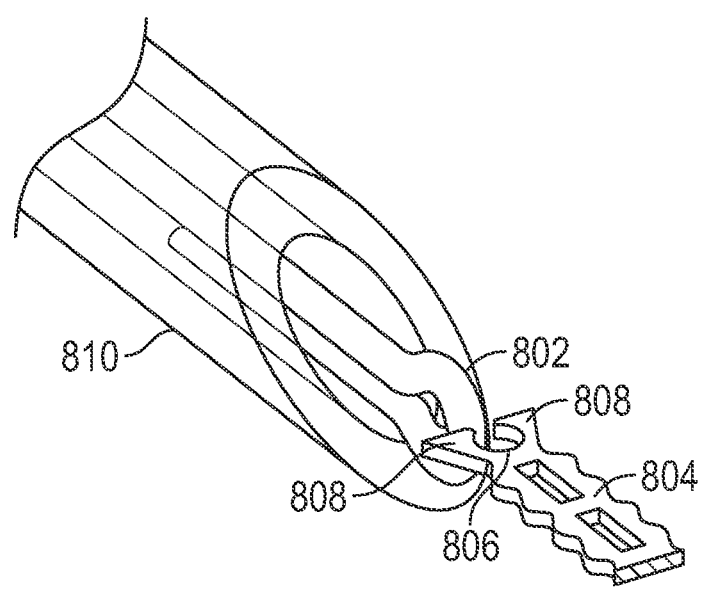

In other variations, the engagement mechanism may be configured as shown in FIGS. 20A and 20B. In those figures, engagement mechanism 800 comprises a looped portion 802. It may be beneficial to use this particular engagement mechanism with an ocular device 804 including a clasp 806 with arms or tabs 808 having a closed configuration and an expanded configuration. Similar to the variation shown in FIGS. 17A and 17B, tabs 808 are constrained in their closed configuration within the cannula 810 prior to advancement out of the cannula 810. In their constrained configuration, tabs 808 engage the looped portion 802 of the engagement mechanism 800 to prevent release of the ocular device 804 from the system. When the looped portion 802 of the engagement mechanism 800 is advanced sufficiently so that tabs 808 are no longer constrained by cannula 810, tabs 808 take on their expanded configuration to thus release the ocular device 804 from the looped portion 802 and into Schlemm's canal, as shown in FIG. 20B.

Figures 21, 22A, 22B:
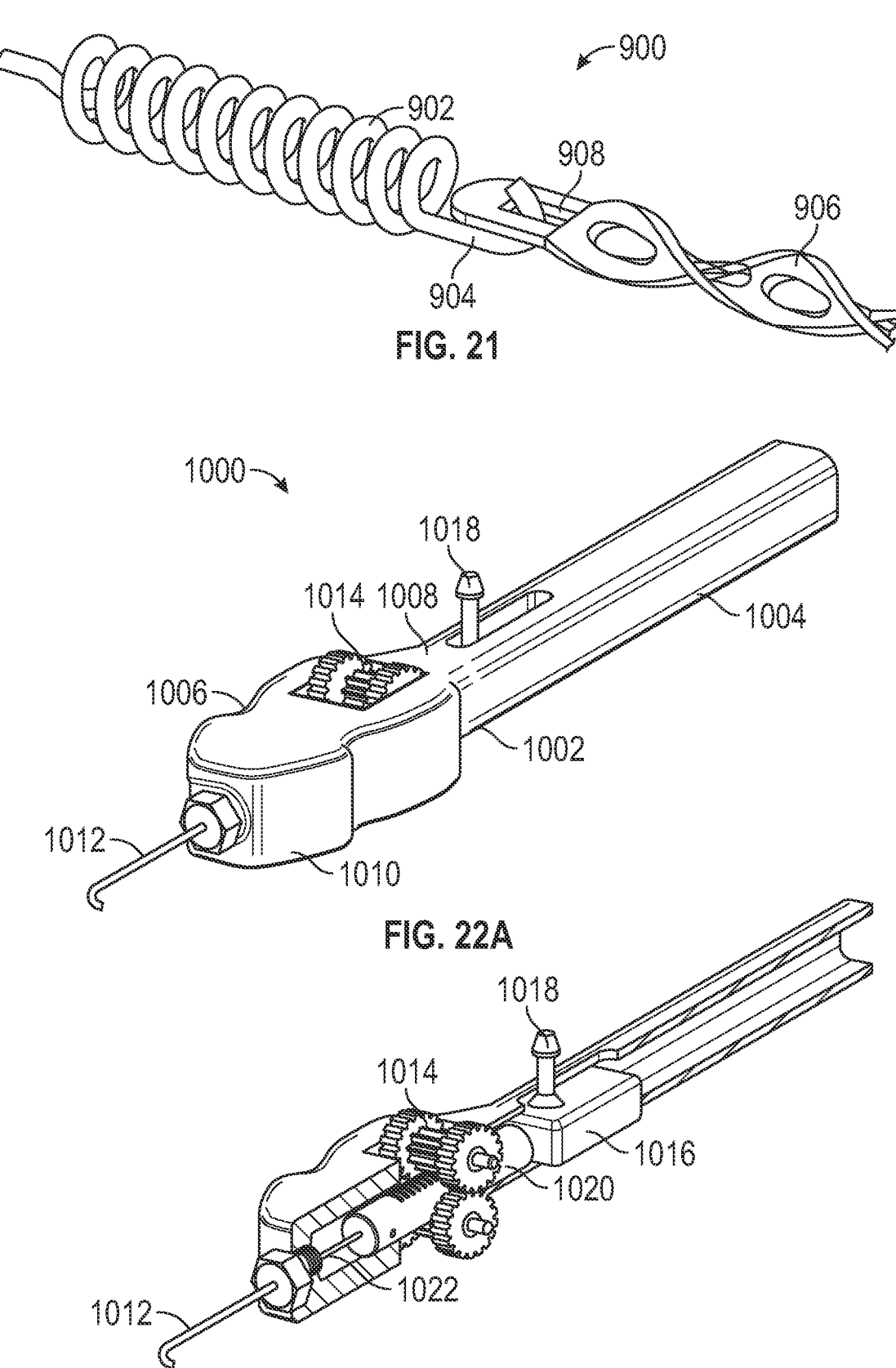
FIG. 21 depicts a perspective view of another exemplary engagement mechanism.
FIG. 22A depicts a perspective view of an exemplary delivery system for delivering a fluid composition into Schlemm's canal.
FIG. 22B depicts a partial cross-sectional perspective view of the delivery system of FIG. 22A.

Another exemplary engagement mechanism 900 is shown in FIG. 21 comprising a coiled portion 902 and a hook 904. When an ocular device 906 having at least one fenestration 908 (e.g., a proximal fenestration) is to be implanted, the hook 904 may be releasably engaged to the fenestration 908. The ocular device 906 may be disengaged from the hook by the application of gentle force on the coil 902 or by another component (not shown) that can be advanced over the coil 902 to push the device 906 off the hook 904. It may be advantageous to use the hook 904 when retraction of the ocular device 906 is desired.

When the delivery systems are employed to deliver a fluid composition, the fluid composition may be preloaded in a reservoir of the system or loaded into the reservoir prior to use of the system. An exemplary delivery system for delivering a fluid composition into Schlemm's canal is shown in FIGS. 22A and 22B. Referring to FIG. 22A, delivery system 1000 includes a universal handle 1002 having a grip portion 1004 and a housing 1006. Housing 1006 has a proximal end 1008 and a distal end 1010. A cannula 1012 is coupled to and extends from the housing distal end 1010. A drive assembly 1014 is substantially contained within the housing 1006 that actuates movement of a slidable conduit (not shown). The cannula 1012 and drive assembly 1014 have the same configuration as that shown and described in FIGS. 15 and 16A-16B for the system tailored for ocular device implantation, and thus are not described in detail here.

The delivery system 1000 also includes a fluid assembly 1016 (shown in FIG. 22B) within the handle 1002 having a loading component 1018 that is configured to allow transfer of a fluid composition from an external source into a reservoir defined by the fluid assembly and linear gear 1020. A slidable conduit 1022 is coaxially disposed within the cannula lumen that is in fluid communication with the reservoir. As previously stated, in a tool-based system that does not deliver an implant or a fluid, the system may not include a reservoir.

Figures 23A, 23B, 23C, 24:
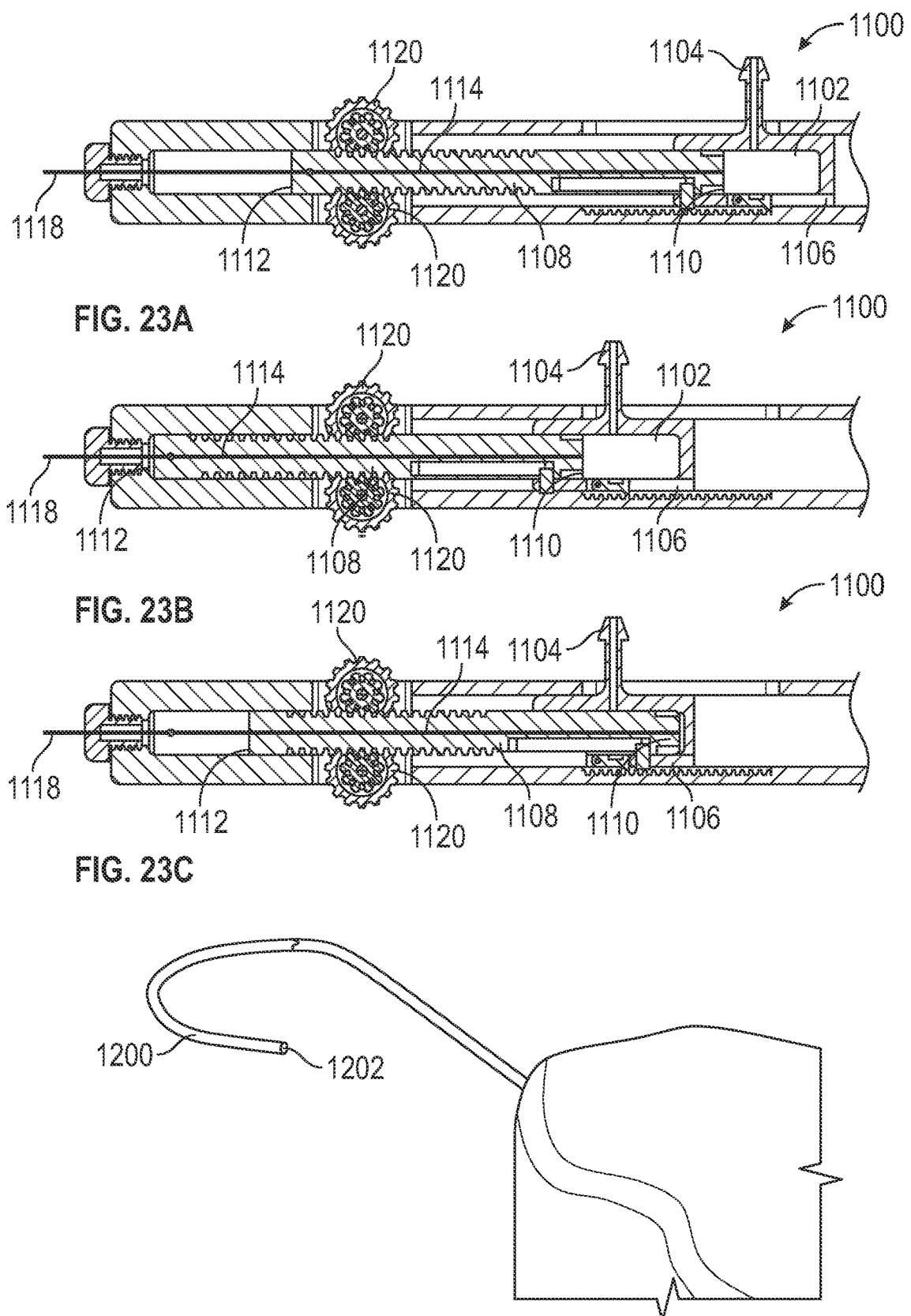
FIGS. 23A-23C depicts an exemplary method of delivering a fluid composition out of the delivery system.
FIG. 24 depicts an exemplary slidable conduit for delivering a fluid composition.

In an exemplary method, as illustrated by FIGS. 23A-23C, a fluid composition may be transferred into a reservoir 1102 of system 1100 via loading through loading component 1104. As shown in the figures, reservoir 1102 is defined by the fluid assembly 1106 and the linear gear 1108. Linear gear 1108 has a proximal end 1110 and a distal end 1112, and a lumen 1114 extending from the proximal end 1110 to the distal end 1112. Lumen 1114 is in fluid communication with the lumen (not shown) of the slidable conduit 1118.

To deploy the fluid composition out of the reservoir 1102, linear gear 1108 is retracted in the direction of the arrow (FIG. 23B) so that reservoir 1102 becomes pressurized. Retraction can be accomplished by rotation of pinion gear mechanisms 1120. Once a sufficient amount of pressure has been created in the reservoir 1102 the fluid composition contained therein is injected through linear gear lumen 1114 and conduit 1118 into Schlemm's canal.

Figure 25A:
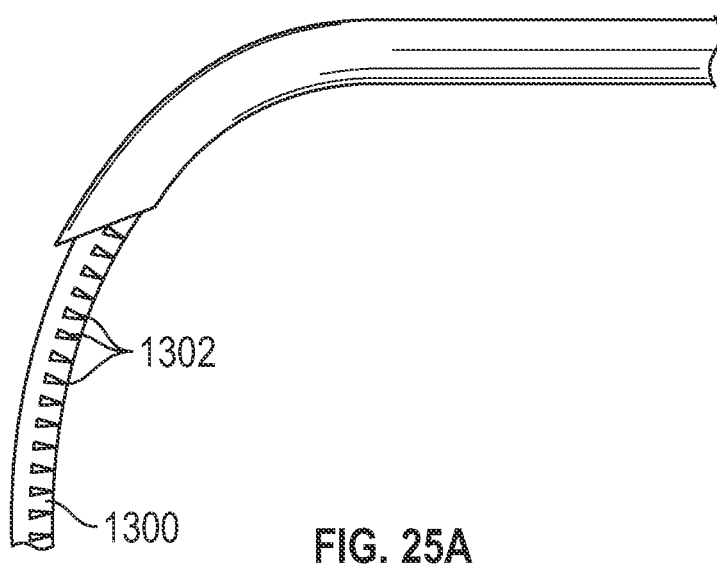
FIGS. 25A-25C depict side or perspective views of slidable conduits according to other variations.
Figure 25B:
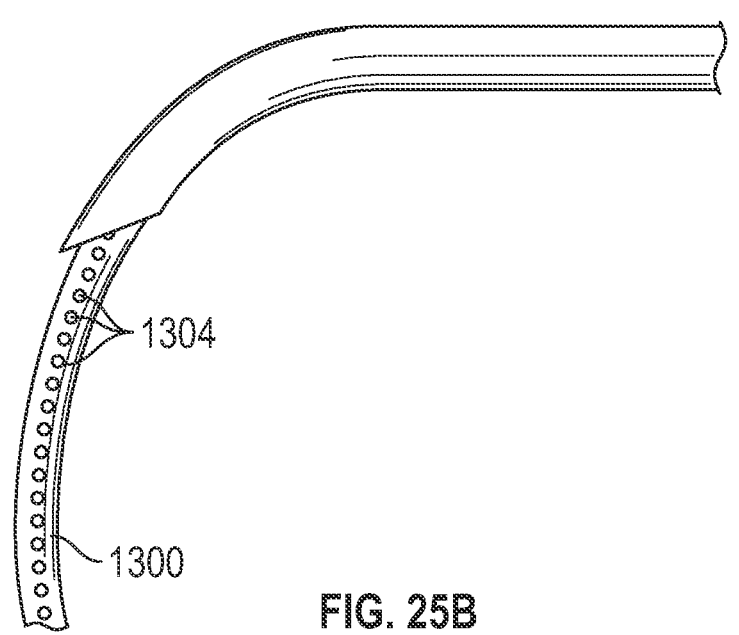
Figure 25C:

The slidable conduits employed with the systems described herein may be of various configurations. For example, as shown in FIG. 24, the conduit 1200 may be a flexible tube having a lumen in fluid communication with an opening at the distal end 1202. Here, any fluid that is delivered flows through the distal end 1202 to reach Schlemm's canal. In other variations, the slidable conduit 1300 may be configured to include a plurality of openings spaced along its axial length. The openings may have any suitable shape, e.g., slots 1302 (FIG. 25A) or circles 1304 (FIG. 25B). Fluid compositions delivered using the conduits depicted in FIG. 25A and FIG. 25B may partially flow out of the conduit through the openings and partially out through the distal end of the conduit. The distal end of the conduit may also be configured as a half tube 1306 (FIG. 25C).

Methods for implanting an ocular device and for delivering a fluid composition into Schlemm's canal using the systems described above are also provided. Implant-free methods for providing a force sufficient to disrupt trabeculocanalicular tissues, e.g., by providing a disruptive volume of viscoelastic fluid or a disruptive tool, are further described. The methods are generally single-handed, single-operator controlled methods that are minimally invasive, e.g., they are tailored for an ab-interno procedure, which as previously mentioned, can be advantageous over the more invasive ab-externo approach. However, use of the ocular systems in an ab-externo method may be contemplated in some instances and thus, are not excluded here. The methods for delivering an ocular device or fluid, or for providing a disruptive force, may be used to treat glaucoma, pre-glaucoma, or ocular hypertension. When treating glaucoma, the methods may also be used in conjunction with a cataract surgery (before or after) using the same incision.

Figure 26:
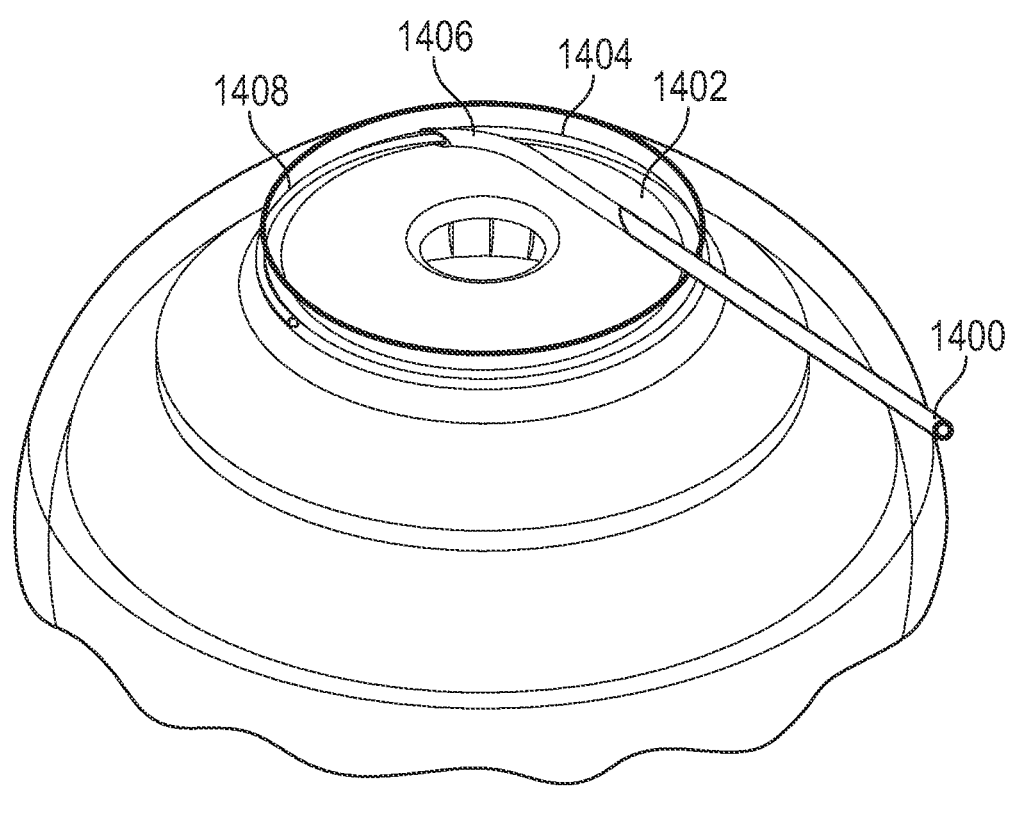
FIG. 26 depicts a stylized depiction of an ab-interno method for accessing Schlemm's canal with the cannula of an exemplary delivery system.

In general, the methods for implanting an ocular device within Schlemm's canal first include the step of creating an incision in the ocular wall (e.g., the sclera or cornea) that provides access to the anterior chamber of the eye. As shown in the stylized depiction of an eye in FIG. 26, the cannula 1400 of the ocular delivery system is then advanced through the incision and at least partially across the anterior chamber 1402 to the trabecular meshwork (not shown). Schlemm's canal (i.e., the lumen of Schlemm's canal) 1404 is then accessed with the distal curved portion of the cannula 1406 and a slidable positioning element, (or, e.g., a slidable tool or guidewire), or slidable conduit (represented generically by element 1408) is advanced from the cannula to implant an ocular device within Schlemm's canal, perform a procedure within Schlemm's canal or on any of the neighboring trabeculocanalicular tissues, or deliver a fluid into the canal. However, in some instances, a slidable conduit may not be employed so that any fluid to be delivered is delivered through the cannula. In yet further variations, just the trabecular meshwork is punctured and the fluid composition is delivered without circumnavigation of Schlemm's canal.

As previously stated, the cannula may be configured to include a proximal end and a distal curved portion, where the distal curved portion has a proximal end, a distal end, and a radius of curvature defined between the ends. Here the cannula may also include a body and a distal tip having a bevel that directly engages the radius of curvature, e.g., it is contiguous with the radius of curvature. The method may also include the step of flushing the system with fluid (e.g., to remove air from the system) and/or the step of irrigating the operative field to clear away blood or otherwise improve visualization of the field.

Any suitable ocular device that maintains the patency of Schlemm's canal or improves outflow of aqueous humor may be implanted by the systems described herein. For example, ocular devices that maintain the patency of Schlemm's canal without substantially interfering with fluid flow across and along the canal may be implanted. Such devices may comprise a support having at least one fenestration. Ocular devices that disrupt the juxtacanalicular trabecular meshwork or adjacent inner wall of Schlemm's canal may also be implanted. In addition to ocular devices made from metal or metal alloys, the use of sutures, modified sutures, modified polymers, or solid viscoelastic structures may be delivered. Fluid compositions such as saline, viscoelastic fluids, air, and gas may also be delivered.

When a fluid composition is delivered into Schlemm's canal, the methods generally include the steps of creating an incision in the ocular wall (e.g., the sclera or cornea) that provides access to the anterior chamber of the eye; advancing a cannula of the ocular delivery system through the incision and at least partially across the anterior chamber to the trabecular meshwork; accessing Schlemm's canal with the cannula; and delivering the fluid composition into the canal using a conduit slidable within the cannula lumen. The cannula may be configured to include a proximal end and a distal curved portion, where the distal curved portion has a proximal end, a distal end, and a radius of curvature defined between the ends. Here the cannula may also include a body and a distal tip having a bevel that directly engages the radius of curvature, e.g., it is contiguous with the radius of curvature. Further advantageous cannula features may also be included, which are described above. The method may also include the step of flushing the system with fluid (e.g., to remove air from the system) and/or the step of irrigating the operative field to clear away blood or otherwise improve visualization of the field.

When an ab-interno method is employed for implanting an ocular device, the method may include the following steps. The surgeon may first view the anterior chamber and trabecular meshwork (with underlying Schlemm's canal) using an operating microscope and a gonioscope or gonioprism. Using a 0.5 mm or greater corneal, limbal, or sclera incision, the surgeon may then gain access to the anterior chamber. A saline solution or viscoelastic composition may then be introduced into the anterior chamber to prevent its collapse. Here the saline solution or viscoelastic composition may be delivered through the delivery system cannula or by another mode, e.g., by infusion through a sleeve on the cannula. The surgeon, under direct microscopic visualization, may then advance the cannula of the delivery system through the incision towards the anterior chamber angle. When nearing the angle (and thus the trabecular meshwork), the surgeon may apply a gonioscope or gonioprism to the cornea to visualize the angle. The application of a viscous fluid (e.g., a viscoelastic composition as previously described) to the cornea and/or gonioscope or gonioprism may help to achieve good optical contact. As the surgeon visualizes the trabecular meshwork, the cannula may then be advanced so that the bevel of at the distal end of the curved distal portion of the cannula pierces the meshwork and is in communication with the lumen of Schlemm's canal. The surgeon may irrigate saline or a viscoelastic composition into the canal or into the anterior chamber to either prevent collapse of chamber, dilate Schlemm's canal, or wash away any blood that may obscure visualization of cannula and ocular device delivery. Next, when the ocular device is advanced to the extent desired by the surgeon, it is released from the engagement mechanism so that it can reside in Schlemm's canal. If repositioning of the ocular device is needed or desired, the surgeon may retract and/or reposition the ocular device using the positioning element of the delivery system. The surgeon may then withdraw the delivery system from the eye.

Other variations of the ab-interno method for implanting an ocular device include the use of an endoscope. Similar to the method above, access to the anterior chamber is first made by incising the cornea, limbus, or sclera. Again, this may be done in combination with cataract surgery in one sitting, either before or after cataract surgery, or independently. The anterior chamber may be infused with saline solution or a viscoelastic composition may be placed in the anterior chamber to prevent its collapse. The saline or viscoelastic may be delivered as a separate step or it may be infused with the conduit of the delivery system, a sleeve on the conduit, or with a separate infusion cannula. The surgeon, under direct microscopic visualization, then advances the endoscope through the incision and towards the angle and trabecular meshwork. As the surgeon visualizes the trabecular meshwork using the endoscope or any associated video display, the bevel of the cannula is advanced to pierce the meshwork. The ocular device is then advanced using the positioning element under endoscopic visualization. The surgeon may irrigate saline or a viscoelastic composition into the canal or into the anterior chamber to either prevent collapse of chamber, dilate Schlemm's canal, or wash away any blood that may obscure visualization of cannula and ocular device delivery. When the ocular device is advanced to the extent desired by the surgeon, it is released from the engagement mechanism so that it can reside in Schlemm's canal. If repositioning of the ocular device is needed or desired, the surgeon may retract and/or advance the ocular device using the positioning element of the delivery system. The surgeon may then withdraw the delivery system from the eye.

With respect to the delivery of a fluid composition, the methods are similar to the implantation of an ocular device. However, instead of using a positioning element, the delivery system employs a slidable conduit to infuse a fluid composition into Schlemm's canal. The surgeon may first view the anterior chamber and trabecular meshwork (with underlying Schlemm's canal) using an operating microscope and a gonioscope or gonioprism. Using a 0.5 mm or greater corneal, limbal, or sclera incision, the surgeon may then gain access to the anterior chamber. A saline solution or viscoelastic composition may then be introduced into the anterior chamber to prevent its collapse. Here the saline solution or viscoelastic composition may be delivered through the delivery system cannula or by another mode, e.g., by infusion through a sleeve on the cannula. The surgeon, under direct microscopic visualization, may then advance the cannula of the delivery system through the incision towards the anterior chamber angle. When nearing the angle (and thus the trabecular meshwork), the surgeon may apply a gonioscope or gonioprism to the cornea to visualize the angle. The application of a viscous fluid (e.g., a viscoelastic composition as previously described) to the cornea and/or gonioscope or gonioprism may help to achieve good optical contact. As the surgeon visualizes the trabecular meshwork, the cannula may then be advanced so that the bevel of at the distal end of the curved distal portion of the cannula pierces the meshwork and is in communication with the lumen of Schlemm's canal. Next, a slidable conduit coaxially disposed within the cannula lumen may be advanced into the canal under gonioscopic visualization. The slidable conduit may be advanced any suitable amount and direction about the canal. For example, the slidable conduit may be advanced between about 10 degrees to about 360 degrees about the canal, or it may be advanced in two steps, e.g., 180 degrees in a clockwise direction and 180 degrees in a counterclockwise direction about the canal (to thereby achieve a full 360 degree ab-interno viscocanalostomy or canaloplasty). Fluid may be injected upon advancement or retraction of the conduit. Once the slidable conduit has been positioned within the canal, a fluid composition, e.g., a viscoelastic solution, may be continuously or intermittently delivered through the conduit. The fluid composition may exit the conduit through its distal end (e.g., the through the distal tip), or through openings or fenestrations provided along its shaft, or a combination of both. The openings or fenestrations may be spaced along the axial length of the conduit in any suitable manner, e.g., symmetrically or asymmetrically along its length. Other substances such as drugs, air, or gas may delivered be in the same manner if desired.

The slidable conduit may be repositioned by retraction or repeated advancement and retraction. In some variations of the method, the same or different incision may be used, but the delivery system cannula is employed to access and dilate Schlemm's canal from a different direction (e.g., counterclockwise instead of clockwise). Once a sufficient amount of fluid has been delivered, the surgeon may retract the slidable conduit into the cannula and remove the delivery system from the eye. It should be understood that these steps may be used alone or in combination with cataract surgery (in one sitting).

Other variations of the ab-interno method for delivering a fluid composition include the use of an endoscope. Similar to the method described directly above, access to the anterior chamber is first made by incising the cornea, limbus, or sclera. Again, this may be done in combination with cataract surgery in one sitting, either before or after cataract surgery, or independently. The anterior chamber may be infused with saline solution or a viscoelastic composition may be placed in the anterior chamber to prevent its collapse. The saline or viscoelastic may be delivered as a separate step or it may be infused with the conduit of the delivery system, a sleeve on the conduit, or with a separate infusion cannula. The surgeon, under direct microscopic visualization, then advances the endoscope through the incision and towards the angle and trabecular meshwork. As the surgeon visualizes the trabecular meshwork via the endoscope or any associated display, the bevel of the cannula is advanced to pierce the meshwork. The slidable conduit is then advanced under endoscopic visualization. The slidable conduit may be advanced any suitable amount and direction about the canal. For example, the slidable conduit may be advanced between about 10 degrees to about 360 degrees about the canal, or it may be advanced in two steps, e.g., 180 degrees in a clockwise direction and 180 degrees in a counterclockwise direction about the canal (to thereby achieve a full 360 degree ab-interno viscocanalostomy). Once the slidable conduit has been positioned within the canal, a fluid composition, e.g., a viscoelastic fluid, may be continuously or intermittently delivered through the conduit. The fluid composition may exit the conduit through its distal end (e.g., the through the distal tip), or through openings or fenestrations provided along its shaft, or a combination of both. The openings or fenestrations may be spaced along the axial length of the conduit in any suitable manner, e.g., symmetrically or asymmetrically along its length. Other substances such as drugs, air, or gas may be delivered in the same manner if desired.

The slidable conduit may be repositioned by retraction or repeated advancement and retraction. In some variations of the method, the same or different incision may be used, but the delivery system cannula is employed to access and dilate Schlemm's canal from a different direction (e.g., counterclockwise instead of clockwise). Once a sufficient amount of fluid has been delivered, the surgeon may retract the slidable conduit into the cannula and remove the delivery system from the eye.

An ab-externo approach to implanting an ocular device or delivering a fluid composition may include additional or slightly different steps. For example, the creation of tissue flaps, suturing, etc., may be part of the ab-externo method. In general, the ab-externo method for implanting an ocular device may include the following steps. First, under microscopic visualization, conjunctiva is incised, a scleral flap is created and tissue is dissected to identify the ostia into Schlemm's canal. The anterior chamber may be separately infused with saline or may have a viscoelastic composition placed in it to prevent collapse of the anterior chamber angle. The operation may be done as a standalone procedure or in combination with cataract surgery in one sitting. It may also be done before the cataract surgery portion or after it.

Using the delivery system described herein, the cannula may be advanced into Schlemm's canal and the ocular device advanced using the positioning element under direct microscopic visualization or through a gonioscope or gonioprism. When the ocular device is advanced the desired amount, the surgeon may release the ocular device from the positioning element by actuating the engagement mechanism and remove the delivery system from the eye and operating field. The scleral wound is then closed, using for example, sutures or tissue adhesive. If repositioning of the ocular device is needed or desired, the surgeon may retract and/or advance the ocular device using the positioning element of the delivery system.

With respect to the delivery of a fluid composition, the ab-externo method is similar to ab-interno delivery. However, instead of using a positioning element, the delivery system employs a slidable conduit to infuse a fluid composition into Schlemm's canal. First, under microscopic visualization, conjunctiva is incised, a scleral flap is created and tissue is dissected to identify the ostia into Schlemm's canal. The anterior chamber may be separately infused with saline or may have a viscoelastic composition placed in it to prevent collapse of the anterior chamber angle. The operation may be done as a standalone procedure or in combination with cataract surgery in one sitting. It may also be done before the cataract surgery portion or after it.

Using the delivery system described herein, the cannula may be advanced into Schlemm's canal and a slidable conduit coaxially disposed within the cannula lumen may be advanced into the canal under gonioscopic visualization. Once the slidable conduit has been positioned within the canal, a fluid composition, e.g., a viscoelastic fluid, may be continuously or intermittently delivered through the conduit. The fluid composition may exit the conduit through its distal end (e.g., the through the distal tip), or through openings or fenestrations provided along its shaft, or a combination of both. The openings or fenestrations may be spaced along the axial length of the conduit in any suitable manner, e.g., symmetrically or asymmetrically along its length. Other substances such as drugs, air, or gas may delivered be in the same manner if desired. The slidable conduit may be repositioned by retraction or repeated advancement and retraction. The delivery system may then be removed from the eye.

The fluid compositions may be delivered in a manner where retraction of a system component allows advancement of the fluid out of the system cannula. Referring again to FIGS. 23A-23C, linear gear 1108 is retracted in the direction of the arrow (FIG. 23B) so that reservoir 1102 becomes pressurized. Retraction can be accomplished by rotation of pinion gear mechanisms 1120. Once a sufficient amount of pressure has been created in the reservoir 1102 the fluid composition contained therein is injected through linear gear lumen 1114 and conduit 1118 into Schlemm's canal. It should be understood that the ocular delivery systems may be configured so that the fluid compositions are delivered continuously, passively, automatically, or actively by the surgeon. The fluid compositions may also be delivered to the canal independent of the gear shaft movement with a pump or auxiliary plunger.

The fluid compositions that may be delivered by the ocular systems described herein include saline and viscoelastic fluids. The viscoelastic fluids may comprise hyaluronic acid, chondroitin sulfate, cellulose, derivatives or mixtures thereof, or solutions thereof. In one variation, the viscoelastic fluid comprises sodium hyaluronate. In another variation, the viscoelastic composition may further include a drug. For example, the viscoelastic composition may include a drug suitable for treating glaucoma, reducing or lowering intraocular pressure, reducing inflammation or scarring, and/or preventing infection. The viscoelastic composition may also include agents that aid with visualization of the viscoelastic composition. For example, dyes such as but not limited to fluorescein, trypan blue, or indocyanine green may be included. In some variations, a fluorescent compound or bioluminescent compound is included in the viscoelastic composition to help with its visualization. In other variations, the system delivers the drug alone, without the viscoelastic composition. In this case, the drug may be loaded onto or into a sustained release biodegradable polymer that elutes drug over a period of weeks, months, or years. It is also contemplated that air or a gas could be delivered with the systems.

The fluid compositions may be delivered to dilate Schlemm's canal. The entire length of Schlemm's canal or a portion thereof may be dilated by the fluid. For example, at least 75%, at least 50%, at least 25%, or at least 10% of the canal may be dilated. The fluid compositions may also be delivered to treat various medical conditions, including but not limited to, glaucoma, pre-glaucoma, and ocular hypertension.

Additionally, the fluid compositions may be delivered to restore the tubular anatomy of Schlemm's canal, to clear obstructions within the canal, to disrupt juxtacanalicular trabecular meshwork or the inner wall of Schlemm's canal within the canal, or to expand the canal. Here the delivery systems may include wires, tubes, balloons, instruments that deliver energy to the tissues, and/or other features to help with these methods. It is contemplated that glaucoma may be treated using such systems with additional features. The surface of these systems may also be roughened or have projections to further disrupt the inner wall of Schlemm's canal and juxtacanalicular trabecular meshwork to enhance aqueous humor outflow or permeability.

When the systems and devices are tailored to provide a disruptive force to the trabeculocanalicular tissues, implant-free methods may be employed, e.g., by delivering a disruptive volume of viscoelastic fluid, advancing disruptive tools, e.g., cannulas, conduits, catheters, etc., including one or more disruptive components on their distal portions, or both. Exemplary disruptive components include, without limitation, notches, hooks, barbs, or combinations thereof. Depending on factors such as the type or severity of the condition being treated, the disruptive force may be generated to partially or completely destroy and/or remove the trabecular meshwork, and may be adjusted by varying the volume of viscoelastic fluid delivered, or by varying the tool configuration. Exemplary volumes of viscoelastic fluid that may be sufficient to provide a disruptive force may range from about 1 µl to about 50 µl, from about 1 µl to about 30 µl, or from about 2 µl to about 16 µl. In one variation, a volume of about 4 µl is sufficient to disrupt Schlemm's canal and/or the surrounding tissues. In other variations, the volume of viscoelastic fluid sufficient to disrupt trabeculo-canalicular tissues may be about 2 µl, about 3 µl, about 4 µl, about 5 µl, about 6 µl, about 7 µl, about 8 µl, about 9 µl, about 10 µl, about 11 µl, about 12 µl, 13 µl, about 14 µl, about 15 µl, about 16 µl, about 17 µl, about 18 µl, about 19 µl, about 20 µl, about 25 µl, about 30 µl, about 35 µl, about 40 µl, about 45 µl, or about 50 µl. The total volume of viscoelastic fluid may be delivered along a 360 degree arc 1600 of Schlemm's canal during a single advancement from a single access point 1602 in the canal (e.g., as shown in FIG. 28) or withdrawal of the conduit 1604, or along lesser degrees of arc in multiple advancements or withdrawals of the conduit.

Figures 28, 29, 30A:
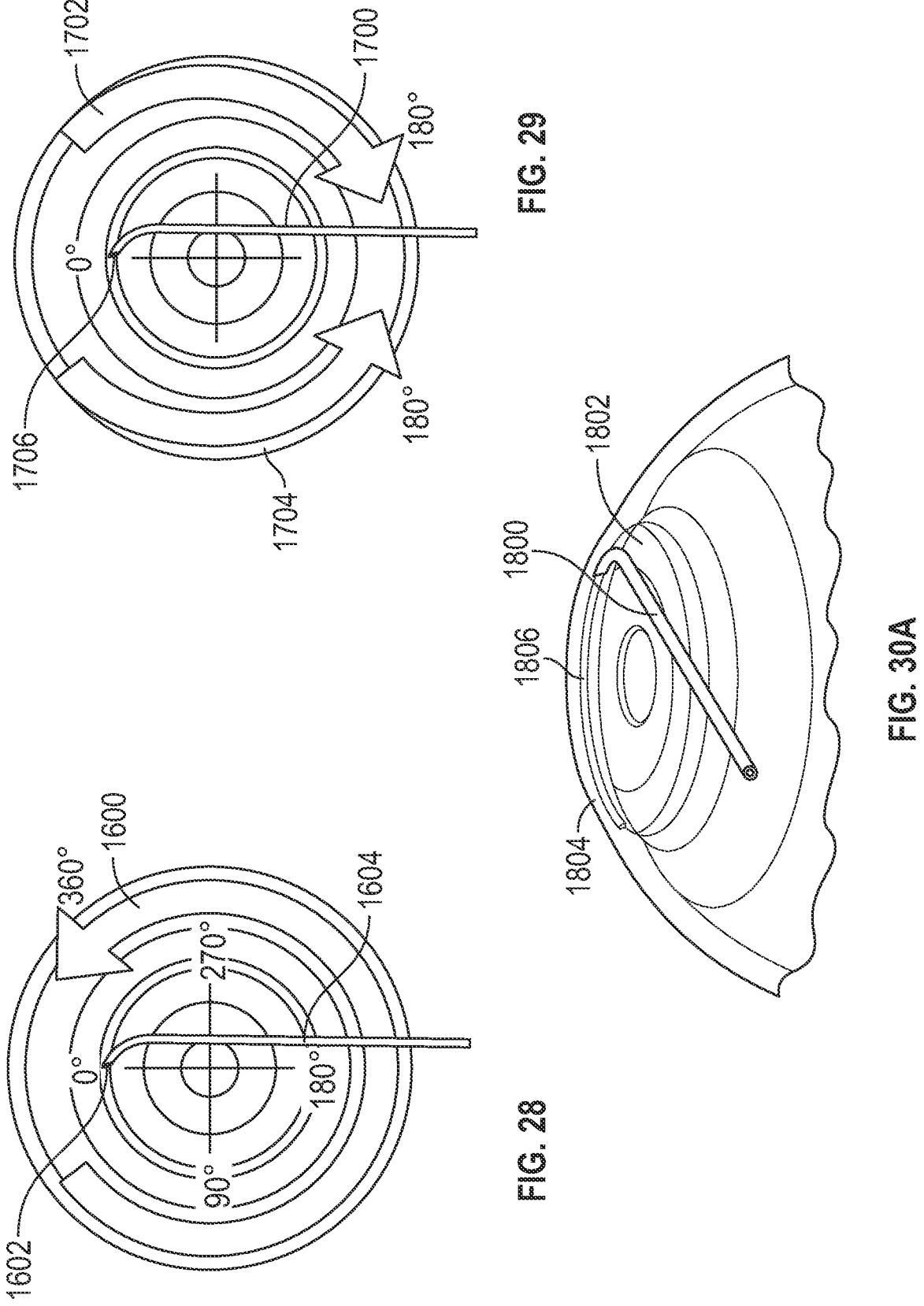
FIG. 28 depicts a stylized depiction of an ab-interno method of accessing Schlemm's canal from a single point, and delivering a viscoelastic fluid while advancing a fluid delivery conduit along a 360 degree arc of the canal.
FIG. 29 depicts a stylized depiction of an ab-interno method of accessing Schlemm's canal from a single point, and delivering a viscoelastic fluid while advancing a fluid delivery conduit in both the clockwise and counterclockwise directions along a 180 degree arc of the canal.
FIGS. 30A-30C depict an exemplary ab-interno method of cutting or tearing the trabecular meshwork.

For example, as shown in FIG. 29, a conduit 1700 may be advanced along a 180 degree arc of the canal in both clockwise 1702 and counterclockwise 1704 directions to deliver fluid from, e.g., a single access point 1706 in the canal. Referring to FIGS. 28 and 29, an exemplary disruptive volume of, 4 µl may be delivered along a 360 degree arc of the canal while the conduit is advanced from a single access point in the canal, or 2 µl may be delivered along a 180 degree arc of the canal during two advancements (one in the clockwise direction and the other in the counterclockwise direction) of the conduit from a single access point in the canal. The conduit may access the canal from a single point or from multiple points. The amount or degree of tissue disruption may be varied by the volume of fluid delivered. For example, 8 µl may be used to perforate or gently tear the meshwork, while 16 µl may be used to maximally tear the meshwork. More specifically, about 1 to 2 µl may be used to dilate Schlemm's canal and collector channels; about 2 to 4 µl may be used to dilate Schlemm's canal and collector channels, and disrupt/stretch juxtacanalicular tissues; and about 4 to 6 µl may be used for all the foregoing and for the creation of microtears in the trabecular meshwork and juxtacanalicular tissues (further increasing porosity and outflow). A volume of about 8 to 16 µl may be used for all the foregoing and for substantial perforation/tearing of the trabecular meshwork and juxtacanalicular tissues. A volume of about 16 to 50 µl may be used for substantial or complete tearing of the trabecular meshwork. When fluids are not used, and only a disruptive tool is employed, the outer diameter of the conduit or tool may be variously sized for disruption of tissues, analogous to how fluid volumes may be varied to vary the level of disruption.

For example, a conduit or tool having an outer diameter ranging from about 50 to about 100 microns may be advanced through the canal to slightly dilate the canal and break or remove septae obstructing circumferential canalicular flow. A conduit or tool having an outer diameter ranging from about 100 to 200 microns may be employed to perform the foregoing, and may also to begin to stretch the trabecular meshwork and juxtacanalicular tissues. A conduit or tool having an outer diameter ranging from about 200 to about 300 microns may be able to perform the above, but may also create microtears in the trabecular meshwork and juxtacanalicular tissues, and may maximally dilate the collector channels. A conduit or tool having an outer diameter ranging from about 300 to about 500 microns may maximally disrupt the tissues and may create tears or perforations all along the trabecular meshwork and juxtacanalicular tissues. Additionally, the further the advancement of the conduit or tool through the canal, the greater the efficacy of the procedure. For example, the conduit or tool may be advanced out from the tip of the cannula and into the canal about a 30 degree arc of the canal (e.g., advanced about 3 to 4 mm out of the cannula), advanced about a 60 degree arc of the canal (e.g., advanced about 6 to 8 mm out of the cannula), advanced about a 90 degree arc of the canal (e.g., advanced about 10 mm out of the cannula), advanced about a 120 arc of the canal (e.g., advanced about 15 mm out of the cannula), advanced about a 180 degree arc of the canal (e.g., advanced about 20 mm out of the cannula), or advanced about a full 360 degrees of the canal (e.g., advanced about 36 to 40 mm out of the cannula), for maximal efficacy and maximal intraocular pressure reduction.

The implant-free methods for treating conditions of the eye may include advancing a conduit into Schlemm's canal, where the conduit has been loaded with a volume of viscoelastic fluid, and delivering the viscoelastic fluid into Schlemm's canal at a volume sufficient to disrupt the trabeculocanalicular tissues to reduce intraocular pressure. However, the implant-free methods for treating conditions of the eye may not necessarily include delivery of viscoelastic fluids. In these instances, the method may comprise advancing a device into Schlemm's canal, where the device has a diameter between about 300 and about 500 microns, or about 150 and about 200 microns, and where advancement of the device into Schlemm's canal disrupts the canal and/or trabeculocanalicular tissues in a manner sufficient to reduce intraocular pressure.

Other methods for treating conditions of the eye may be single-handed, single-operator methods for introducing viscoeleastic fluid into Schlemm's canal that include advancing a conduit into Schlemm's canal, where the conduit has been loaded with a volume of viscoelastic fluid, and delivering the viscoelastic fluid into Schlemm's canal, where delivering the volume of viscoelastic fluid is accomplished by a single-handed device used by a single operator.

Again, when viscoelastic fluids are delivered in the methods disclosed herein, the disruptive volume may be between about 2 µl to about 8 µl. It may be beneficial to deliver a volume of about 4 µl of viscoelastic fluid in certain instances. The viscoelastic fluid may be delivered while advancing the conduit of a single-handed, single-operator controlled device from Schlemm's canal in the clockwise direction, counterclockwise direction, or both, or during withdrawal of the conduit from Schlemm's canal. As previously stated, the viscoelastic fluid may be delivered to disrupt Schlemm's canal and surrounding trabeculocanalicular tissues. For example, the delivered viscoelastic fluid may cause disruption by dilating Schlemm's canal, increasing the porosity of the trabecular meshwork, stretching the trabecular meshwork, forming microtears in juxtacanalicular tissue, removing septae from Schlemm's canal, dilating collector channels, or a combination thereof. The conduit may be loaded with the viscoelastic fluid at the start of an ocular procedure so that the fluid can be delivered by a single device. This is in contrast to other systems that use forceps or other advancement tool to advance a fluid delivery catheter into Schlemm's canal and/or devices containing viscoelastic fluid that are separate or independent from a delivery catheter or catheter advancement tool, and which require connection to the delivery catheter or catheter advancement tool during a procedure by an assistant while the delivery catheter or catheter advancement tool is held by the surgeon.

In some variations, the methods disclosed herein may include advancement of the conduit (or a tool) about a 360 degree arc of Schlemm's canal, about a 270 degree arc of Schlemm's canal, about a 120 degree arc of Schlemm's canal, about a 180 degree arc of Schlemm's canal, or about a 90 degree arc of Schlemm's canal. In yet further variations, advancement of the conduit (or a tool) may be about a 0 to 5 degree arc of Schlemm's canal, about a 30 degree arc of Schlemm's canal, or about a 60 degree arc of Schlemm's canal. Advancement may occur from a single access point in Schlemm's canal or from multiple access points in the canal. When a disruptive force is to be provided, it may be beneficial to advance the conduit in both clockwise and counterclockwise directions about a 180 degree arc of Schlemm's canal from a single access point in the canal.

Prior to the introduction of goniotomy and trabeculotomy (both of which are typically used to treat an obstructed trabecular meshwork, often genetically-driven at a young age), congenital glaucoma uniformly resulted in blindness. Despite the invasiveness of goniotomy (which is performed ab-interno, but a sharp scalpel is used to cut 30-60 degrees of meshwork to improve outflow) and trabeculotomy (ab-externo method where deep scleral incisions unroof Schlemm's canal and the meshwork is cut with a probe), the procedures are viewed as being effective and have allowed many pediatric patients to avoid an entire lifetime of blindness. In 1960, Burian and Smith each independently described trabeculotomy ab-externo. In this highly invasive ab-externo operation, the surgeon makes a deep scleral incision, finds Schlemm's canal, cannulates all 360 degrees of Schlemm's canal externally with a catheter or specially designed probe called a trabeculotome, and finally tensions both ends of the catheter or probe to the point where the trabeculotome cuts through the entire trabecular meshwork into the anterior chamber to improve drainage.

More recent attempts at decreasing the invasiveness of ab-externo trabeculotomy have been developed by NeoMedix, which commercializes a device called "Trabectome". The Trabectome attempts to make trabeculotomy easier by using an ab-interno approach. The instrument and methods involve removal of the trabecular meshwork ab interno by electrocautery using an instrument that also provides infusion and aspiration. The disadvantages of the Trabectome are three-fold: 1) the device employs an energy-based mechanism to ablate trabecular meshwork, which is believed to cause inflammation and scarring in the eye, which in turn can adversely impact outflow and pressure; 2) the device/procedure is ergonomically limited—it requires a foot pedal and power cords to activate electrocautery and irrigation in addition to being limited to 60-120 degrees of meshwork therapy per corneal or scleral entry incision; and 3) Because it involves energy-based ablation and irrigation, there is a significant capital equipment cost that may limit adoption.

The methods (as well as systems and devices) described herein, including the method for providing a disruptive force to trabeculocanalicular tissues, may be highly suitable for ab-interno trabeculotomy and goniotomy given that they avoid the use of electrocautery, and are capable of advancing conduits over larger degrees of arc of Schlemm's canal. In some variations of the ab-interno trabeculotomy and goniotomy methods, the procedure includes advancing a cannula at least partially through the anterior chamber of the eye, entering Schlemm's canal at a single access point using the cannula, and delivering a volume of a viscoelastic fluid through a conduit slidable within, and extendable from, the cannula, sufficient to disrupt the structure of Schlemm's canal and surrounding tissues to reduce intraocular pressure. Other methods that may be useful in treating conditions of the eye include the steps of entering Schlemm's canal using a conduit extendable from a single-operator controlled handle, the handle comprising a fluid reservoir, and delivering a volume of a viscoelastic fluid from the fluid reservoir through the conduit by increasing pressure within the fluid reservoir, where the volume of delivered viscoelastic fluid is sufficient to disrupt the structure of Schlemm's canal and surrounding tissues to reduce intraocular pressure. The disruptive volume may be between about 2 µl to about 16 µl. In one variation, the disruptive volume is about 4 µl of viscoelastic fluid. As previously stated, in some instances the disruptive volume may range anywhere between about 20 µl to about 50 µl.

More specifically, disruption (e.g., cutting, destruction, removal, etc.) of the trabecular meshwork may be accomplished by removing the cannula from the eye while leaving the conduit in the canal, thereby tearing through the meshwork. Alternatively, tissue disruption may occur by visco-dilating excessively and intentionally with at least about 1 µl, at least about 2 µl, at least about 3 µl, at least about 4 µl, at least about 5 µl, at least about 6 µl, at least about 7 µl, at least about 8 µl, at least about 9 µl, at least about 10 µl, at least about 11 µl, at least about 12 µl, at least about 13 µl, at least about 14 µl, at least about 15 µl, at least about 16 µl, at least about 17 µl, at least about 18 µl, at least about 19 µl, or at least about 20 µl of viscoelastic fluid per 360 degree arc of the canal. The amount or degree of tissue disruption may be varied by the volume of fluid delivered. For example, 8 µl may be used to perforate or gently tear the meshwork, while 16 µl may be used to maximally tear the meshwork. In some variations, at least about 20 µl, at least about 25 µl, at least about 30 µl, at least about 35 µl, at least about 40 µl, at least about 45 µl, or at least about 50 µl of viscoelastic fluid may be delivered.

Another method for disrupting tissues may include using oversized conduits (e.g., having an outside diameter of 300-500 microns) to tear the meshwork upon delivery, or inflating or expanding the conduit once it has been fully advanced into Schlemm's canal to stretch, disrupt, rupture, or fully tear the meshwork. For example, a catheter/conduit, probe, or wire (with or without a lumen) whose tip is 200-250 microns in outer diameter, but having a shaft that begins to flare outwards after 3 clock hours of Schlemm's canal (i.e., at about the 5 or 10 mm mark on the catheter/conduit) up to about 300, up to about 400, or up to about 500 microns, may be used, so that as the tip advances comfortably within Schlemm's canal, the enlarged shaft trails behind and ruptures the trabecular meshwork as it is advanced.

In yet further methods, tissue disruption may be accomplished by the ab-interno delivery of a suture throughout Schlemm's canal, which is then sufficiently tensioned to stretch the canal, disrupt the trabecular meshwork, and/or tear through the meshwork ("Ab interno Suture Trabeculotomy"). Here a tool including a grasping element may be employed for pulling the distal suture tip inwards as the cannula is being withdrawn from the eye, severing all 360 degrees or a segment of the trabecular meshwork, or for tying the suture ends together to provide tension on the meshwork without necessarily tearing it.

Figure 30B:
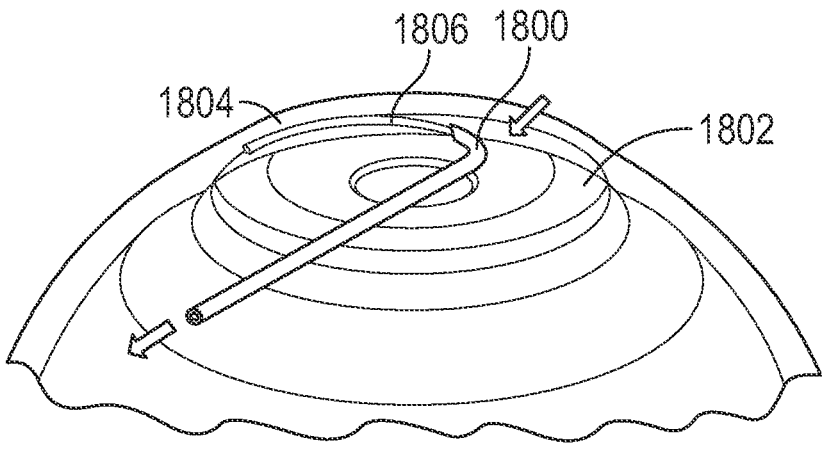
Figure 30C:
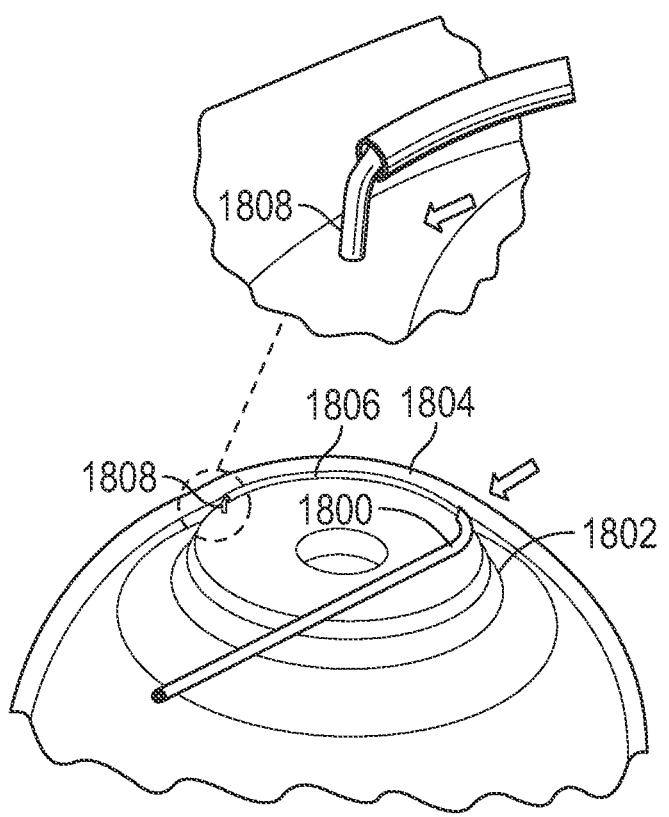

Customizing a body segment of the conduit proximal to the tip with a notch or notches or barbs that catch the meshwork as the distal tip is being guided and advanced along Schlemm's canal could also be used, thereby disrupting, partially tearing, fully tearing, and/or removing trabecular meshwork upon advancement. Additionally, an implant with edges specifically designed to cut the meshwork could be used. Still other methods for disrupting tissues may involve customizing the system (e.g., the conduit, any catheters or wires, probe tips, etc.) to catch or grasp the meshwork upon retraction after complete advancement through the canal. This may be done using a wire with a bent tip, hook, notch, or barb on its end that is advanced through the lumen of the catheter that then snags the meshwork upon retraction, tearing it along its length or removing it altogether, or solely with a metal or polymer wire or suture (no catheter) whose tip (and/or body) is hooked, notched, or barbed in such a way that it can be advanced into Schlemm's canal without tearing the meshwork but snags the meshwork upon retraction, tearing the meshwork and/or removing it completely. Referring to FIG. 30A, a cannula 1800 may be inserted into the anterior chamber 1802 and Schlemm's canal 1804, and a tool (e.g., a slidable conduit 1806 may be advanced within the canal 1804. As shown in FIG. 30B, the cannula 1800 can be withdrawn from the anterior chamber 1802 without retracting the slidable conduit 1806. This action by itself may tear the trabecular meshwork. Alternatively, as shown in FIG. 30C, the conduit 1806 may be provided with a disruptive tool, e.g., a sharp-edged element 1808, that can cut or tear the trabecular meshwork while being retracted into the cannula 1800, which is held stationary. Exemplary sharp-edged elements may be a hook, wire, or any other suitable shape memory component that can extend from the cannula to tear, cut, or remove trabecular meshwork.

The configuration of the ocular delivery system may be advantageous in many different respects. In one aspect, the delivery system is capable of being used in an ab-interno method of implanting an ocular device in Schlemm's canal or an ab-interno method of delivering a fluid composition or a tool into the canal. In another aspect, the delivery system cannula is configured to allow easy and atraumatic access to Schlemm's canal. Furthermore, the delivery system is configured in a manner that gives the surgeon greater freedom of use, all in a single instrument. For example, the handle of the system is configured so that it can be used with either the right or left hand on either the right or left eye just by flipping over the handle or rotating the cannula. Furthermore, the delivery system is designed so that it is capable of being used with the right hand to access Schlemm's canal in a counterclockwise fashion, use with the left hand to access to Schlemm's canal in a clockwise fashion, or use with the left hand to access the canal in a counterclockwise fashion, etc. Thus, access to the canal from all four quadrants of the eye can be achieved. In yet a further respect, the delivery system comprises single-handed, single-operator controlled devices configured to provide a force sufficient to disrupt Schlemm's canal and surrounding tissues to improve flow through the trabeculocanalicular outflow pathway. The systems generally combine access cannulas, delivery conduits, conduit advancement mechanisms, disruptive tools, and viscoelastic fluids into a single device so that one person or one hand can advance the conduit or tool, or deliver the fluid.

Figure 31A:
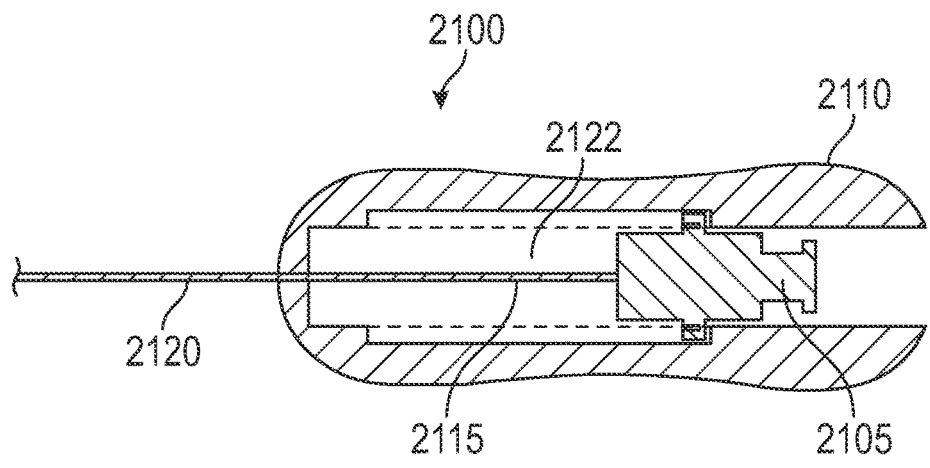
FIGS. 31A-31B depict top views of an embodiment of a cannula adapter in an un-deployed configuration and a fully deployed configuration, respectively.
Figure 31B:
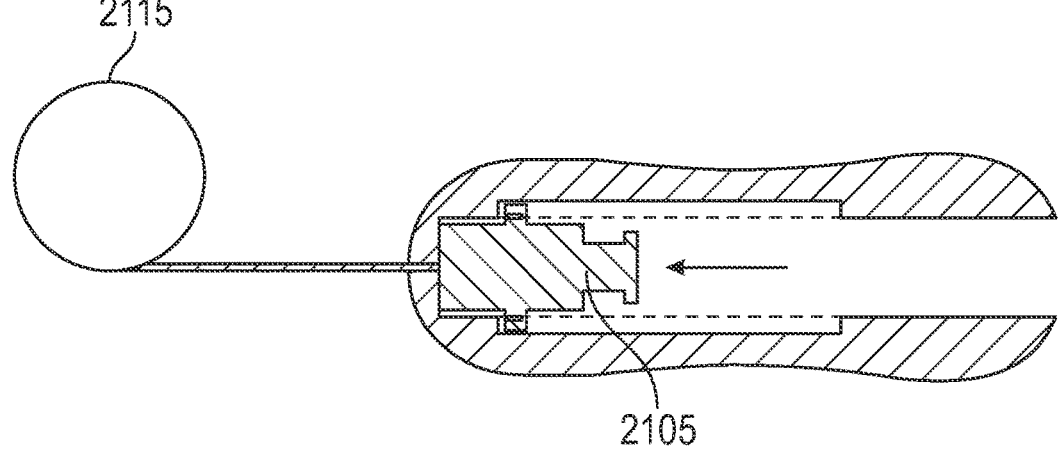

FIGS. 31A and 31B schematically illustrate top views of an embodiment of a cannula adapter 2100 in an undeployed configuration and a deployed configuration, respectively. The cannula adapter 2100 includes a connector 2105, a housing 2110, an inner catheter 2115, and an outer cannula 2120.

The connector 2105 (e.g., standard Luer connector) may be adapted to slide along a restricted axial range within the housing 2110 of the cannula adapter 2100. The connector 2105 may also be restricted from azimuthal rotation. The inner catheter 2115 may comprise a flexible lumen that is introduced through Schlemm's canal and that is fluidically coupled to a distal end of the sliding connector 2105. The lumen of the inner catheter 2115 may extend from a proximal end to a distal end of the inner catheter 2115. The inner catheter 2115 may be adapted to fit within and extend through a lumen of the outer cannula 2120 such that a distal tip of the inner catheter 2115 and a distal tip of the outer cannula 2120 are aligned when the sliding connector 2105 is in a proximal-most position, such as in the undeployed configuration shown in FIG. 31A.

The proximal end of the outer cannula 2120 can be coupled to the distal end portion of the housing 2110 (and to a distal end of a sliding channel 2122 of the housing within which the connector 2105 translates axially). When the connector 2105 is in a distal-most position (such as in the fully-deployed configuration shown in the FIG. 31B when the connector 2105 has been pressed forward until the sliding channel 2122 within the housing 2110 ends), the distal tip of the inner catheter 2115 can extend past the distal tip of the outer cannula 2120 to a predetermined distance. In some implementations, the predetermined distance can be approximately equal to the circumference (e.g., 360 degrees) of Schlemm's canal. The length of the portion of the inner catheter 2115 that is extended out of the distal tip of the outer cannula 2120 when the connector 2105 is in a distal-most position within the sliding channel 2122 of the housing 2110 may be configured to have a length corresponding to a value in an upper range (e.g., a maximum known value) of a circumference of Schlemm's canal of a human or other mammal or a length corresponding to a mean or median value.

The distal portion (e.g., at least the portion that extends past the including the distal tip) of the inner catheter 2115 may be pre-shaped (e.g., shape set using shape memory material such as copper-aluminum-nickel alloy or nickel-titanium alloy) to follow approximately a radius of curvature of Schlemm's canal (e.g., a predetermined median or mean value), or may be made of material flexible enough to bend along an outer wall of Schlemm's canal (e.g., polyvinyl-chloride, polyetheretherketone, polyethylene, polytetrafluoroethylene, thermoplastic polyurethane, polyamide, polyimide, polymethyl methacrylate (PMMA), acrylonitrile butadiene styrene, silicone, and/or other sufficiently flexible material).

Figure 31C:
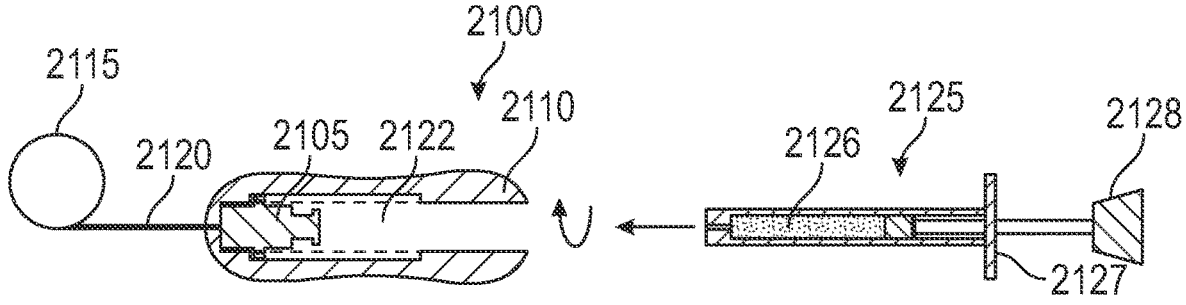
FIGS. 31C-31D depict an example of how the cannula adapter of FIG. 31A is attached to a standard ophthalmic viscosurgical device, such as an ophthalmic viscoelastic syringe.
Figure 31D:
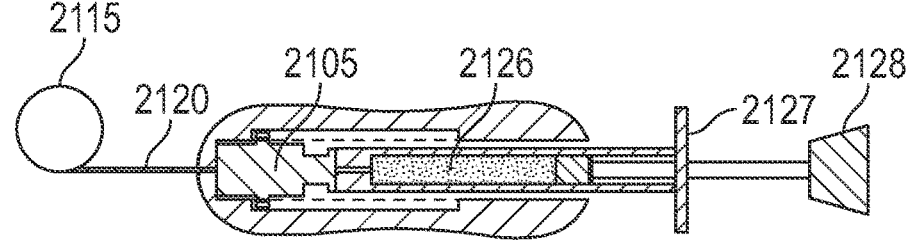

The cannula adapter 2100 of FIGS. 31A and 31B may be adapted for use with any standard "off-the-shelf" or commercially-available ophthalmic viscosurgical device (OVD) or other viscoelastic delivery device, such as the HEALON® viscoelastic syringes made available commercially by Johnson & Johnson. For example, a pre-filled ophthalmic viscoelastic device (e.g., syringe) 2125 can be inserted into the proximal end of the housing 2110 and rotated to rigidly lock with the sliding connector 2105 as shown in FIG. 31C. As an example of use, an operator (e.g., clinician or medical practitioner) can hold the housing 2110 with one hand and use the other hand to translate the syringe 2125 forward (e.g., distally, or toward a patient) relative to the housing 2110 (e.g., by pressing on a proximal stop 2127 of the syringe 2125) to extend the inner catheter 2115 (e.g., via translation of the sliding connector 2105) out of the outer cannula 2120, and then plunge the syringe 2125 (e.g., by pressing on a proximal plunger actuator 2128 of the syringe 2125 as shown in FIG. 31D) to deliver a desired amount of fluid 2126 (e.g., viscoelastic or other ophthalmic viscosurgical device (OVD) fluid). The desired amount may be patient-specific or location specific and may be determined by the operator as desired and/or required.

Figure 31E:
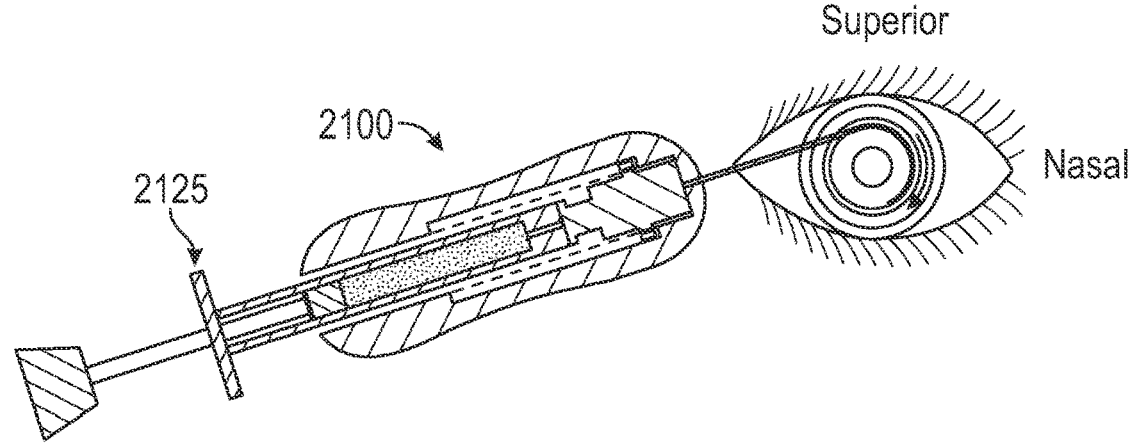
FIGS. 31E-31F depict an example of a surgical implementation of access and insertion of the cannula adapter of FIG. 31A.
Figure 31F:
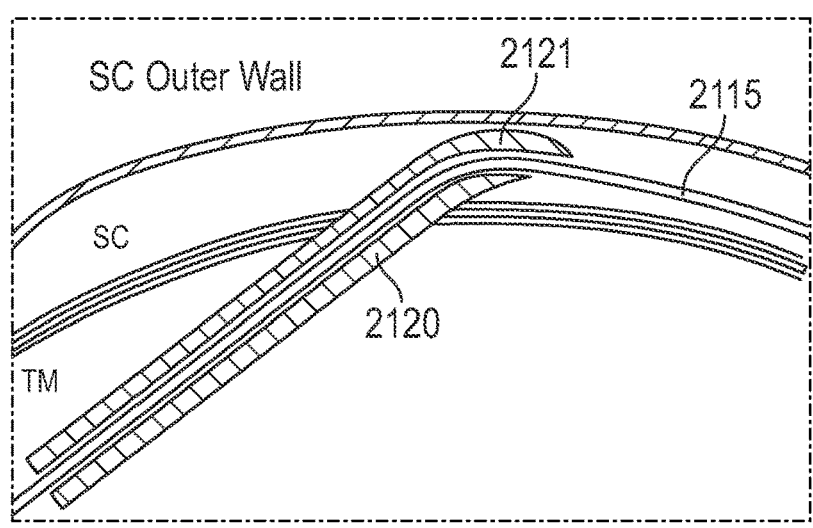
Figure 31G:
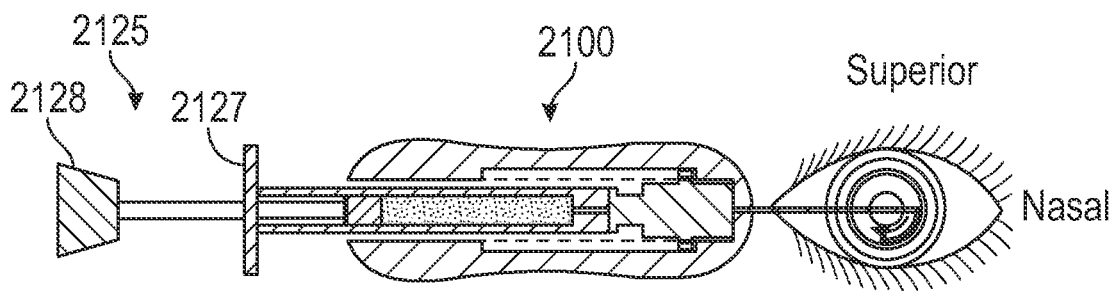
FIGS. 31G-31H depict another example of a surgical implementation of access and insertion of the cannula adapter of FIG. 31A.
Figure 31H:
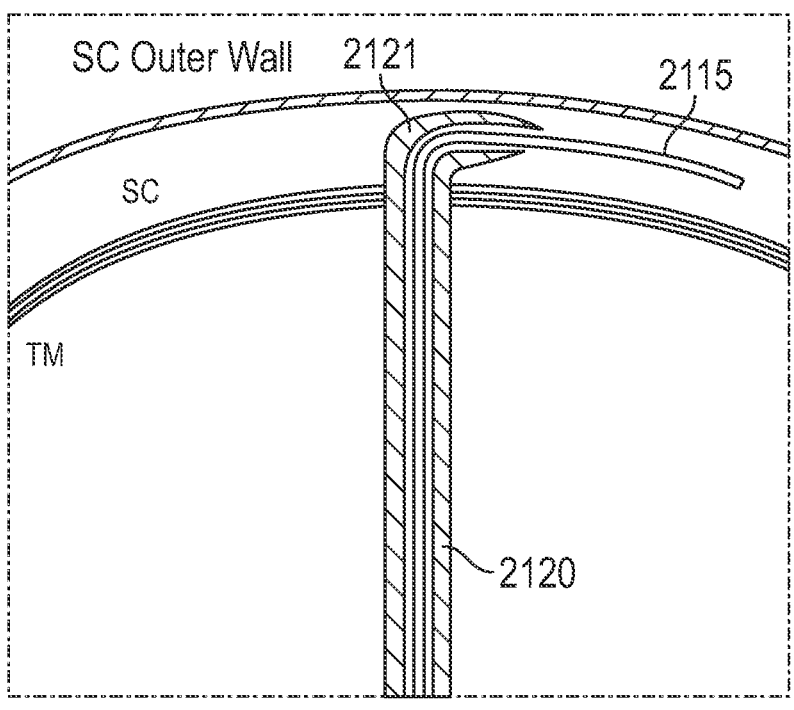

The outer cannula 2120 can be adapted to be inserted through a minimally-invasive, temporal, clear corneal incision. The corneal incision may be sized so as to be self-sealing without requiring sutures. FIG. 31E illustrates one example method of surgical insertion using a superior insertion approach. As illustrated, a distal portion 2121 of the outer cannula 2120 may be shaped (e.g., a scoop with a sharpened tip) so as to facilitate penetration of a superior trabecular meshwork (TM) portion and guide the inner catheter 2115 360 degrees into Schlemm's canal (SC) as shown in FIG. 31F. Alternatively, the distal tip of the outer cannula 2120 may be inserted using a nasal insertion approach through the nasal trabecular meshwork, as shown in FIGS. 31G and 31H.

In some implementations, such as when using a nasal insertion approach, the inner catheter 2115 may be adapted to be advanced through a first 180 degrees of Schlemm's canal and then through a remaining 180 degrees of Schlemm's canal. For example, a distal portion 2121 of the outer cannula 2120 may be inserted into Schlemm's canal through the trabecular meshwork in such a manner that the inner catheter 2115 may be advanced through a first 180 degrees of Schlemm's canal from the insertion location into Schlemm's canal. The inner catheter 2115 may then be retracted and the distal tip 2121 of the outer cannula 2120 may be rotated, or removed from Schlemm's canal and reinserted, in a manner such that the remaining 180 degrees of Schlemm's canal may be traversed by the inner catheter 2115 in an opposite direction from the entry point. The distal tip 2121 of the outer cannula 2120 may be pre-curved or may be sufficiently flexible to bend upon contact with an outer wall of Schlemm's canal. If pre-curved, the distal tip of the outer cannula 2120 may have a different curvature or bend configuration depending on whether it is intended for a superior or nasal insertion approach. In some implementations, only a single 180 degree portion is treated.

Figure 31I:
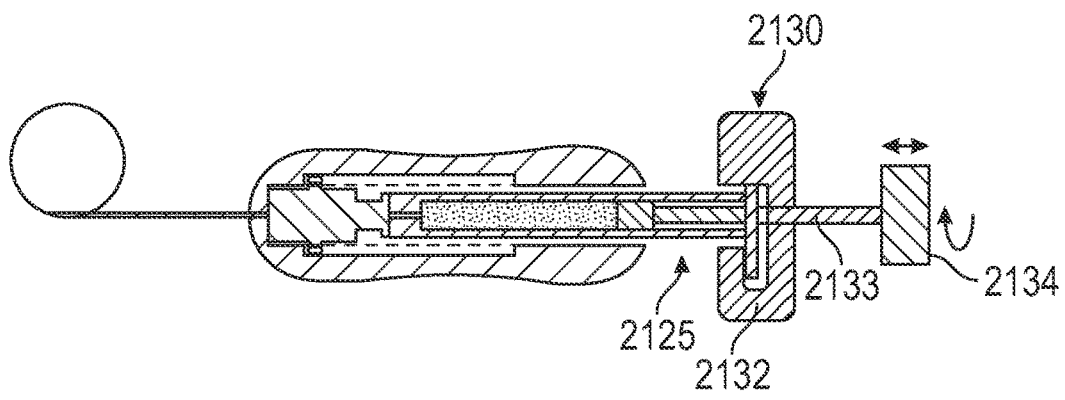

Turning to FIG. 31I, a fluid control adapter 2130 can be attached to a proximal end of the syringe 2125 to facilitate precisely controlled delivery of viscoelastic or other fluid (e.g., drug, chemical, solution, other liquid) in accordance with several embodiments. In such implementations, a plunger handle of the syringe 2125 may be removed. In the illustrated embodiment, the fluid control adapter 2130 comprises a dispenser attachment fitting 2132 that is adapted to be attached to the syringe 2125 like a common pneumatic adhesive dispenser (such as a pneumatic dispenser made commercially available by Nordson EFD). The attachment fitting 2132 may have a threaded thru-hole for receiving a complementary threaded "bolt-type" plunger driver 2133 and a rotatable knob 2134. Rotating the knob 2134 (and thereby the plunger driver 2133) clockwise can push the internal plunger of the syringe 2125, thus dispensing the fluid 2126 (e.g., viscoelastic or other OVD fluid). The sensitivity of the dispensing can be controlled by the pitch of the threading. The fluid control adapter 2130 can be rigidly connected to the syringe 2125 and therefore axial translation of the adapter 2130 (e.g., caused by axial translation of the knob 2134 from rotation of the knob 2134) can result in extension of the inner catheter 2115. The rotatable knob 2134 may optionally comprise a knurled head.

Figure 32A:
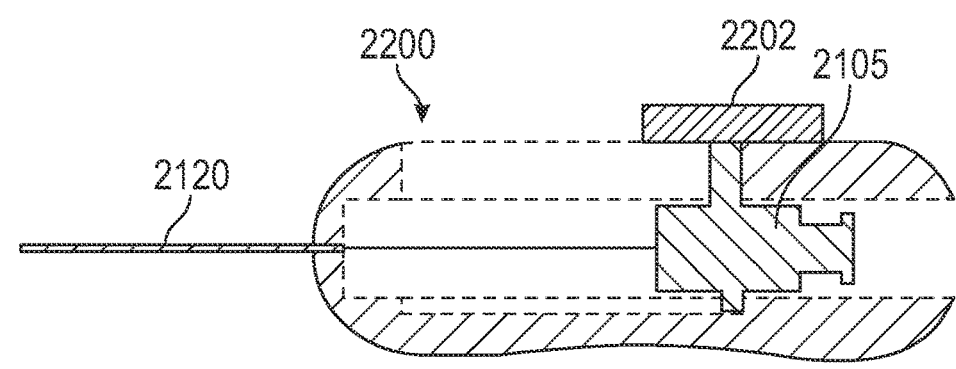
FIGS. 32A-32B depict side views of another embodiment of a cannula adapter with a sliding trigger in both an un-deployed configuration and a fully-deployed configuration.
Figure 32B:
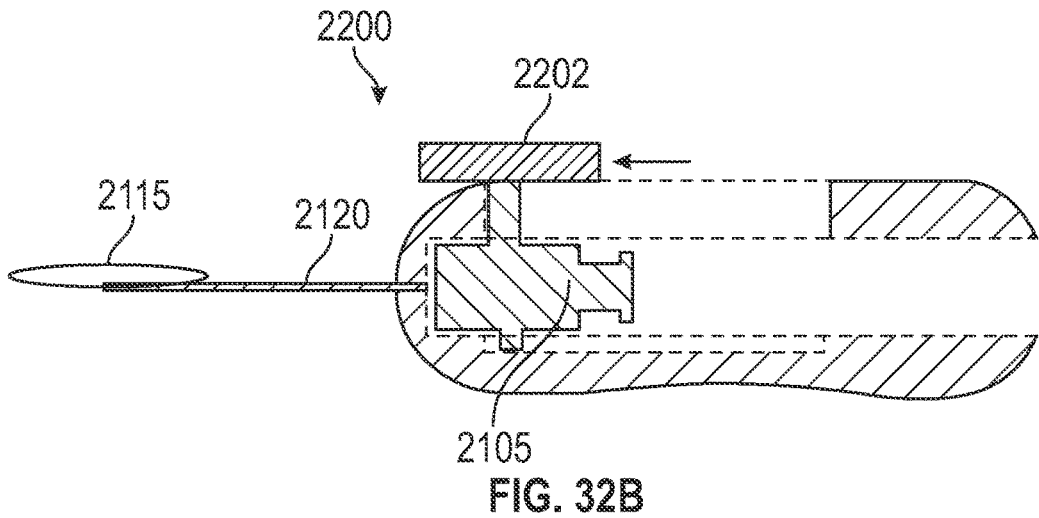

With reference to FIGS. 32A and 32B, a cannula adapter 2200 may be adapted or modified to include a sliding trigger 2202 that is rigidly attached to the internal sliding connector 2105 (e.g., a single molded part during manufacturing), and allowed to slide axially relative to the housing 2110. The operator can then simply extend the inner catheter 2115 via distal motion (i.e., motion toward a patient) of his or her finger or thumb instead of pressing on a proximal stop of the syringe 2125 (e.g., pressing on a proximal plunger actuator 2128 of the syringe 2125 as shown in FIG. 31D). An outer surface of the sliding trigger 2202 may have surface features (e.g., ridges, grooves, or the like) adapted to facilitate gripping or friction against a finger or thumb of the operator.

Figure 32C:
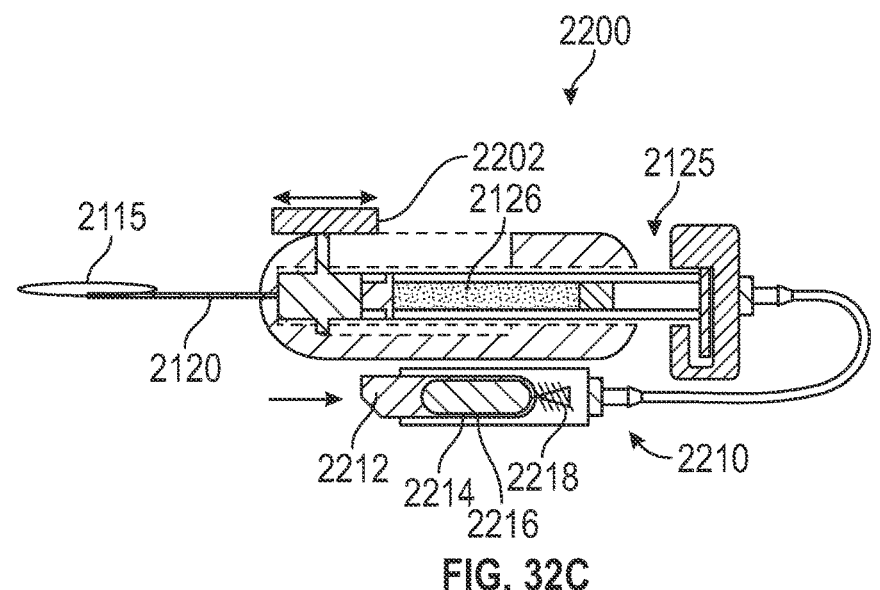
FIG. 32C depicts a side view of an adaptation of the embodiment of FIG. 32A that includes a coupler to facilitate pneumatic fluid delivery.

FIG. 32C illustrates a further modification or adaptation of the cannula adapter 2200 of FIGS. 32A and 32B that is adapted to allow for actuation of the inner catheter 2115 and dispensing of the viscoelastic or other fluid with a single hand of the operator. The illustrated embodiment can include the sliding trigger 2202 introduced in FIGS. 2A and 2B to extend the inner catheter 2115 and incorporates a pneumatic system 2210 adapted for pressurizing the viscoelastic syringe 2125. The pneumatic system 2210 is enlarged and illustrated in more detail with respect to its components and operation in FIGS. 32D and 32E.

Figure 32D:
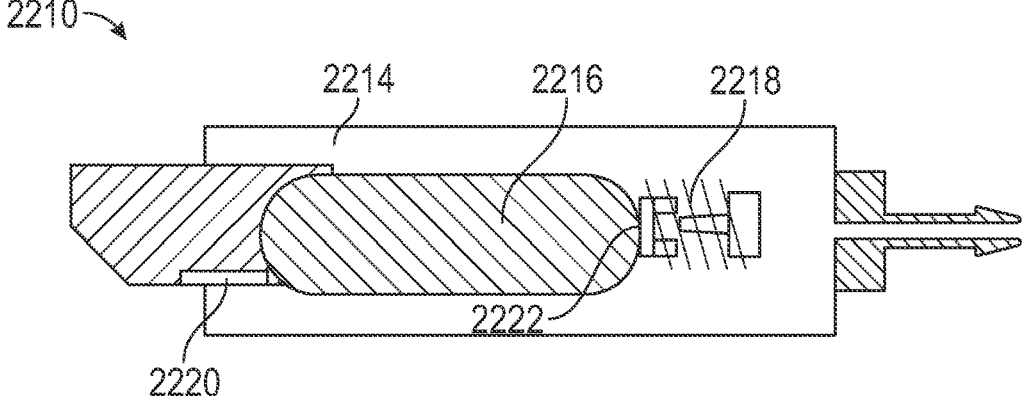
FIGS. 32D-32E depict an example embodiment of a pneumatic system adapted for use with the cannula adapter of FIG. 32C.
Figure 32E:
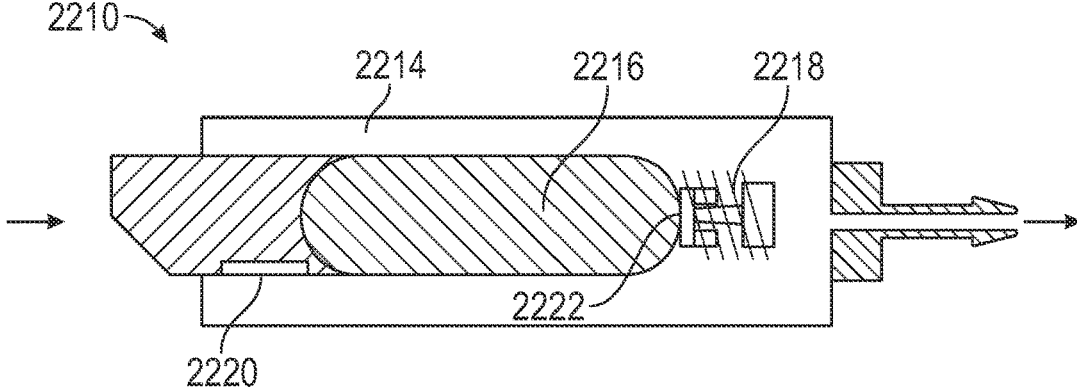

The pneumatic system 2210 can utilize a trigger 2212 that is adapted to be actuated by an operator's finger (e.g., index finger). FIG. 32D illustrates the pneumatic system 2210 before the trigger 2212 is depressed and FIG. 32E illustrates the pneumatic system 2210 after the trigger is depressed (e.g., pushed in a direction away from the patient to compress the spring 2218). Upon depression of the trigger 2212 (e.g., moves to its actuated position), a miniature, valve-release pressurized cartridge 2216 (e.g., a pico cylinder made commercially available by Picocyl) can open to pressurize a chamber 2214 that is fluidically coupled to a proximal side of the syringe plunger (e.g., using an attachment similar to a common pneumatic adhesive dispenser). This arrangement or mechanism can advantageously allow for a steady, controlled dispensing of a pressurized supply of the fluid 2126 (e.g., viscoelastic or other OVD fluid) from the syringe 2125. When the trigger 2212 is released, a spring 2218 can relax to an uncompressed configuration and pushes the pressure cartridge 2216 back to its nominal location and the chamber 2214 is vented via a cutout 2220 to, for example, abruptly stop viscoelastic or other fluid dispensing. As shown in FIG. 32E, a valve 2222 of the pressure cartridge 2216 may be open and the spring 2218 compressed when the trigger 2212 is depressed, and the valve 2222 may be closed and the spring 2218 relaxed or extended (e.g., moves back to its unactuated position) when the trigger 2212 is released.

The trigger 2212 can include a cutout 2220 formed on a side of its body. Before the trigger 2212 is depressed, the cutout 2220 may not be fluidly connected with the chamber 2214. As the trigger 2212 is depressed, the cutout 2220 can create a path between the chamber 2214 and the ambient.

When the trigger 2212 is fully compressed and the cartridge 2216 opens to pressurize the chamber 2214, the cutout 2220 may be separated from the ambient so that pressure in the chamber 2214 may be retained. When the trigger 2212 is released and moves back to its unactuated position, the cutout 2220 can create a path between the chamber 2214 and the ambient to vent the chamber 2214 to, for example, as described herein, abruptly stop viscoelastic or other fluid dispensing.

Figure 33A:
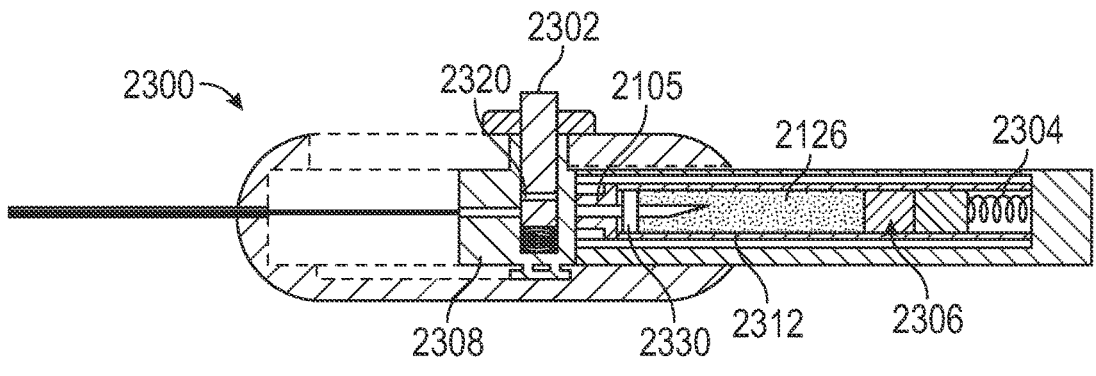
FIG. 33A depicts another embodiment of a cannula adapter that utilizes a compressed spring to hold a force to the ophthalmic viscosurgical device.
Figure 33B:
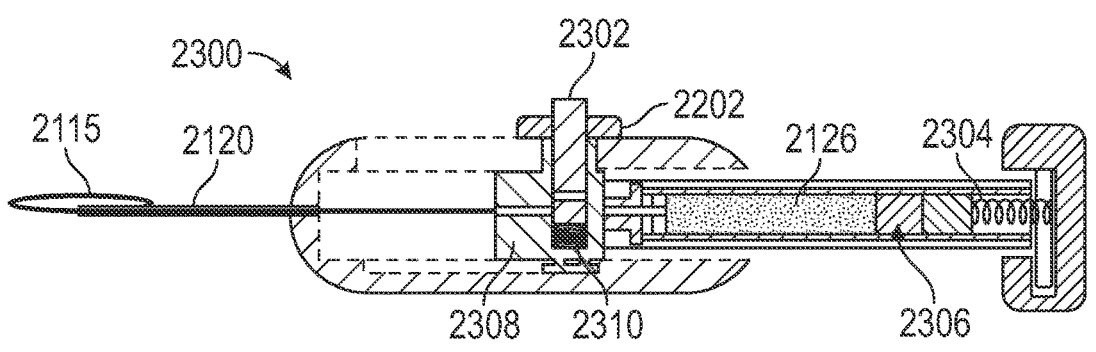
FIGS. 33B-33D depicts an example operation scheme of the cannula adapter of FIG. 33A.
Figure 33C:
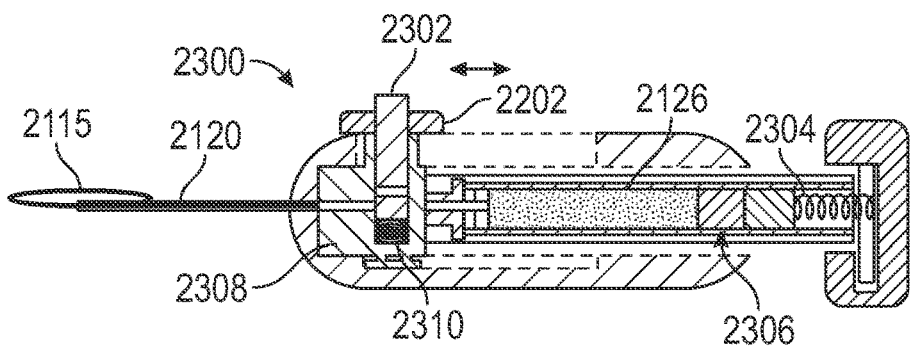
Figure 33D:
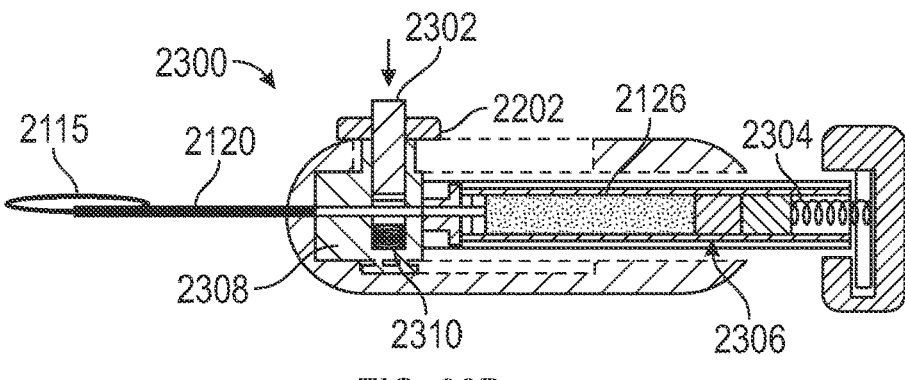

FIGS. 33A-33D illustrate alternative embodiments of a viscoelastic dispensing mechanism incorporating valves and springs that may be incorporated into any of the embodiments described herein. FIG. 33A shows a cannula adapter 2300 that utilizes a compressed spring 2304 to hold a force to a viscoelastic cartridge/plunger 2306. As described herein, actuating the (e.g., sliding towards the patient) the sliding trigger 2202 can cause the catheter 2115 to be extended out from a distal end of the outer cannula 2120. In the example illustrated in FIG. 33A, the connector 2105 can include a dispense button 2302 and a valve 2308. The dispense button 2302 can have an unactuated position and an actuated position. When in the unactuated position (as shown in FIG. 33C), the body of the dispense button 2302 can break the flow path within the connector 2105 and, for example, prevent the fluid 2126 from flowing from the viscoelastic cartridge 2306 into the catheter 2115. When in the actuated position (e.g., pressed downwards to compress a spring 2310 as shown in FIG. 33D), a lumen 2320 formed within the dispense button 2302 can connect with the flow path within the connector 2105 and between the viscoelastic cartridge 2306 and the catheter 2115. When the dispense button 2302 is released, the spring 2310 can urge the dispense button 2302 to return to the unactuated position and break the flow path between the viscoelastic cartridge 2306 and the catheter 2115.

In some implementations, as shown in FIG. 33A, the viscoelastic cartridge 2306 includes an optional diaphragm 2330, and the connector 2105 (e.g., Luer connector as shown in FIG. 31A) can include a hypodermic needle 2312 to puncture the diaphragm 2330.

The viscoelastic cartridge 2306 may be housed in a single sliding assembly (as shown in FIG. 33A) or may have a separate attachment with a plunger spring 2304 (as shown in FIGS. 33B-33D). With reference to FIGS. 33B-33D, which better illustrates operation of the viscoelastic dispensing mechanism, the thumb slider/trigger 2202 can be used to actuate the inner catheter 2115 in and out of Schlemm's canal (as shown in FIGS. 33C and 33D), while the dispensing button 2302 is used to dispense the fluid 2126 (e.g., viscoelastic or other OVD fluid) from the viscoelastic cartridge 2306 (as shown in FIG. 33D).

Figure 34A:
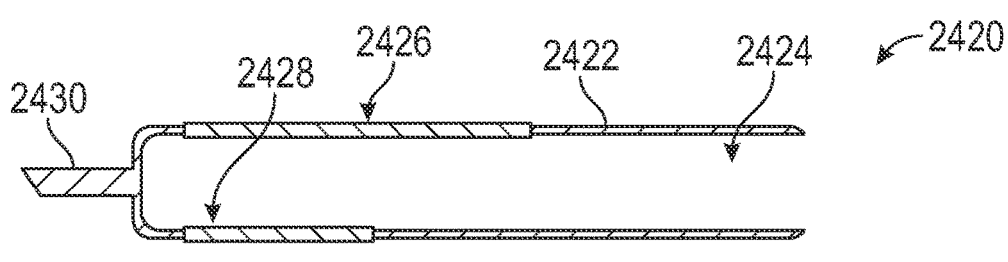
FIGS. 34A-34C depict a three-layer assembly that can be incorporated into any of the embodiments of the cannula adapters.
Figure 34B:
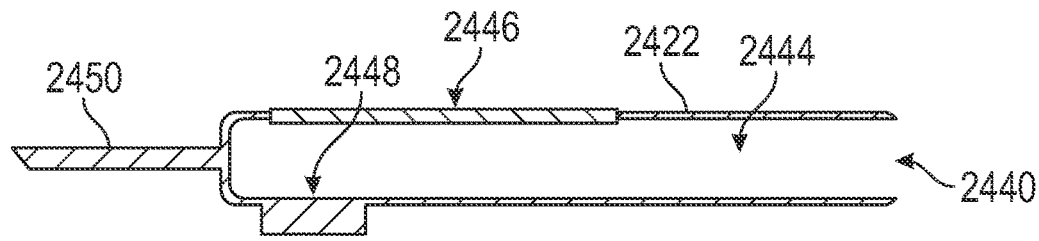
Figure 34C:
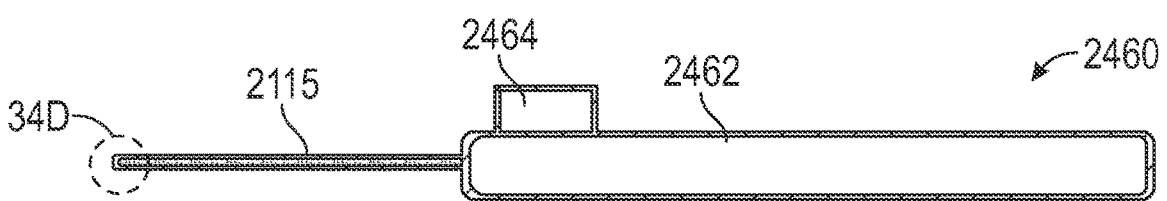

In accordance with several embodiments, the cannula adapters described and illustrated herein may be configured with multiple sliding layers as shown schematically in FIGS. 34A-34C. The multiple sliding layers may comprise three layers: a needle assembly 2420 comprising a sharp distal tip designed for penetration through the cornea, a cannula assembly 2440 comprising a tip designed to traverse the anterior chamber and penetrate the trabecular meshwork, and an inner catheter assembly 2460 with a blunt or rounded distal tip designed to traverse Schlemm's canal and a lumen to deliver viscoelastic or other fluid. FIG. 34A illustrates the needle assembly 2420 of a cannula adapter 2400 (as shown in FIG. 34E), FIG. 34B illustrates the cannula assembly 2440, and FIG. 34C illustrates the inner catheter assembly 2460.

The needle assembly 2420 and the cannula assembly 2440 may include slots as illustrated. The needle assembly 2420 can include a body 2422, a lumen 2424, an upper slot 2426, a lower slot 2428, and a needle 2430. The needle 2430 may be integrated with the body 2422. The slots 2426, 2428 can be formed opposite from each other on the body 2422. In some implementations, the locations of the slots 2426, 2428 can be different from the example illustrated in FIG. 34A. The cannula assembly 2440 can include a body 2442, a lumen 2454, an upper slot 2446, a cannula slider 2448, and a tip 2450. The tip 2450 and the cannula slider 2448 can be integrated with the body 2442 such that movement of the cannula slider 2448 can translate to movement of the body 2442 and the tip 2450. The upper slot 2446 may be formed on the body 2442. The inner catheter assembly 2460 can include a body 2462, a catheter slider 2464, and the catheter 2115. The catheter slider 2464 and the catheter 2115 may be integrated with the body 2462 such that movement of the catheter slider 2464 can translate to movement of the body 2462 and the catheter 2115.

Figure 34D:
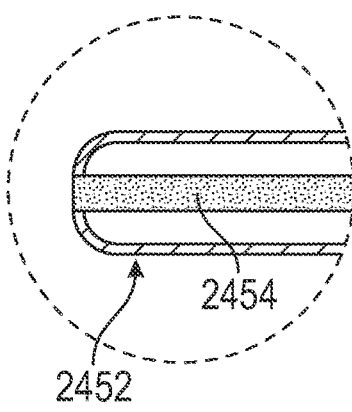
FIG. 34D depicts a close-up, side view of a distal tip of the three-layer assembly of FIG. 34C.
Figure 34E:
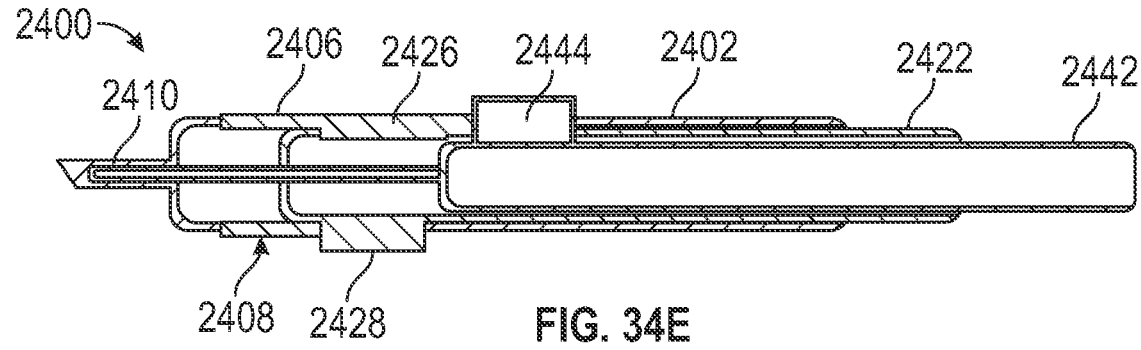
FIGS. 34E-34G depict an example operation scheme of the three-layer assembly of FIGS. 34A-34C.
Figure 34F:
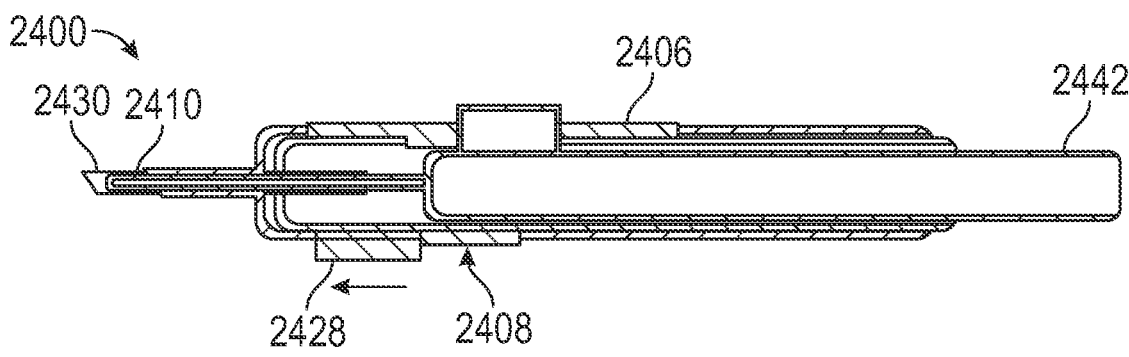
Figure 34G:
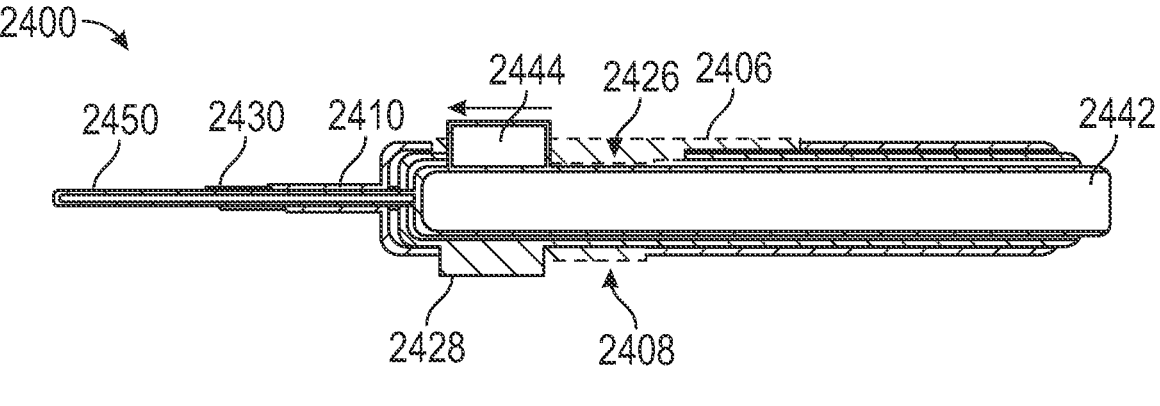

The operation, and assembled arrangement, of the three sliding layers of the cannula adapter 2400 is shown schematically in FIGS. 34E-34G. The cannula assembly 2440 can be positioned within the needle assembly 2420 such that the upper slot 2446 of the cannula assembly 2440 overlaps with at least a portion of the upper slot 2426 of the needle assembly 2420 and the cannula slider 2448 is positioned within the lower slot 2428 of the needle assembly 2420. The catheter assembly 2460 can be positioned within the cannula assembly 2440 such that the catheter slider 2464 is positioned within the upper slots 2426, 2446 of the needle assembly 2420 and the cannula assembly 2440, respectively.

The needle 2430 can, as described herein, penetrate cornea of a patient. The cannula slider 2448 can slide within the slot 2428 of the needle assembly 2420 to cause the cannula assembly 2440 to slide within the needle assembly 2420. When the cannula slider 2448 is moved distally (e.g., towards the patient), the tip 2450 of the cannula assembly 2440 can move distally and, for example, penetrate a superior trabecular meshwork (TM) portion of the patient. The slot 2446 of the cannula assembly 2440 can overlap with at least a portion of the slot 2426 of the needle assembly 2420 to allow the catheter slider 2464 to slide distally (e.g., towards the patient) and proximally (e.g., away from the patient) within the slots 2426, 2446. When the catheter slider 2444 is moved distally (e.g., towards the patient), the catheter 2115 can, for example, exit via a distal end of the tip 2450 and, for example, enter and travel along the Schlemm's canal. FIG. 34D shows a close-up side view of a distal tip of the catheter 2115. As shown in FIG. 34D, the catheter 2115 can include a rounded tip 2452 and a lumen 2454 that allows viscoelastic fluid or other fluid to flow through.

The three sliding layer assembly shown and described in FIGS. 34A-34G may advantageously remove the need for multiple separate surgical instruments, thereby streamlining the surgery.

FIGS. 35A-38B illustrate internal components of various embodiments of the cannula adapters described herein. A clear challenge with larger catheter extension is prevention of internal buckling as the inner catheter 2115 is fed through the outer cannula 2120. FIGS. 35A-38B show various internal support mechanisms (that may be used separately or one or more mechanisms may be combined together) designed to prevent buckling and guide the inner catheter 2115 along the outer cannula 2120.

Figure 35A:
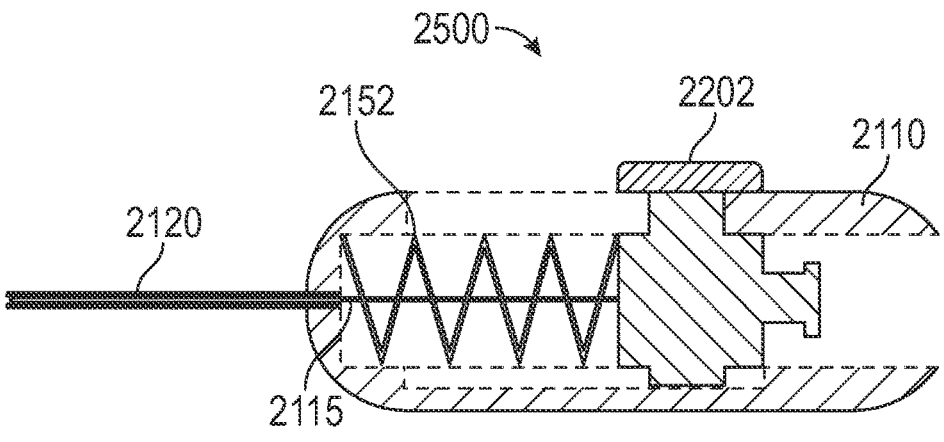
Figure 35B:
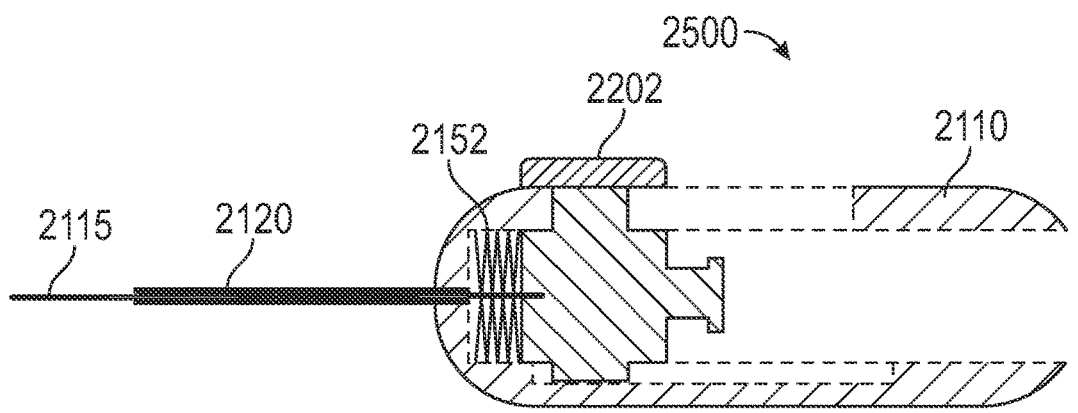

FIGS. 35A and 35B illustrate side views (undeployed configuration and fully-deployed configuration, respectively) of a cannula adapter 2500 including a collapsible, helical support 2152 with an inner diameter that is just larger than the inner catheter 2115 and an outer diameter confined by the housing 2110. The helical support 2152 can have a near-zero spring force, but still maintain radial stability.

Figure 36A:
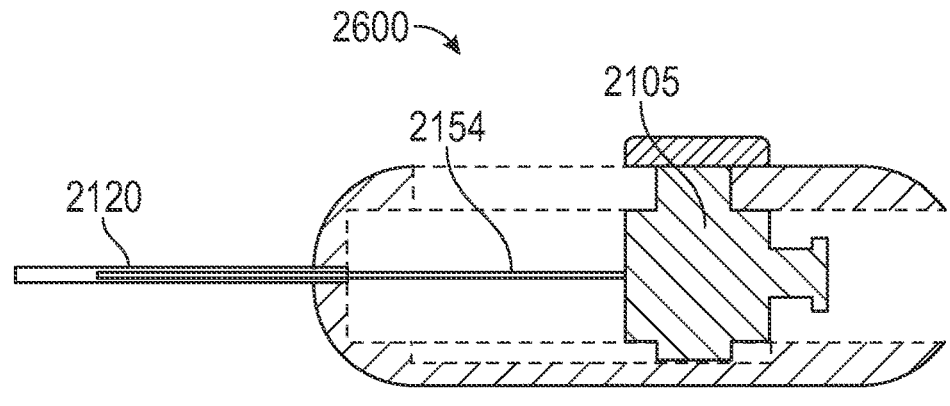

FIGS. 36A and 36B illustrate side views (undeployed configuration and fully-deployed configuration, respectively) of a cannula adapter 2600 including a rigid support tube 2154 with an inner diameter sized to fit the inner catheter 2115 and an outer diameter sized to slide within the outer cannula 2120. The rigid support tube 2154 may be formed of any suitable rigid material (such as a 300 series stainless steel). In some implementations, use of the rigid support tube 2154 may cause an increase in the diameter of the outer cannula 2120.

FIGS. 37A and 37B illustrate side views of a cannula adapter 2700 including a wheel 2701 and catheter feeders 2702, 2704. The catheter feeders 2702, 2704 can stabilize and prevent bending of the catheter 2115 as it moves distally (e.g., towards the patient) or proximally (e.g., away from the patient). The wheel 2701 can be coupled to the catheter feeder 2702 such that rotation of the wheel 2701 can translate to rotation of the catheter feeder 2702. For example, as shown in FIG. 37B, counterclockwise rotation of the wheel 2701 can cause clockwise rotation of the catheter feeder 2702. The clockwise rotation of the catheter feeder 2702 can cause the catheter 2115 to traverse distally (e.g., towards the patient). Likewise, clockwise rotation of the wheel 2701 can cause counterclockwise rotation of the catheter feeder 2702, which can cause the catheter 2115 to traverse proximally (e.g., away from the patient). In some implementations, the catheter feeders 2702, 2704 are coupled to each other such that rotation of one causes rotation of another. For example, clockwise rotation of the catheter feeder 2702 can cause counterclockwise rotation of the catheter feeder 2704 (as shown in FIG. 37B). In some implementations, the movement (e.g., distal or proximal) of the catheter 2115 can cause rotation of the catheter feeder 2704. In some implementations, the catheter 2115 can be retracted by simply pulling on the assembly from the syringe 2125 (e.g., instead of rolling the wheel 2701 in clockwise direction).

Figure 38A:
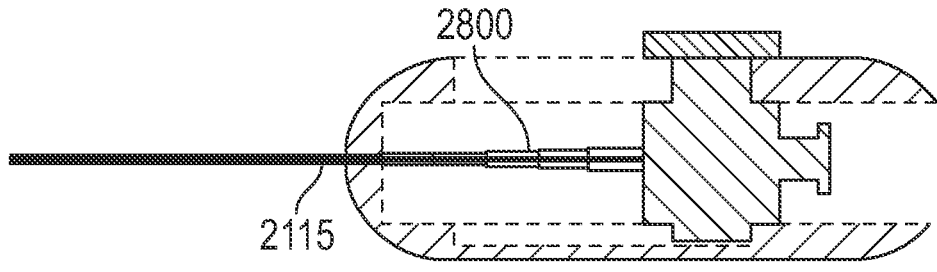
Figure 38B:
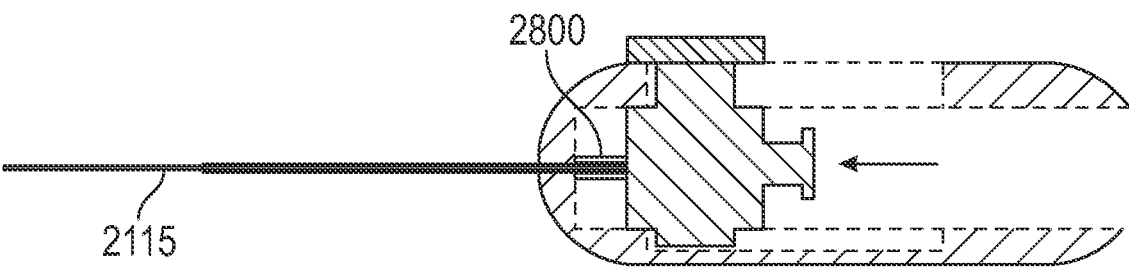

FIGS. 38A and 38B illustrate side views (e.g., undeployed configuration and fully-deployed configuration, respectively) of a telescoping tube 2800 that provides support for the catheter 2115 while collapsing during actuation, which may be incorporated into any of the embodiments of cannula adapters or fluid (e.g., viscoelastic) delivery devices described or illustrated herein.

FIGS. 39A-39F illustrate a feed mechanism 2900 that may be used to feed the catheter 2115 into the outer cannula 2120. The feed mechanism 2900 may be incorporated into any of the embodiments of cannula adapters described or illustrated herein. The feed mechanism 2900 can include a thumb-controlled dial 2901 positioned near a distal end of the housing 2110 to facilitate single-handed operation by an operator.

Figures 39A, 39B, 39C, 39D:
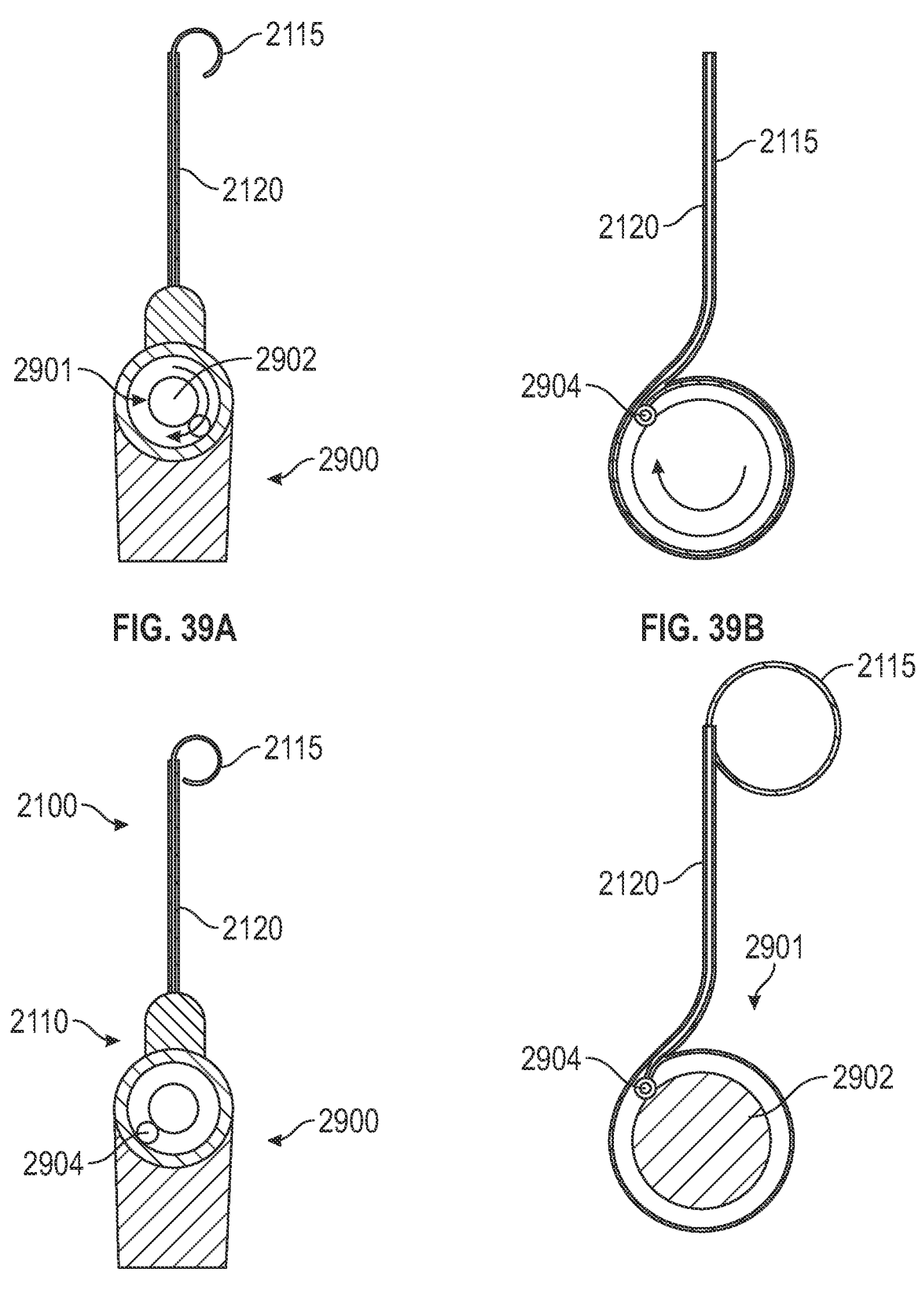
FIGS. 39A-39B depict external top views of an embodiment of a cannula adaptor with a dial-feed system, showing an example operation scheme of the cannula adaptor.
FIGS. 39C-39D depict internal top views showing an example operation scheme of the cannula adaptor of FIG. 39A.

The dial 2901 can be rotated by a thumb of the operator by interaction with a nub or protrusion 2904 extending upward from the dial 2901. Alternatively, the nub or protrusion 2904 could include a dimple or indent. The dial 2901 can be operatively coupled to a proximal end of the inner catheter 2115 such that rotation of the dial 2901, for example, in a clockwise direction advances the inner catheter 2115 along and then out of the outer cannula 2120 and into and along Schlemm's canal in a controlled manner, and rotation of the dial 2901, for example, in a counter-clockwise direction retracts the inner catheter 2115. Of course, these directions could be reversed as desired and/or required. The distal portion of the inner catheter 2115 that is adapted to extend out of the distal tip of the outer cannula 2120 upon full rotation of the dial 2901 (e.g., the internal loop) may have a length adapted to match or correspond to (e.g., is approximately equal to) a full 360-degree circumference of Schlemm's canal as described herein. In some implementations, 360-degree rotation of the dial 2901 (as shown in FIGS. 39B and 39D) corresponds to 360 degrees of travel along Schlemm's canal by the catheter 115. In addition, the distal portion of the inner catheter 2115 may include pre-shaped (e.g., shape set material with a defined radius of curvature corresponding to the radius of curvature of Schlemm's canal) or flexible material features as described herein.

The dial 2901 can include a button 2902 that can be depressed by the thumb of the operator. The button 2902, when actuated (e.g., move from an unactuated position to an actuated position) may cause dispensing of viscoelastic or other viscosurgical fluid. For example, the button 2902, when actuated, can cause (e.g., actuate) a control valve to dispense the viscoelastic or other viscosurgical fluid. Dispensing of the viscoelastic or other viscosurgical fluid may occur at a constant rate, a variable rate based on an amount that the button 2902 is depressed, or a predetermined bolus amount per button press. In some implementations, actuation of the button 2902 may actuate a pump such as a positive displacement pump.

In some implementations, the feed mechanism 2900 may include indents or detents positioned at clock hours around the dial 2901. The indents or detents can provide the operator an indirect indication of the azimuthal position of the catheter 2115 within Schlemm's canal without requiring actual visualization via imaging modalities. For example, the detents at each clock hour may provide a tactile feedback (e.g., false stop) to the operator or generate an audible click to provide audible feedback to the operator. The operator can stop at a given clock hour and dispense a given volume of viscoelastic or other fluid, and then move to the next clock hour.

Figure 39E:
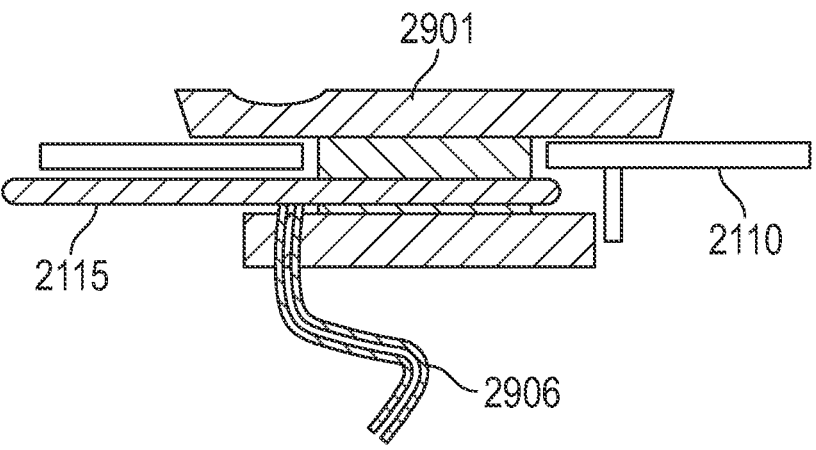
FIGS. 39E-39F depict side views showing an example operation scheme of the cannula adaptor of FIG. 9A.
Figure 39F:
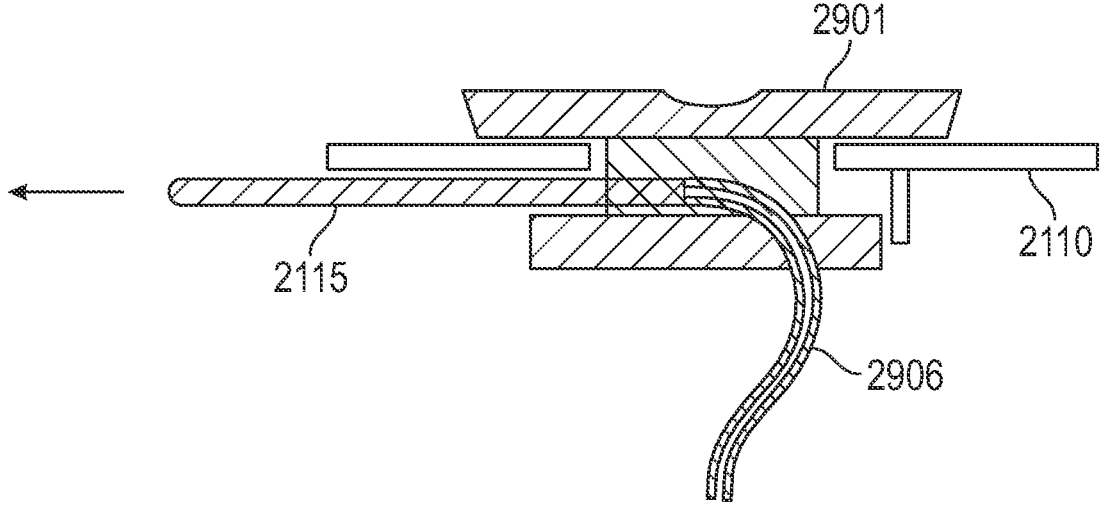

The catheter 2115 may be made of one or multiple joined materials, such as nylon/Pebax® polymer, polyimide, etc. The proximal end of the catheter 2115 may be overmolded (e.g., insert molded) into or bonded to (e.g., via an adhesive) the dial mechanism. The channeling to feed the catheter 2115 into the outer cannula 2120 may be a separate molded or metallic component, or may be formed with the housing 2110 of the cannula adapter 2100. FIGS. 39E and 39F illustrate an example of how the dial 2901 may be incorporated into or assembled with the housing 2110. The inner catheter 2115 may be connected to a fluid delivery system (not shown) such as a valve or syringe (such as those described herein) via a separate section of tubing 2906 fluidically coupled to the catheter 2115 (as shown in FIGS. 39E and 39F) or via channels formed into the molded components. In some configurations, a valve may be directly integrated into the dial mechanism.

Figures 40A, 40B, 40C:
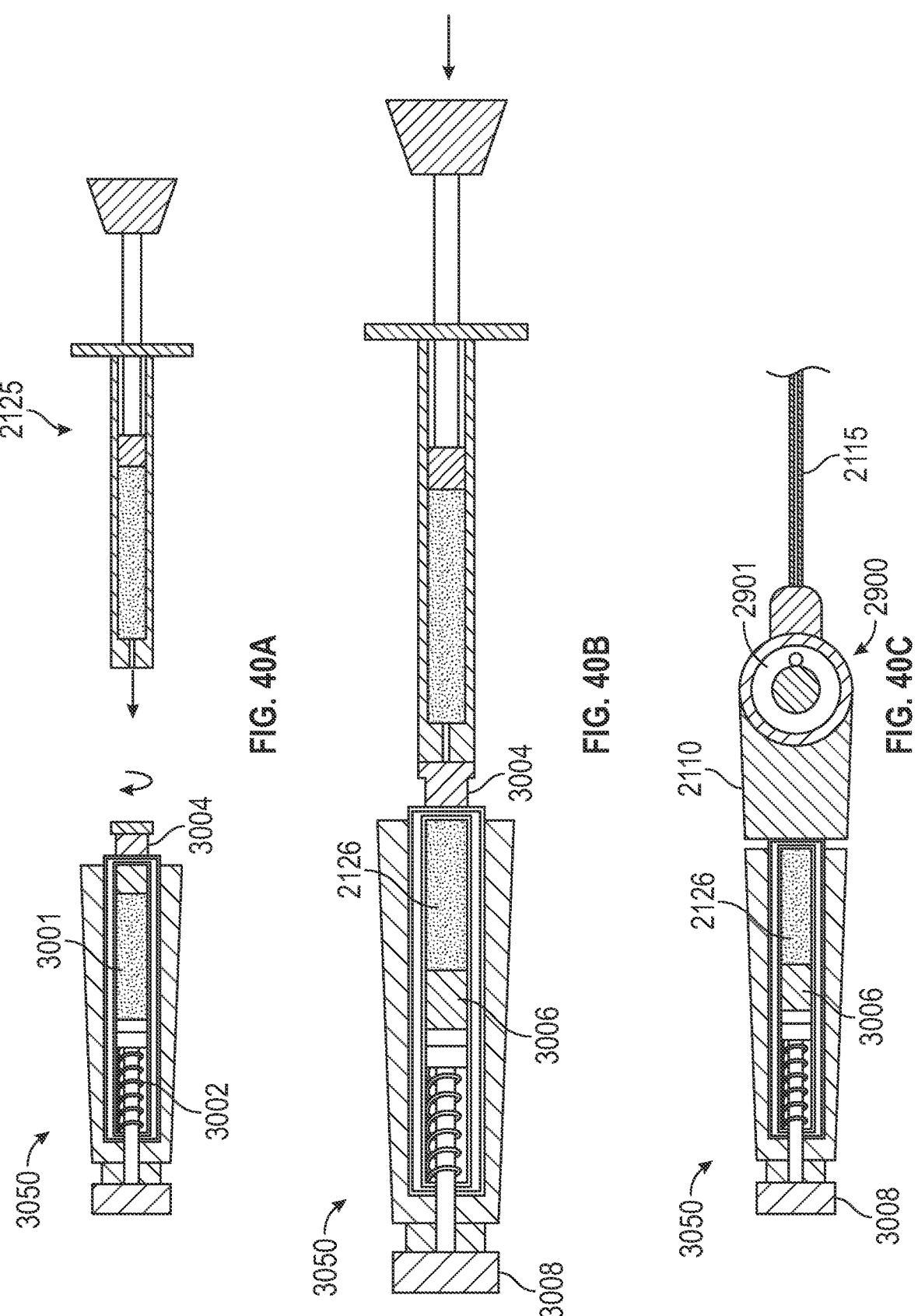
FIGS. 40A-40C depict an example operation scheme of a cannula adapter with a spring driven system having a fillable reservoir.

The cannula adapters described and illustrated herein may incorporate a variety of different viscoelastic dispensing mechanisms or systems. FIGS. 40A-40C illustrate an embodiment of a delivery system 3050 in conjunction with the cannula adapter (feed mechanism 2900) of FIGS. 39A-39F. The delivery system 3050 can include a reservoir 3001, a spring 3002, a connector 3004, a stopper 3006, and a base member 3008. The reservoir 3001 (or cartridge) that may be removably coupled (e.g., friction fit, corresponding mating features, latches and notches, etc.) to the housing 2110 of the cannula adapter (feed mechanism 2900). The reservoir 3001 can include a spring 3002, which can be retracted to a compressed position (or configuration) before use as shown in FIG. 40A. The stopper 3006 (e.g., rubber stopper) can be positioned within and near the proximal end (e.g., an end opposite from the feed mechanism 2900) of the reservoir 3001. The connector 3004 (e.g., a female Luer connector) can be placed at the distal end (e.g., an end proximate to the feed mechanism 2900) of the reservoir 3001 to facilitate direct connection to any standard viscoelastic syringe or other viscosurgical device (e.g., a pre-filled ophthalmic viscoelastic device 2125). In some implementations (not shown), a septum may be present at the distal end of the reservoir 3001 that can be pierced with a needle or dispensing cannula.

The reservoir 3001 may be filled with fluid 2126 (e.g., viscoelastic or other ophthalmic viscosurgical device (OVD) fluid) by depressing the plunger of the standard viscoelastic syringe 2125. As the reservoir 3001 is filled, the stopper 3006 can be pushed back to the compressed spring 3002. A bleed valve or air breathable material, such as a porous plastic or porous polymer material, may be integrated into the reservoir 3001 to allow further purging of air during the fill. Once a desired amount of the fluid 2126 (e.g., viscoelastic or other fluid) is added to the reservoir 3001, the delivery system 3050 can be connected to the housing 2110 including the catheter 2115. Once the delivery system 3050 is connected to the housing 2110, the base member 3008 can be rotated to release the spring 3002 to apply force to the stopper 3006. The spring 3002 may be operatively coupled to the base member 3008 so as to facilitate engagement of (e.g., compression and relaxation) the spring 3002 upon actuation of the base member 3008. In some implementations, rotation of the base member 3008 can cause compression or relaxation of the spring 3002. In accordance with several embodiments, the delivery system 3050 of FIGS. 40A-40C can advantageously accommodate any choice of viscoelastic or other fluid and different amounts of viscoelastic or other fluid. The delivery system 3050 can ensure that a consistent spring force is applied to the reservoir 3001 when filled.

Figures 41A, 41B:
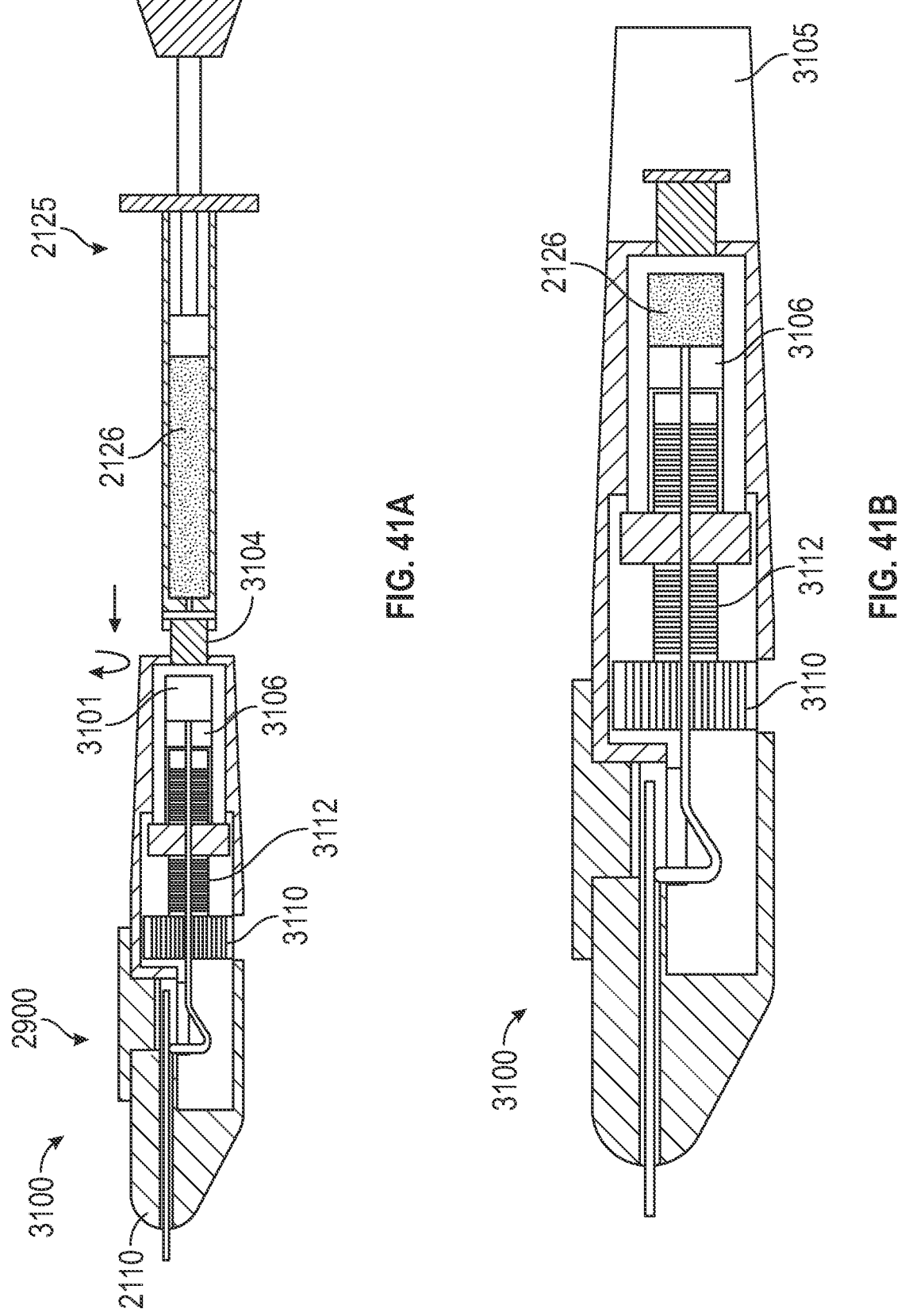
FIGS. 41A-41B depict an example operation scheme of a fillable cannula adapter having a threaded plunger fluid delivery system with reverse flow.

With reference to FIGS. 41A and 41B, a fillable cannula adapter 3100 is disclosed herein. The embodiment of the cannula adapter 3100 illustrated in FIGS. 41A and 41B utilizes a screw-driven (or threaded plunger) system that can be incorporated into the housing 2110 of the cannula adapter 3100 or housings of other embodiments of cannula adapters described herein. The cannula adapter 3100 can include a threaded plunger 3112, a wheel 3110, a reservoir 3101, and a connector 3104 (e.g., standard Luer connector or check valve). The reservoir 3101 can be filled (e.g., primed) with the fluid 2126 from the syringe 2125 (e.g., a standard viscoelastic syringe) and a cap or other sealing member can be placed on a back end of the reservoir 3101 prior to operation. The wheel 3110 may be located and positioned such that the wheel 3110 is accessible via a slot formed in a belly (e.g., bottom side or lower side) of the housing 2110. The wheel 3110 may be conveniently positioned as to be rotated by an index finger or middle finger of the operator as the housing 2110 is held in the operator's hand with the thumb over the dial 2900. The threaded plunger 3112 can be operatively and mechanically coupled to the wheel 3110 such that the threaded plunger 3112 is actuated by rotation of the wheel 3110. The threaded plunger 3112 and the wheel 3110 can include a lumen that is fluidically coupled to tubing (e.g., flexible silicone tubing) that is in turn fluidically coupled to the lumen of the catheter 2115. In some implementations, the lumen of the threaded plunger 3112 may be directly coupled to the lumen of the catheter 2115 without an intermediate tubing. As the threaded plunger 3112 pushes on the reservoir 3101, the fluid 2126 (e.g., viscoelastic or other ophthalmic viscosurgical device (OVD) fluid) is dispensed back through the plunger 3112 toward the catheter 2115.

Although the fluid delivery system is illustrated in FIGS. 41A and 41B is coupled to the feed mechanism 2900 described and illustrated in connection with FIGS. 39A-93F, the fluid delivery system of FIGS. 41A and 41B could theoretically work with any suitable feed system embodiment. In accordance with several embodiments, the catheter 2115 is able to move independent of the threaded plunger 3112 (e.g., via the feed mechanism 2900), such that the operator can dispense fluid at any time. This independent movement capability may be performed by linking the plunger tube (e.g., a tube that extends through the lumen of the wheel 3110 and the plunger 3112) to the catheter 2115 via flexible tubing (e.g., silicone tubing) with slack. The connection between the plunger tube and the catheter 2115 may alternatively be made with Pebax® polymer tubing or other more durable tubing, or with rigid tubing shaped like a spring to allow independent motion of the catheter 2115.

The connector 3104 (e.g., a female connector) can allow the operator to fill the reservoir 3101 with any standard viscoelastic syringe 2125, as with the delivery system 3050 illustrated in FIGS. 40A-40C. The reservoir 3101 and entire downstream system could be primed with the syringe 2125. The reservoir 3101 and the stopper 3106 (e.g., rubber stopper) may be shaped such to streamline the filling procedure and prevent unwanted trapped air. The operator could then detach the viscoelastic syringe 2125 and replace with a plug or cap 3105. The plug or cap 3105 may be shaped to form the rest of the handle for ergonomics. The cap 3105 may also have an extension that protrudes into the reservoir 3101 to purge any last bit of air from the connection when attached. Alternatively, the device may include a valve that can be closed when priming is complete.

The wheel 3110 of the housing 2110 (e.g., exposed on the belly of the housing 2110) may include detents to provide an indication of volume dispensed. For example, the detents can generate audible clicking noises or tactile feedback at each incremental volume. The detents may be user customizable such that the operator can choose to have a click at each 2 uL or a click at each 5 uL, for example. Of course, other volume indications may be used as desired and/or required. In some embodiments, the belly (or lower surface) of the housing 2110 may include multiple spaced-apart linear indicators that show the total volume dispensed thus far or remaining volume left in the reservoir (e.g., the reservoir 3101). This mechanism could be driven by a coupled screw with a coarser pitch to amplify the linear motion, or on a gear and pinion system, for example.

In accordance with several embodiments, the cannula adapter 3100 illustrated in FIGS. 41A and 41B can advantageously include a fluid delivery system configured for single-handed use that should be familiar to the operator. The fluid delivery system also allows dispensing of the viscoelastic or other fluid at any time as opposed to being coupled to the motion of the inner catheter, thereby allowing the operator to move through a barrier or obstruction that the inner catheter hits, or contact, while traversing along Schlemm's canal.

Figure 42A:
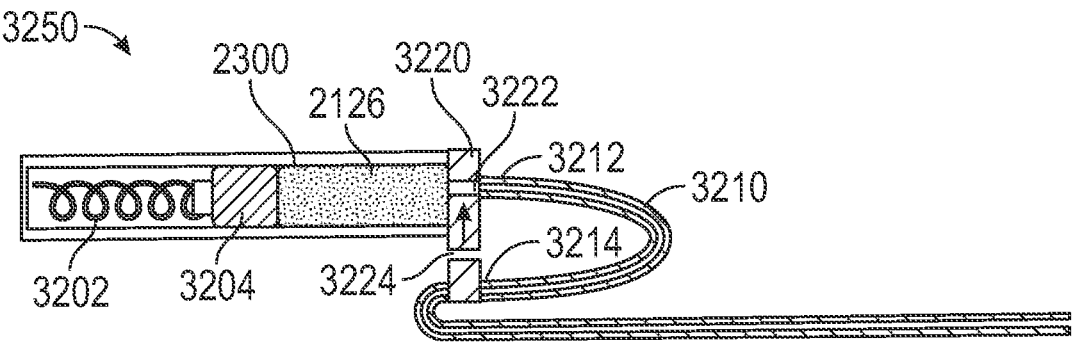
FIGS. 42A-42B depict an example operation scheme of an embodiment of a charged elastic tube fluid delivery mechanism.
Figure 42B:
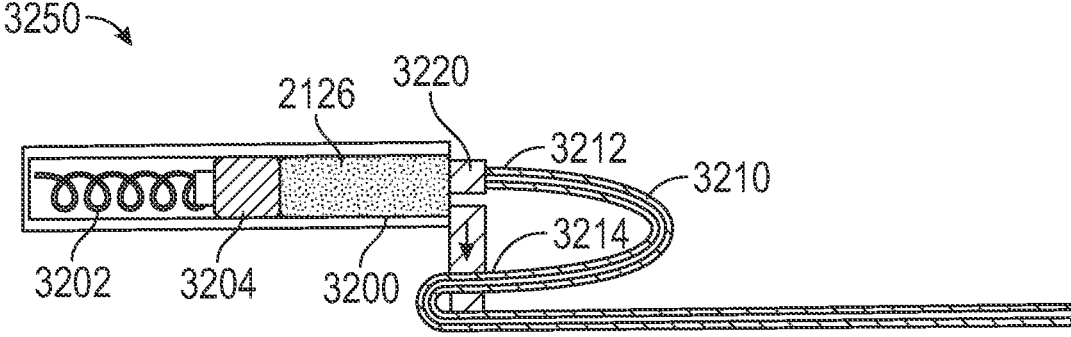

FIGS. 42A-42B illustrate an embodiment of a delivery system 3250 that may be incorporated into a cannula adapter described herein. The delivery system 3250 may advantageously allow for controlled microbolus dispensing. The delivery system 3250 can include an elastic (e.g., compliant) tube 3210 that is charged by closing a distal end 3214 of the tube 3210 and opening a proximal end 3212 of the tube 3210 to a pressurized (e.g., spring loaded) reservoir 3200. The reservoir 3200 may include a spring 3202 and a stopper 3204 with structural and operational features similar to the delivery system 3050 described in connection with FIGS. 40A-40C. After charging of the tube 3210 as shown in FIG. 42A, the operator may toggle a switch (not shown) to close the proximal end 3212 and open the distal end 3214 to discharge the elastic tube 3210 through the catheter 2115. The length, diameter, and durometer of the elastic tube 3210 can be varied to achieve the desired bolus volume.

The opening and closing of the proximal end 3212 and the distal end 3214 can be facilitated by causing a controller to move a block 3220 between different positions. For example, the block 3220 can have a first position (as shown in FIG. 42A) and a second position (as shown in FIG. 42B). When the block 3220 is in the first position, a first opening 3222 of the block 3220 can fluidically connect the proximal end 3212 of the tube 3210 and the reservoir 3200 while a second opening 3224 can be offset from the distal end 3214 to fluidically disconnect the distal end 3212 and the catheter 2115. As such, when the block 3220 is in the first position, the fluid 2126 (e.g., viscoelastic or other ophthalmic viscosurgical device (OVD) fluid) stored in the reservoir 3200 can enter into the tube 3210 via the proximal end 3212 and fill the tube 3210 up to the distal end 3214. When the block 3220 is in the second position, the first opening 3222 can be offset from the proximal end 3212 to fluidically disconnect the reservoir 3200 and the proximal end 3212 while the second opening 3224 can fluidically connect the distal end 3214 and the catheter 2115. As such, when the block is in the second position, fluid that was stored within the tube 3200 (e.g., between the proximal end 3212 and the distal end 3214) can be discharged into the catheter 2115 via the second opening 3224.

Figure 43A:
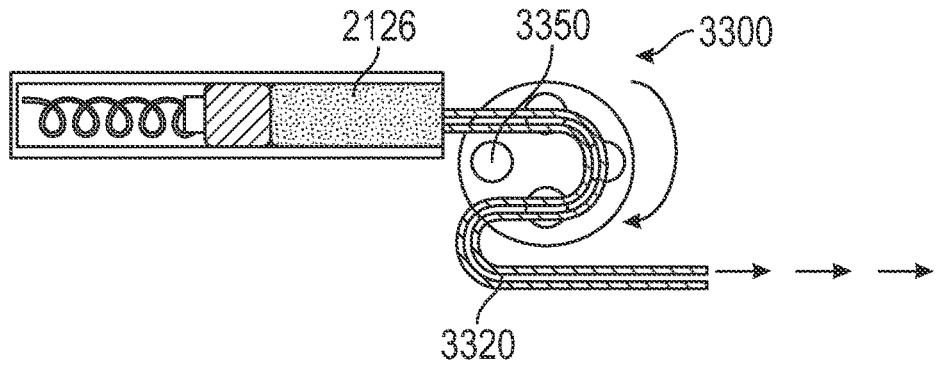
FIGS. 43A-43C depict an embodiment of a peristaltic fluid delivery mechanism.
Figure 43B:
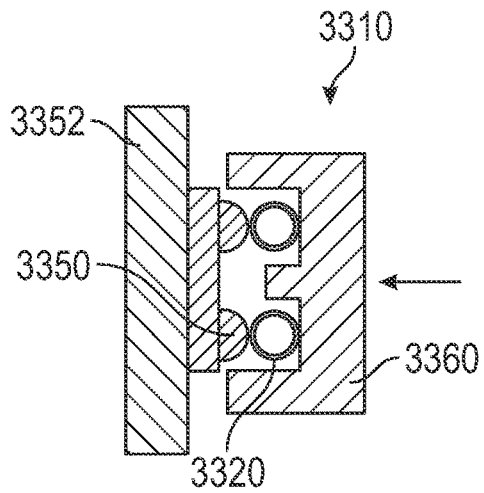
Figure 43C:
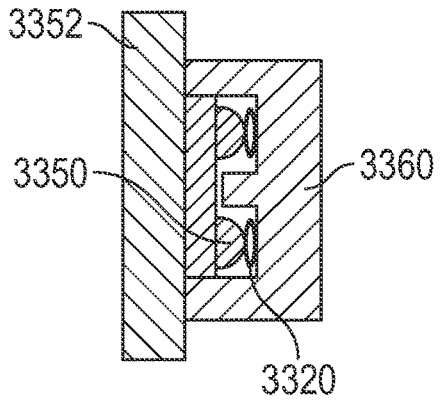

FIGS. 43A-43C illustrate an embodiment of a peristaltic fluid delivery system 3300. The peristaltic fluid delivery system 3300 can include an elastic (or compliant) tube 3320 and a peristaltic pump 3310 (shown in FIGS. 43B and 43C) that includes protrusions 3350 (e.g., rollers or ball bearings) adapted to sequentially compress or squeeze the tube 3320 at spaced-apart locations along a length of the tube 3320 so as to convey liquid between a fluid reservoir 3300 storing the fluid 2126 and the catheter 2115. At least a portion of the tube 3320 and the protrusions 3350 may be encased within a circular pump casing 3360. The peristaltic pump 3310 may be a rotary peristaltic pump (as shown) or a linear peristaltic pump.

In the illustrated embodiment, the tube 3320 can be positioned within the pump casing 3360 about the protrusions 3350 (e.g., ball bearings) on a rotor 3352. The pump casing 3360 can be actuated (e.g., pushed towards the rotor 3352) to pinch (e.g., compress) at least a portion of the tube 3320 with the protrusions 3350. While the pump casing 3360 is actuated, rotation of the rotor 3352 force the fluid 2126 downstream along the tube 3320. As each of the pump elements 3350 is disengaged with the tube 3320, fluid flow is induced into that respective portion of the tube 3320. FIGS. 43B and 43C illustrate cross-section views of the peristaltic pump 3310. The peristaltic fluid delivery system 3300 may be primed (e.g., allow the fluid 2126 to enter into the tube 3320) prior to the tube 3320 engaging the pump elements 3350. In some embodiments, the pump 3310 can be actuated by rotating the rotor 3352 after priming.

Figure 44:
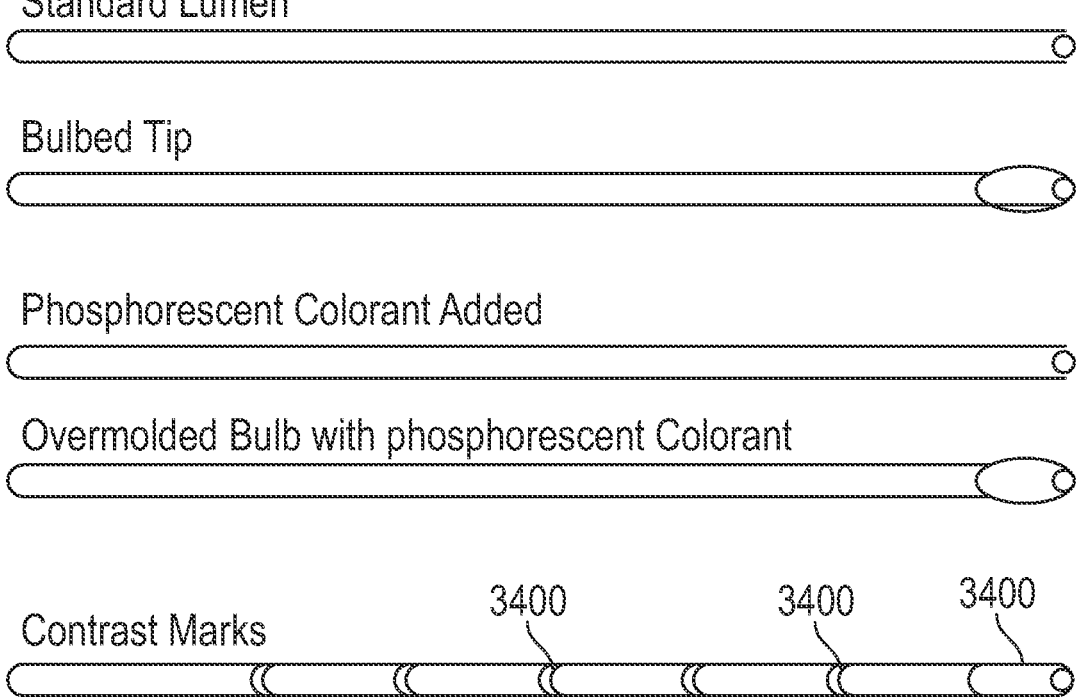
FIG. 44 depicts various examples of inner catheter shapes and features to facilitate visualization that may be incorporated into any of the embodiments of the cannula adapters.

FIG. 44 illustrates various concepts related to catheter shape and features to facilitate visualization or tracking of the catheter 2115 as it is advanced along Schlemm's canal. A key challenge of a visco delivery or other fluid delivery procedure is knowing where the tip of the inner catheter is so that it doesn't migrate to undesirable anatomy (such as the suprachoroidal space when the target is Schlemm's canal). The top image shows a standard catheter lumen. The second image from the top shows that a distal end of the inner catheter may include a bulbed tip. The bulbed tip may be achieved by overmolding material onto an extruded lumen. With reference to the third image in the middle, the catheter itself (e.g., the catheter 2115) may be formed using a polymer with a phosphorescent colorant such that it can be charged with a microscope light or an ultraviolet light/blue light source and then can glow when the lights are dimmed. The operator may alternatively have a UV/blue light source attached to a surgical microscope that can be switched on during a procedure to better view the phosphorescent catheter. In the embodiment illustrated in the fourth image (second from the bottom), the catheter includes a bulbed distal tip that is colored with the phosphorescent colorant (e.g., glow-in-the-dark material such as strontium aluminate). The bulbed tip may be overmolded on a distal end of an extruded lumen. The final image on the bottom shows that the catheter 2115 may include contrast marks 3400 spaced apart along a length of the inner catheter to facilitate visualization of the inner catheter (e.g., more clearly denote which part of the inner catheter you are seeing through the trabecular meshwork). The distal tip may include a more extensive (e.g., longer or wider) contrast mark to indicate the distal tip of the inner catheter. The cannula adapters described herein may be designed for use without a fiber optic cable so as to reduce cost.

Figures 45A, 45B:
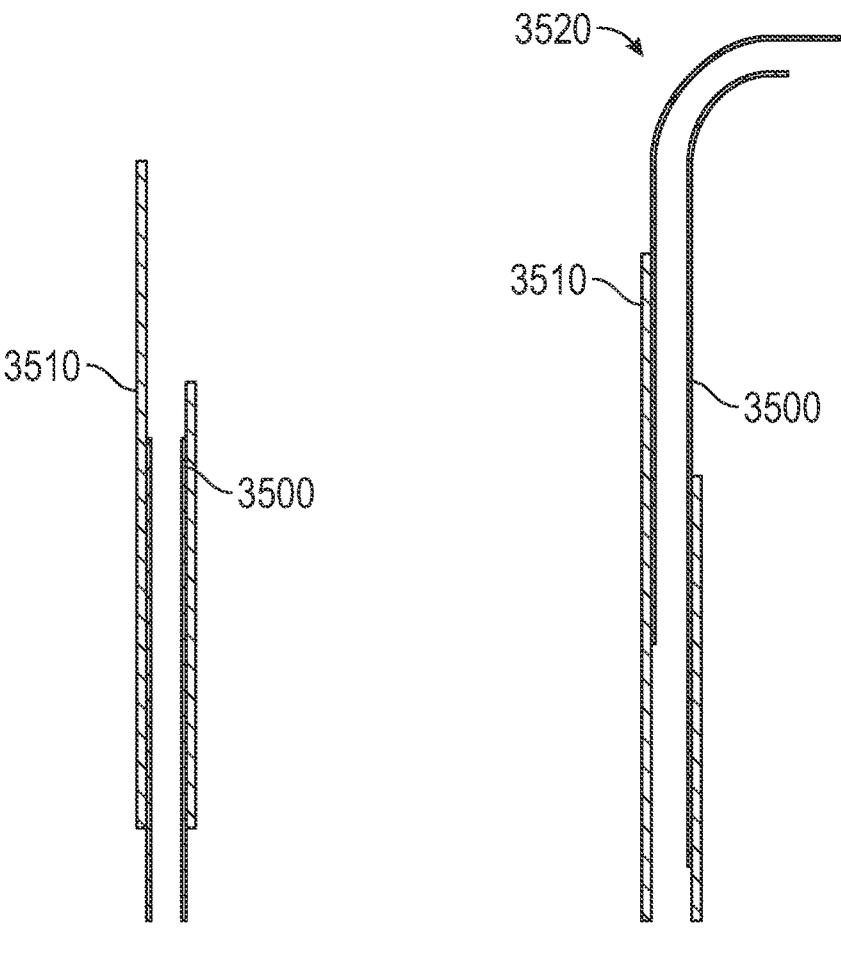
FIGS. 45A-45B depict an example operation of a shape set cannula that may be incorporated into any of the embodiments of the cannula adapters.

FIGS. 45A and 45B schematically illustrate operation of an outer cannula 3500 that utilizes shape memory material (e.g., nitinol or other shape memory alloy material) to form a shape set distal tip 3520. The distal tip 3520 of the cannula can be straight when confined by an introducer needle 3510 (e.g., 304 Stainless steel material, other 300 Series Stainless steel material or other material) but curves to a set shape when no longer constrained (e.g., by the introducer needle). This shape set configuration allows the outer cannula 3500 to slide within a rigid introducer needle 3510, but curve to enter Schlemm's canal when slid forward out of the introducer needle 3510.

Figure 46:
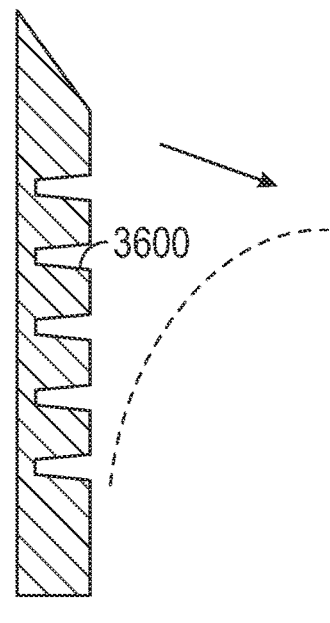
FIG. 46 depicts an embodiment of a cannula having a notched distal tip to facilitate articulation that may be incorporated into any of the embodiments of the cannula adapters.

FIG. 46 illustrates an embodiment of a distal end portion (e.g., distal tip) of the outer cannula 2120. As shown, the distal end portion (e.g., distal tip) may include notches 3600 in the tubing to allow the cannula 2120 to articulate in a particular direction. In some implementations, the distal end portion (e.g., distal tip) is connected to a pull wire such that the operator can control articulation of the cannula 2120 near the notched distal tip. In some implementations, the tip of the outer cannula 2120 may be configured to seat or anchor to the back wall of Schlemm's canal to prevent inadvertent motion of the tip during, for example, a visco or other fluid delivery procedure.

With reference to FIGS. 47A-47H, an embodiment of a cannula adapter, or fluid delivery device, 3700 is disclosed. The cannula adapter 3700 can include a housing 2110 having two portions 2110A, 2110B, a first slider 3702, a second slider 3704, a channel 3703, a fluid delivery conduit 3716, a stopper 3790, and a distal end 3706 having two portions 3706A, 3706B. The distal end 3706 can include an opening sized to receive a cannula 2120. The first slider 3702 can be mechanically and/or operably coupled to a reservoir 3780 and a plunger 3712. The second slider 3704 can include an insert 3740 that can be formed on, for example, an underside of the second slider 3704.

Figure 47A:
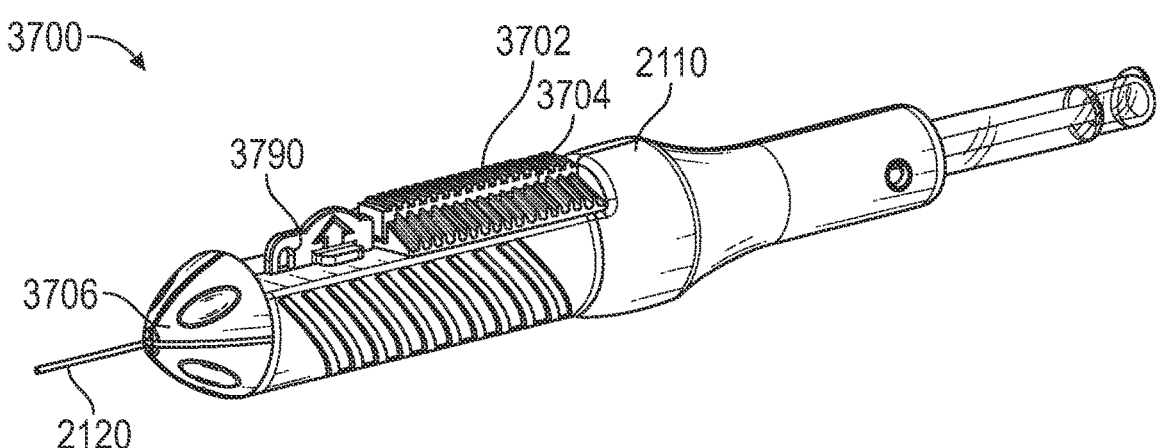
FIG. 47A depicts a perspective view of another embodiment of a cannula adapter, or fluid delivery device.
Figure 47B:
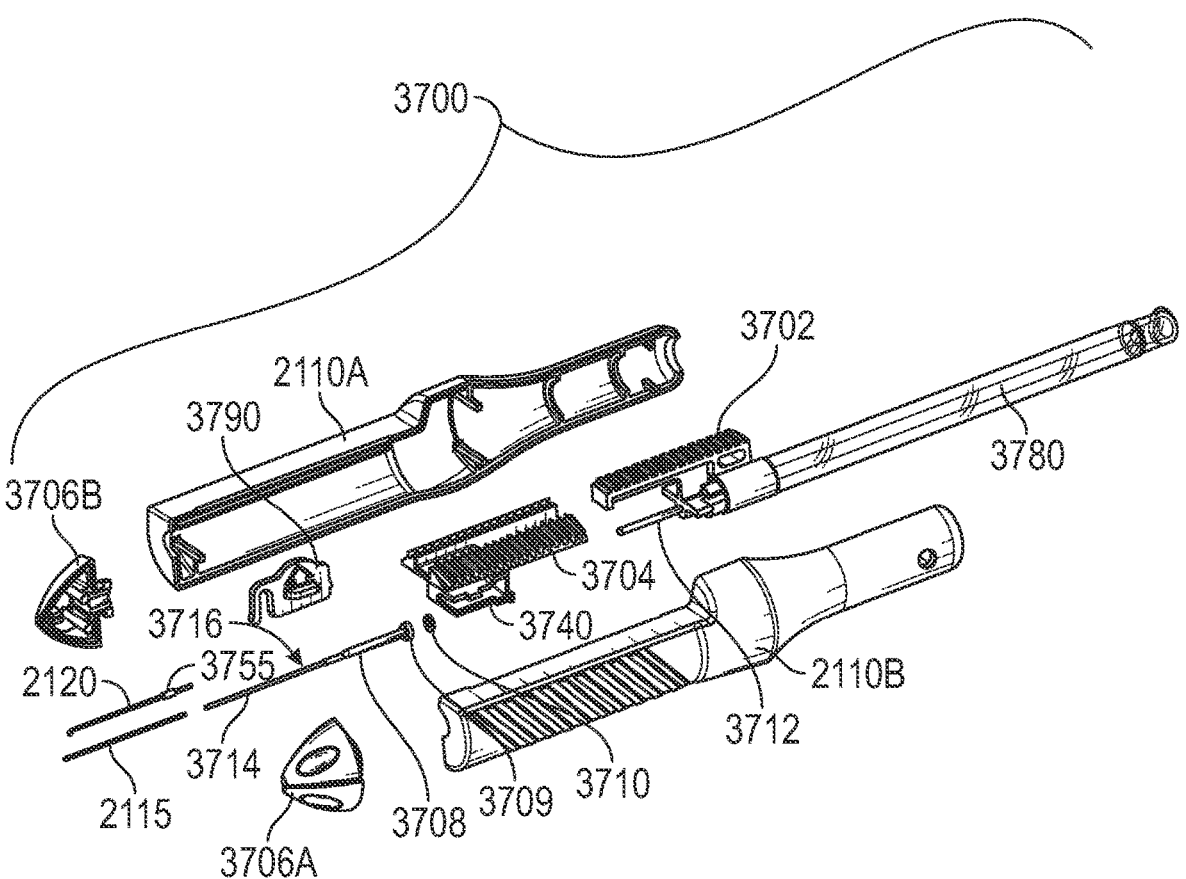
FIG. 47B depicts a perspective, exploded view of the cannula adapter of FIG. 47A.
Figures 47C, 47D:
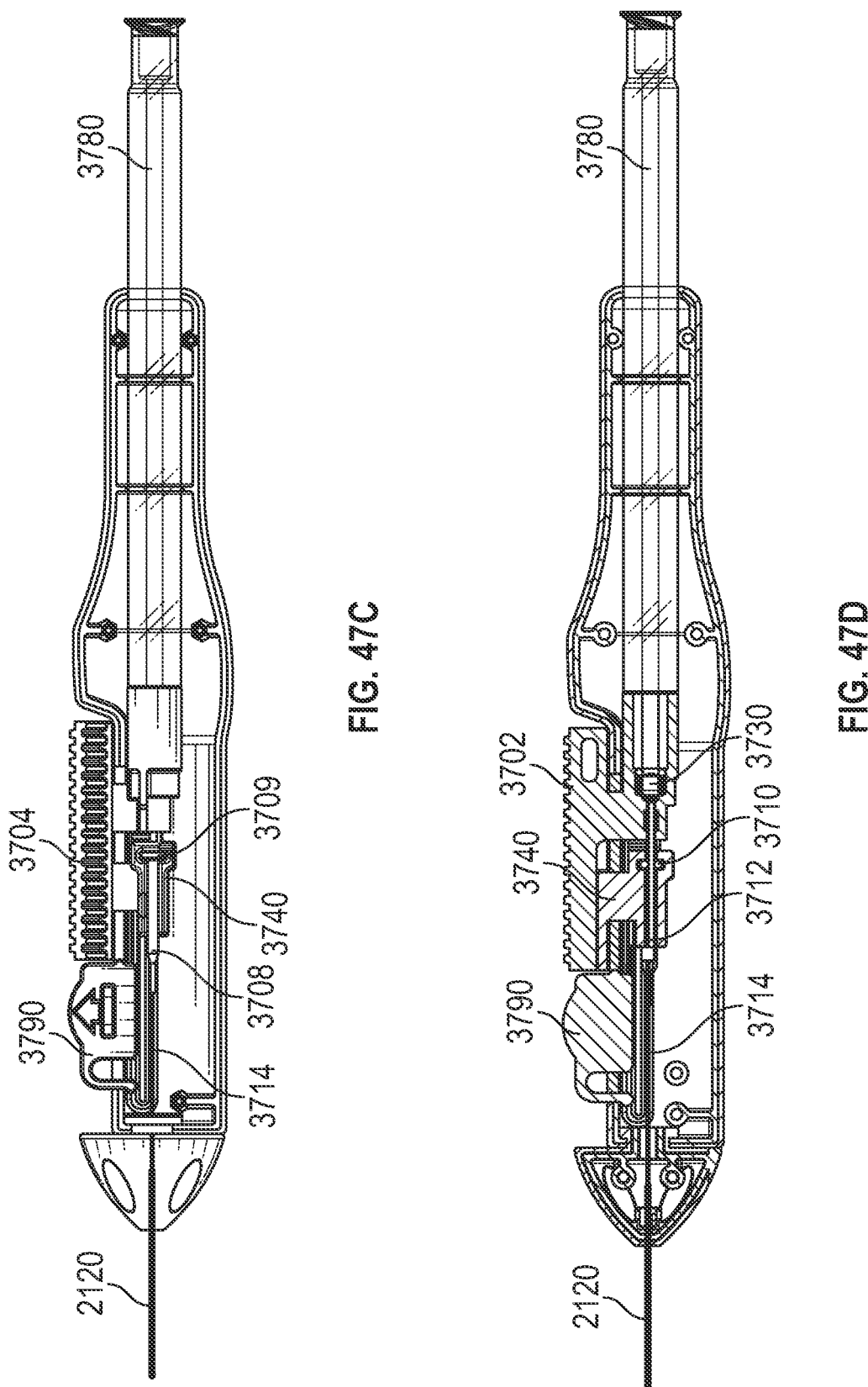
FIGS. 47C-47D depict cross-sectional views of the cannula adapter of FIG. 47A.
Figure 47E:
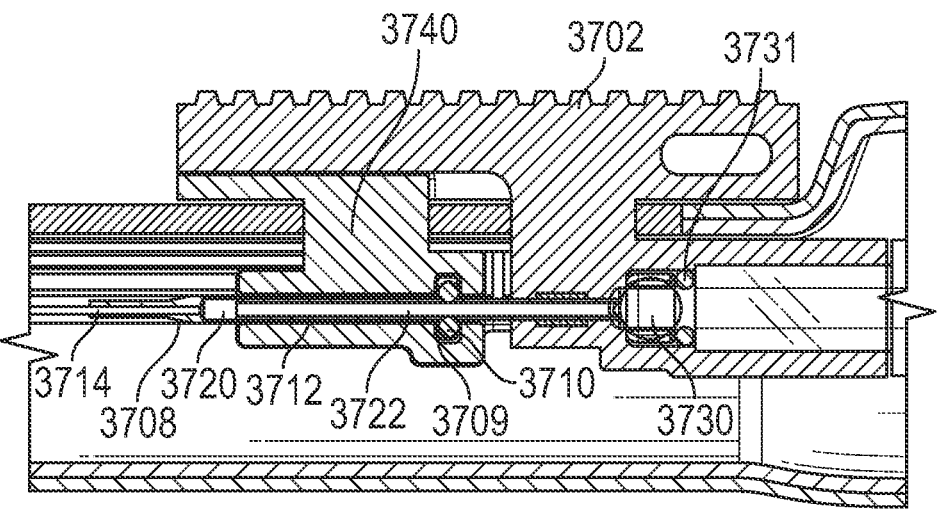
FIG. 47E depicts an enlarged, cross-sectional view of the cannula adapter of FIG. 47A as indicated in FIG. 47D.

The fluid delivery conduit 3716 can include a proximal base 3709, a body 3708, and a tube 3714. The fluid delivery conduit 3716 can be positioned within the insert 3740 of the second slider 3704 (as shown in FIG. 47H). In some implementations, at least a portion of the body 3708 and the base 3709 is positioned within the insert 3740 of the second slider 3704. The tube 3714 of the fluid delivery conduit 3716 can be operably coupled with the catheter 2115 such that distal and proximal movement of the fluid delivery conduit 3716 can distally or proximally move the catheter 2115. In some implementations, the tube 3714 is directly connected to the catheter 2115. In some implementations, the tube 3714 is connected indirectly to the catheter 2115 via an intervening tube. The tube 3714 is fluidly coupled to the catheter 2115.

The fluid delivery conduit 3716 can allow fluid (e.g., viscoelastic fluid) to flow from the reservoir 3780 to the catheter 2115. As shown in FIGS. 47D and 47E, the body 3708 of the fluid delivery conduit 3716 can include a bore 3720 that can receive the plunger 3712 that can slide within the bore 3720 of the body 3708. The plunger 3712 can include a lumen 3722 that can allow fluid (e.g., viscoelastic fluid) to flow through the plunger 3712, into the bore 3720 of the fluid delivery conduit 3716, and through the tube 3714 towards the catheter 2115.

During operation, the first slider 3702 and the second slider 3704 can together move distally (e.g., towards the distal end 3706) along the channel 3703. As described herein, the distal movement of the second slider 3704 can cause distal movement (e.g., moving towards the distal end 3706) of the fluid delivery conduit 3716, which can in turn cause the catheter 2115 to move distally and out of the cannula 2120. With reference to the example illustrated in FIG. 1F, an operator can penetrate a superior trabecular meshwork (TM) portion with the distal portion 2121 of the cannula 2120 and slide the first slider 3702 and the second slider 3704 to guide the catheter 2115 out of the cannula 2120 and into the Schlemm's canal (SC).

Once the catheter 2115 is extended out of the cannula 2120 (e.g., guided into the Schlemm's canal (SC)), the first slider 3702 can be used to dispense fluid (e.g., viscoelastic fluid) stored in the reservoir 3780. To dispense fluid stored in the reservoir 3780, the first slider 3702 may be moved proximally along the channel 3703 (e.g., away from the distal end 3706) and subsequently moved distally (e.g., towards the distal end 3706) along the channel 3703 relative to the second slider 3704. In some implementations, the second slider 3704 remains stationary (e.g., to ensure that the catheter 2115 does not move) while the first slider 3702 is moved along the channel 3703 to dispense fluid (e.g., the fluid 2126) stored in the reservoir 3780. When the first slider 3702 is moved proximally along the channel 3703 relative to the second slider 3704, the plunger 3712 can move proximally within the bore 3720 of the body 3708 of the fluid delivery conduit 3716. The proximal movement of the plunger 3712 (e.g., relative to the fluid delivery conduit 3716) within the bore 3720 can cause the fluid stored in the reservoir 3780 to flow past a ball 3730 and a gasket 3731, into the lumen 3722 of the plunger 3712, and into the bore 3720 of the fluid delivery conduit 3716. Once the fluid flows into the bore 3720 of the fluid delivery conduit 3716, the plunger 3712 can moved distally along the channel 3703 to force the fluid out from the bore 3720 and into the tube 3714. In some implementations, the ball 3730 (and the gasket 3731) can limit the amount of fluid flowing from the reservoir 3780 and into the lumen 3722 of the plunger 3712.

In some implementations, an operator (e.g., a clinician, surgeon, care provider) can change the amount of dispensed fluid by changing the distance travelled by the first slider 3702 along the channel 3703. For example, the further the first slider 3702 is moved proximally (e.g., towards the operator) along the channel 3703, the more fluid is dispensed via the catheter 2115, and vice versa. In some implementations, the channel 3703 (or the first slider 3702) can include detents that can provide tactile feedback as to how far the first slider 3702 is moved proximally (e.g., towards the operator) along the channel 3703 to indicate how much fluid will be dispensed once the first slider 3702 is moved back distally along the channel 3703.

The ball 3730 and the gasket 3731 can together function as a check valve for the plunger 3712. The ball 3730 and the gasket 3731 can allow the fluid (e.g., the fluid 2126) to be dispensed from the reservoir 3780 while preventing fluid (e.g., the fluid 2126) from flowing backwards (e.g., towards the reservoir 3780) past the ball 3730 and the gasket 3731. As such once the fluid flows past the ball 3730 and the gasket 3731, it cannot flow back into the reservoir 3780. In some implementations, other types of suitable valves may be used to provide unidirectional flow of the fluid (e.g., the fluid 2126) out of the reservoir 3780 and through the plunger 3712.

In some implementations, a user may experience increased resistance when sliding the second slider 3704 back and forth to dispense the fluid from the reservoir 3780 than when sliding both the first slider 3702 to move the catheter 2115 out of the cannula 2120. The resistance may be caused by greater friction between the second slider 3704 and the first slider 3702 (and the channel 3703) than between the first slider 3702 and the channel 3703. This difference in resistance can provide, for example, tactile feedback that can allow a user to distinguish the catheter dispensing motion (e.g., sliding the first slider 3702) and the fluid dispensing motion (e.g., sliding the second slider 3704).

In some implementations, the second slider 3704 can include a groove 3705 through which the first slider 3702 can move (e.g., slide) distally or proximally. The first slider 3702 and the second slider 3704 can include ridges 3752 and grooves 3750 that can provide better grip for an operator (e.g., care provider).

Figure 47F:
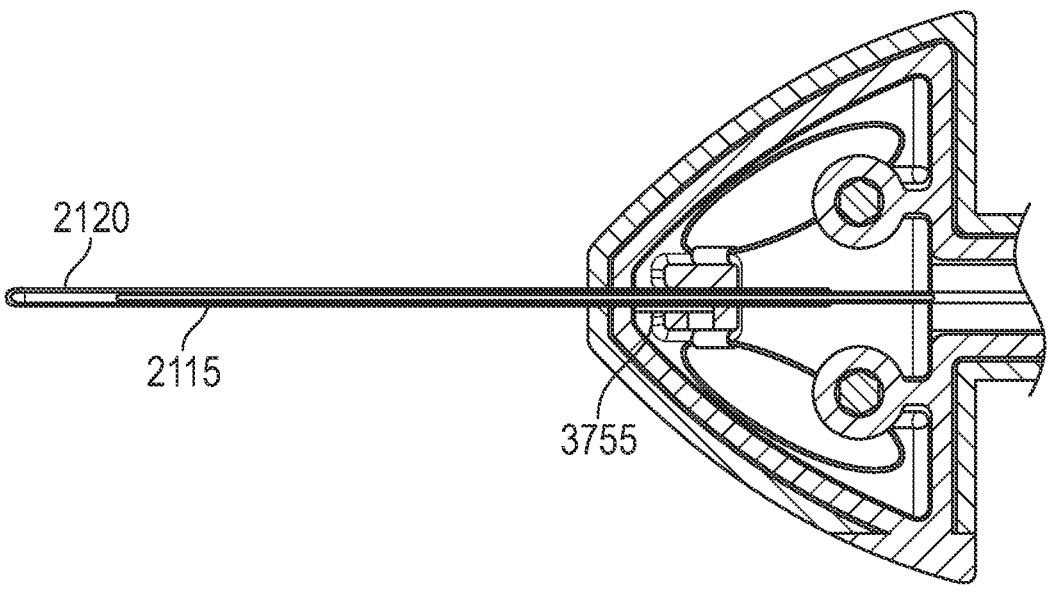
FIG. 47F depicts an enlarged, cross-sectional view of a tip of the cannula adapter of FIG. 47A.
Figure 47G:
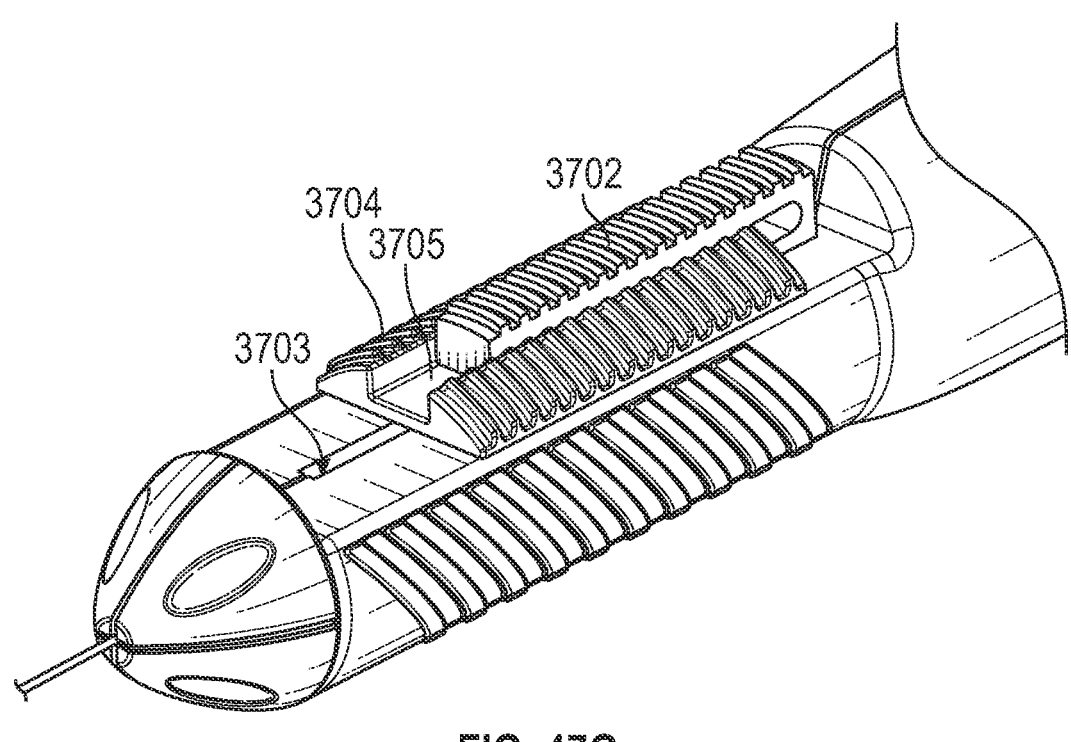
FIG. 47G depicts a perspective view of the cannula adapter of FIG. 47A without a locking pin.
Figure 47H:
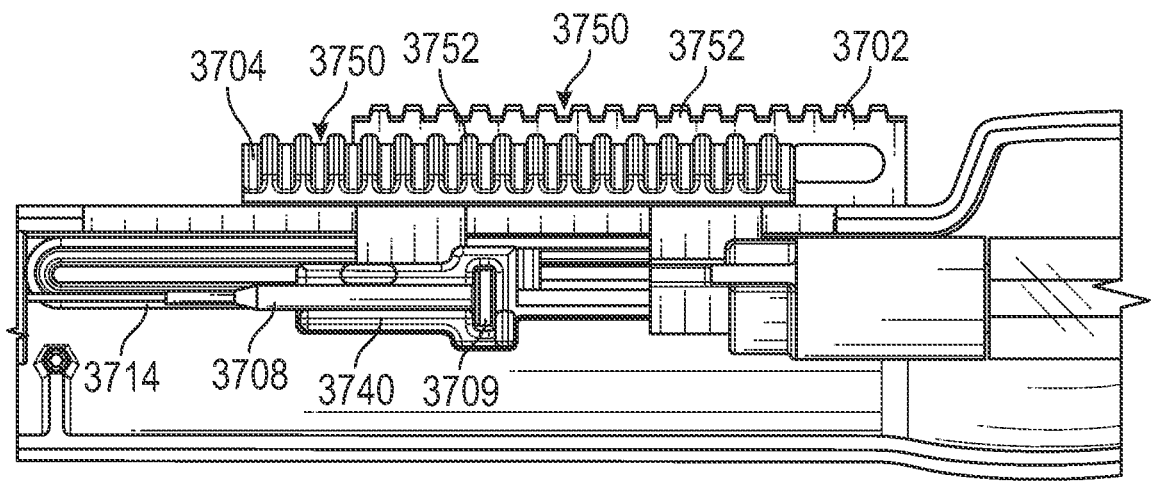
FIG. 47H depicts a cross-sectional view of the cannula adapter of FIG. 47G.
Figures 48A, 48B, 48C, 48D:
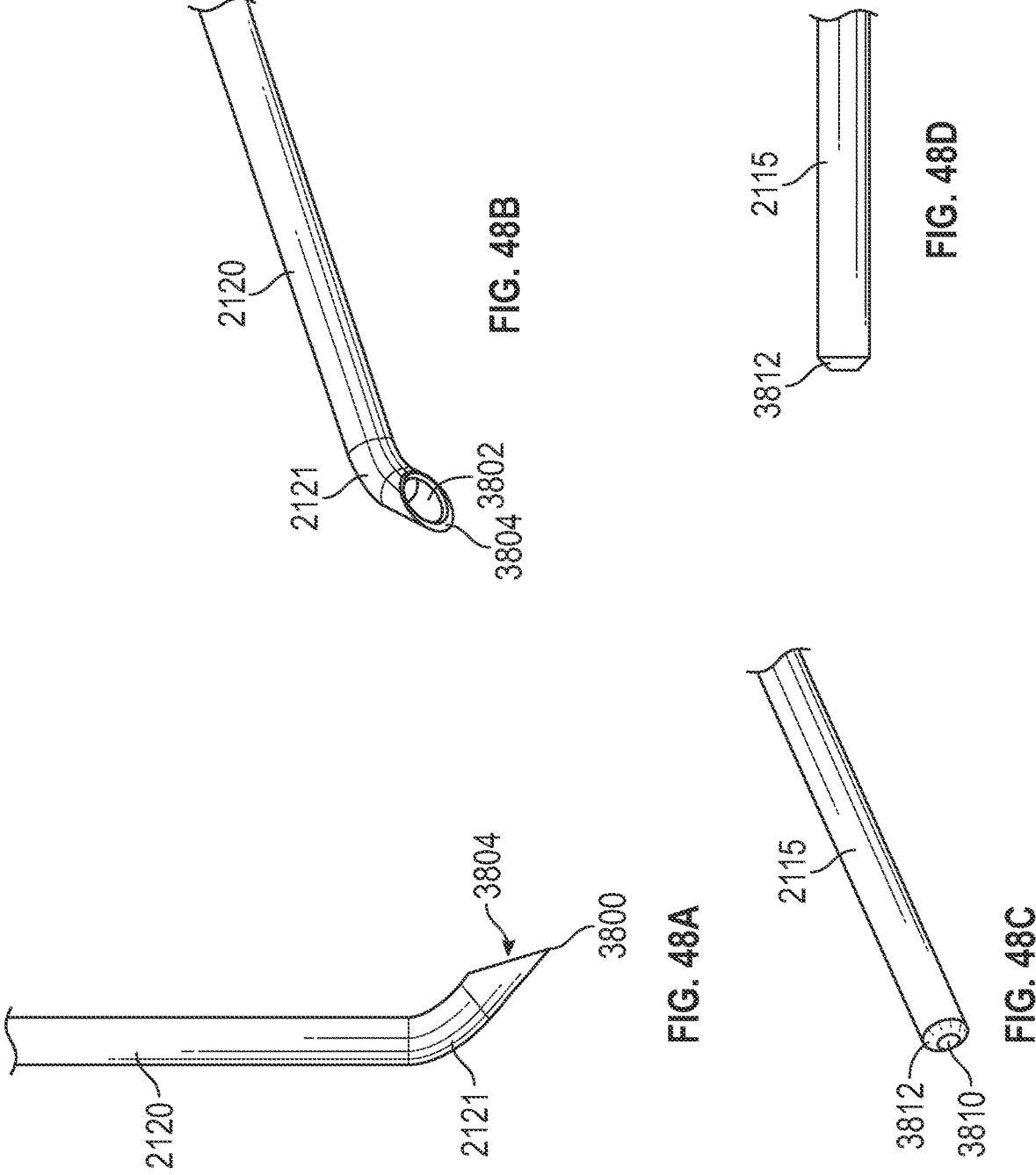
FIGS. 48A-48B depict various views of an outer cannula that may be incorporated into any of the embodiments of the cannula adapters.
FIGS. 48C-48D depict various views of an inner catheter that may be incorporated into any of the embodiments of the cannula adapters.

In some implementations, the cannula 2120 can include a protrusion 3755 that can fixedly attach the cannula 2120 to an insert formed inside the distal end 3706 (as shown in an example illustrated in FIG. 47F). As such, the distal end 3706 can be rotated to change the orientation of the cannula 2120 and therefore the orientation of the distal portion 2121 of the cannula 2120. This can advantageously allow an operator to change the orientation of the cannula 2120 by rotating the distal end 3706 without having to change the orientation (e.g., rotating about an axis parallel with the length of the cannula adapter) of the cannula adapter 3700.

The cannula adapter 3700 can include a stopper 3790 that can be placed inside the channel 3703. The stopper 3790 can prevent distal movement of the first slider 3702 and the second slider 3704 during, for example, storage or operation. This can advantageously prevent the catheter 2115 from accidentally or inadvertently extending out from the cannula 2120.

As shown in an example in FIG. 47E, a gasket 3710 may be placed inside the base 3709 of the fluid delivery conduit 3716. The gasket 3710 may be dimensioned to fit snugly within the base 3709 and include an opening (e.g., circular opening) to receive the plunger 3712. In some implementations, the gasket 3710 can contact the outer surface of the plunger 3712 to generate sufficient resistance to cause smooth, controlled movement of the plunger 3712 within the bore 3720 of the body 3708.

FIGS. 48A-48D illustrate various views of the cannula 2120 and the catheter 2115. As described herein, the cannula 2120 can include the distal portion 2121 that can penetrate a superior trabecular meshwork (TM) portion with a tip 3800 and an end surface 3804. The end surface 3804 may be formed at an angle (e.g., slanted) with respect to an axis parallel to the body of the cannula 2120. The surface 3804 can facilitate, for example, penetration of a superior trabecular meshwork (TM) portion. In some implementations, the end surface 3804 may be orthogonal (or substantially orthogonal) with respect to an axis parallel to the body of the cannula 2120. The tip 3800 may form a beveled distal tip to facilitate a cutting edge. The distal portion 2121 may be curved to allow the catheter 2115 to extend out (e.g., exit) from the lumen 3802 of the cannula 2120 at an angle, which can facilitate movement of the catheter 2115 into and around the Schlemm's canal (SC). The catheter 2115 can include a distal end 3810 (e.g., tip) having a tapered edge 3812. The tapered edge 3812 can facilitate and guide movement of the catheter 2115 within the curved distal portion 2121 and inside the Schlemm's canal (SC).

FIGS. 48E-48H illustrate other examples of the distal portion 2121 of the cannula 2120. The distal portion 2121 can include one or more cutouts 3852 that can be formed at the tip 3800 of the distal portion 2121 to provide one or more cutting edges or surfaces. In some implementations, the cutouts 3852 can be formed on a distal edge (e.g., the edge further from a portion of the cannula 2120 proximate to the distal portion 2121) of the distal portion 2121. In some implementations involving multiple cutouts 3852, the cutouts 3852 can be formed adjacent to one another (e.g., as shown in FIGS. 48G and 48H). The cutouts 3852 can include anchors 3854 that can abut against a surface (e.g., the back wall of Schlemm's canal) and stabilize the cannula 2120 (e.g., prevent the distal portion 2121 of the cannula 2120 from moving around) during dispensing of the fluid via a catheter (e.g. the catheter 2115). In some implementations, the anchors 3854 can, during use, penetrate a tissue surface (e.g., the back wall of Schlemm's canal). The distal portions 2121 described herein and shown in FIGS. 48E-48H may be incorporated in any implementations of the cannula 2120 described herein.

Figures 49A, 49B:
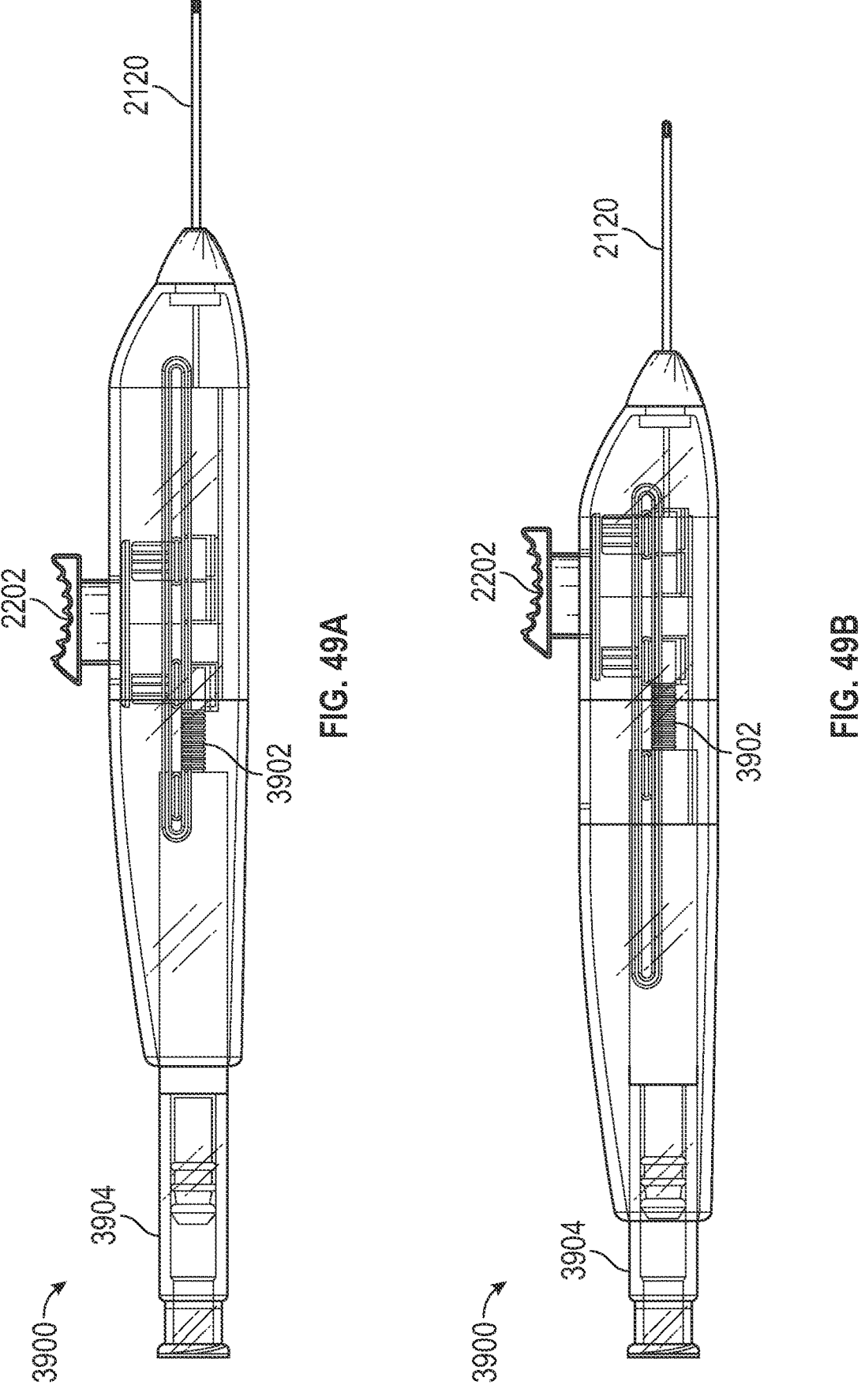
FIGS. 49A-49B depict an example operation scheme of another embodiment of a cannula adapter.

FIGS. 49A and 49B illustrate an example operation scheme of a cannula adapter 3900. The cannula adapter 3900 can include the slider 2202, the cannula 2120, a dispensing mechanism 3902 and a reservoir 3904. An operator can slide the slider 2202 distally (e.g., towards the patient) to guide, for example, the catheter out of the cannula 2120 and into the Schlemm's canal. Subsequently, the operator can actuate the reservoir 3904 to dispense fluid into and out of the catheter 2115. In some implementations, the dispensing mechanism 3902 may include a fixed plunger positioned within the reservoir 3904 that pushes the fluid out of the reservoir 3904 when the reservoir 3904 rotated about an axis parallel to the length of the cannula adapter 3900. In some implementations, the dispensing mechanism 3902 may include a plunger positioned within the reservoir 3904 and connected to an elastic member (e.g., a spring) that can push the fluid out of the reservoir 3904 and towards the catheter 2115 when, for example, a proximal end of the reservoir 3904 is pushed distally (e.g., towards the patient).

In accordance with several implementations, Trypan blue or some other biocompatible dye (e.g., brilliant blue, indocyanine green, fluorescein) into the reservoir 2164, prior to filling. Introducing biocompatible dye may allow the operator to visualize the extent of dilation in Schlemm's canal and the downstream episcleral venous network.

Several additional features may be integrated with the above concepts. For example, wound sealing features outside of the outer cannula 2120 or introducer needle, such as a compliant/elastomer overmold or o-ring that fits within or presses against the corneal incision during surgery to prevent aqueous humor leakage. Alternatively, a balanced salt solution (BSS) infusion path through the outer cannula 2120 may be used to provide chamber stability.

Although primarily described with respect to delivery of viscoelastic within Schlemm's canal, the devices and methods described and illustrated herein could be used in connection with delivery of viscoelastic or other fluid to other pre-existing or created anatomical passages, channels, spaces, lumens, or vessels either associated with the eye (e.g., collector channels, downstream episcleral venous networks, tissue tracts of the eye, suprachoroidal space, sub-conjunctival space, subretinal space) or in other locations other than the eye. Fluids other than viscoelastic may be used (e.g., other liquid drug, medicament, solution, chemical, etc.).

In aspects of the disclosure, an ophthalmic viscosurgical device (OVD) may be connected to a device through a tube with nurse activated delivery.

In aspects of the disclosure, an OVD may be provided as a pen cap OVD for viscoelastic solution used in eye surgery. For example, a unitary handle having a fluid reservoir located entirely therein. As another example, an OVD may come prepackaged in an attachable (e.g., click on) device, where it may click on to the handle or connect via the needle. Further click on OVD devices may connect via a needleless connector using a duckbill valve, a spiked valve or a maxplus valve. In some examples, an OVD may be loaded into a cartridge in the operating room and then the cartridge may click on to the device.

Figure 50:
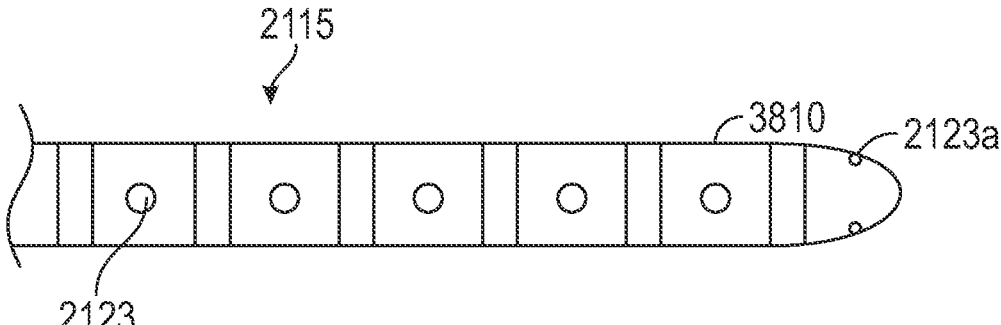
FIG. 50 depicts a schematic example of a tip of an ophthalmic device.

In aspects of the disclosure, an ophthalmic device (e.g., cannula adapter 3900, ophthalmic device 4000) may be provided in which a distal end 3810 (e.g., tip) of a catheter 2115 or even an entire length of the catheter 2115 has side ports 2123 (e.g., holes), or the catheter 2115 is porous or woven (e.g., like a cardiac stent). Here, a very distal end 3810 may have no hole or a hole 2123*a* sized (see FIG. 50) to allow build up of pressure within the catheter 2115 such that viscoelastic solution flows through the wall of the catheter 2115 and creates pressure around the catheter 2115 (e.g., inside Schlemm's canal, stretches trabecular meshwork, dilates collector channels).

Figure 51:
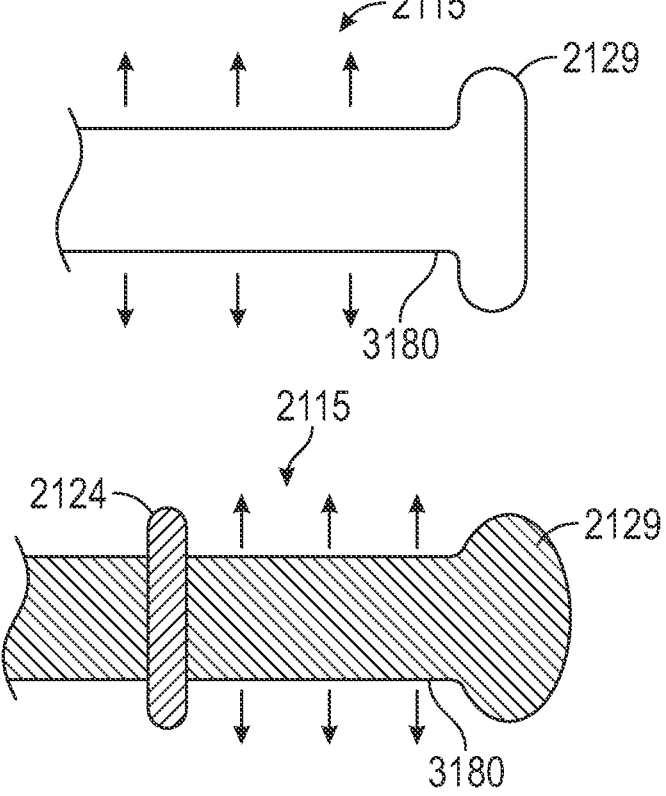
FIG. 51 depicts schematic examples of fluid flow from a tip of an ophthalmic device with and without a barrier.

In aspects of the disclosure, o-rings 2124 may create zones of constrained fluid (e.g., local pressure build up) as shown in FIG. 51. In aspects of the disclosure, a sinusoidal outer diameter may be used instead of or in addition to o-rings 2124. As shown in the top figure of FIG. 51, an OVD 2129 is lateral to the tip 3810 of the catheter 2115 and the viscoelastic solution (e.g., viscous fluid) flows outward from the catheter 2115/cannula 2120. As shown in the bottom figure of FIG. 51, an o-ring 2124 acts as a barrier to outflowing viscous fluid from flowing further back along the catheter 2115/cannula 2120, so provides pressure to the area between the tip 3810 and the o-ring barrier. Another method is to press down with the external tip 3810 of the device (e.g., press down on TM) to create a reservoir and then pump in fluid to inflate.

In aspects of the disclosure, an ophthalmic device is inserted trans luminal (e.g., enter through AC), the catheter/cannula enters through the TM, and the catheter extends along the SC. The tip of the device has the ability to deliver fluid when the catheter is stationary, is standing, or is retracting. The tip of the device may deliver fluid radially (e.g., distance equal to 1-2 clock hours).

In aspects of the disclosure, an o-ring, a gasket or a larger flexible tube may create a constrained area for localized high pressure, which may target specific anatomy (e.g., towards collector channels or towards TM). Other features that may affect the ophthalmic device are handset design, catheter exentsion/retraction, fluid delivery and pressure regulation, and a detachable fluid reservoir.

In aspects of the disclosure, an ophthalmic device may be suitable to deliver one or more drugs instead of or in combination with OVD.

In aspects of the disclosure, an ophthalmic device may include a catheter that is severable from the device to become an ocular implant. For example, the ophthalmic device may be used to deploy a catheter, deliver OVD and/or drug(s) and sever the catheter from the handset (e.g., where catheter enters TM). The remaining un-severed catheter is bio-adsorbable, so it is not used as a long term implant. The severed part of the catheter is suitable as a long term implant.

Figure 52:
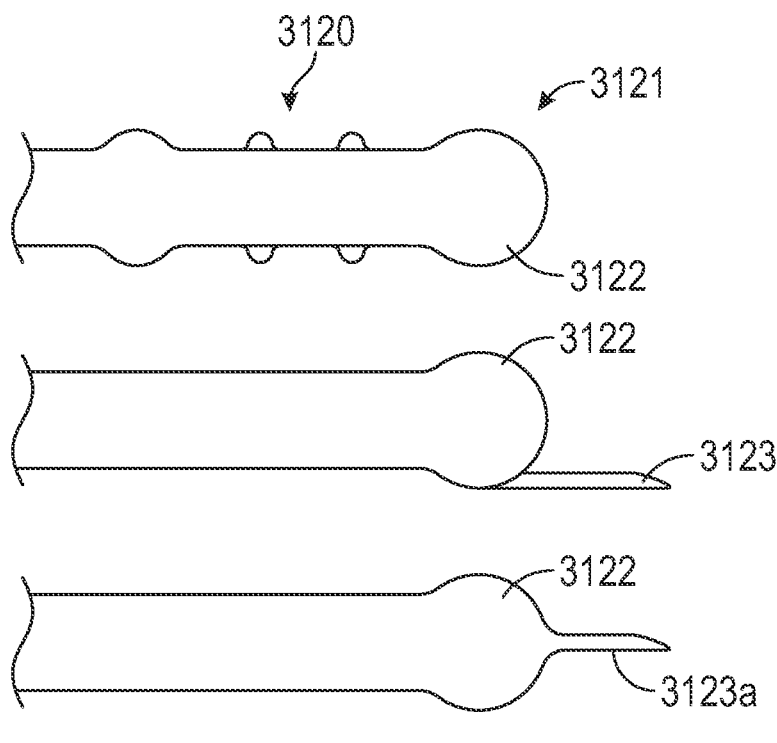
FIG. 52 depicts schematic examples of various tips of an ophthalmic device.

With current canaloplasty catheters, one of the issues is getting the catheter 3120 directed into the canal easily. The catheter leading bulb 3122 (see top figure of FIG. 52) often ends up riding over the TM instead of under it. In aspects of the disclosure, an ophthalmic device 3900 may include a leading feature 3123 disposed on a bulb 3122 of the distal tip 3121 to allow the catheter 3120 to go into the canal more easily and the rest will then follow. For example, the leading feature 3123 may be a flat surface (e.g., like a shoe horn) that enters first as shown in the middle figure of FIG. 52. Here, the flat part 3123 would be against the anterior wall of the canal. The leading feature 3123 may also be a point as shown in the bottom figure of FIG. 52. In aspects of the disclosure, the leading feature 3123 can be used for initial entry into the canal (e.g., supported in part by an inserter that holds this flat edge in rigid fashion so that it engages the TM firmly but is still supported by the surrounding metal of the inserter itself), rather than the current methods of using a blade to make the initial slit or using the inserter tip to make the initial stab incision.

Figure 53:
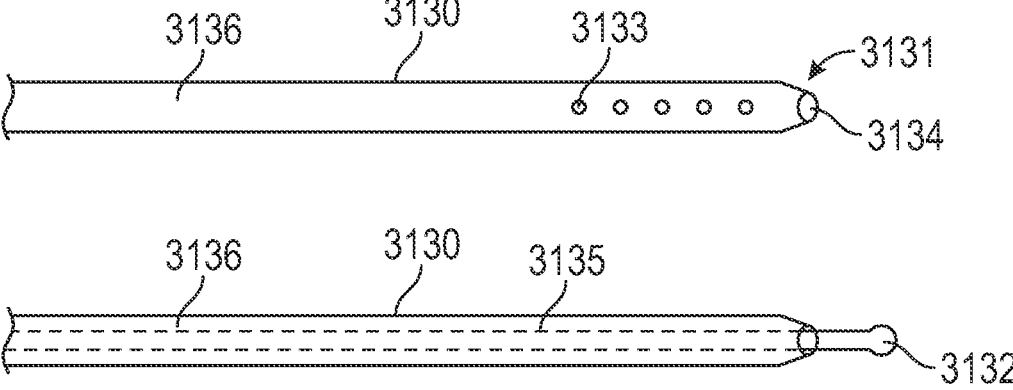
FIG. 53 depicts schematic examples of a catheter with fluid dispersing orifices and with a suture disposed within the catheter.

As shown in FIG. 53, a catheter 3130 may be used for multiple purposes, such as for injecting fluid and also for feeding/injecting and placing a suture. For example, as shown in the top depiction of FIG. 53, the catheter 3130 may have a distal hole 3134 (e.g., hole at the leading end 3131) that provides for passing fluid (e.g., viscous) out the distal hole 3134, as well as out the orifices 3133 on the side walls of the catheter 3130. As shown in the bottom depiction of FIG. 53, a suture 3135 may be disposed within the catheter lumen 3136 and an end bulb 3132 of the suture 3135 may be flush with and/or plug the distal hole 3134 of the catheter 3130. Any suitable structure may be used instead of an end bulb, such as a hook for example. Here, with the bulb 3132 of the suture 3135 capping off the distal hole 3134, any fluid flushed through the lumen 3136 around the suture 3135 within the lumen 3136 would flow out the orifices 3133 on the side of the catheter 3130. In aspects of the disclosure, the fluid flushing operation of the catheter 3130 may be conducted and then the suture 3135 may be inserted in the catheter 3130 to inject/place the suture 3135, or vice versa.

In aspects of the disclosure, the catheter 3130 may be inserted 360 degrees within the canal of Schlemm, then the bulb 3132 of the suture 3135 may be fixed while the catheter 3130 is withdrawn, thus leaving the suture 3135 behind while removing the catheter 3130 from the eye. Here, the suture 3135 may be tied off or the suture 3135 may be just left in place, for example. In aspects of the disclosure, once the 360 degree insertion is complete, the catheter 3130 may be cut and left in place. In aspects of the disclosure, the catheter 3130 may be inserted first to do viscous dilation by injecting viscous, then the catheter 3130 may be removed and a suture 3135 may be inserted 360 degrees and left in place. Here, a device handpiece may be used to insert the catheter 3130, then the catheter 3130 may be replaced in the device handpiece by the suture 3135 so that the suture 3135 can be inserted/placed using the same device handpiece. For example, after use the catheter 3130 may be retracted back into a stainless steel sleeve and the suture 3135 may then be fed out of the stainless steel sleeve. In aspects of the disclosure, the device handpiece may be configured for only introducing a suture 3135 and not for using a catheter 3130.

In aspect of the disclosure, the suture 3135 may be affixed to the outside of the catheter 3130 instead of being disposed within the lumen 3136 of the catheter 3130. This provides an advantage that the catheter 3130 may be inserted once and used for both viscous dilation and suture 3135 placement. In aspects of the disclosure, as shown in FIG. 54, the catheter 3130 may have an axial indentation 3137 (e.g., slot) in the exterior side wall so that the suture 3135 may be disposed in the indentation 3137 such that the combined diameter of the catheter 3130 and the suture 3135 within the slot 3137 is the same as the diameter of a typical catheter. In aspects of the disclosure, the catheter 3130 may have an outer ring indentation 3138 to tie the suture 3135 around if needed or desired.

As shown in FIG. 55, in aspects of the disclosure the bulb 3132 of the suture 3135 may merge with a suture ring 3139 to lock the suture 3135 in place. For example, the suture ring 3139 may be at one end of the 360 degree loop and the bulb 3132 may be at the other end of the 360 degree loop so that once the bulb 3132 and the ring 3139 are merged the 360 suture loop remains in position.

As shown in FIG. 56, in aspects of the disclosure the suture 3135 may be configured as a waveform. Here, a waveform suture 3135 provides for bunching or tensing up the TM independent of tying or tensioning the suture. The suture 3135 may have barbs as shown in FIG. 57, which provide for maximizing tensile or anchoring strength of the suture 3135.

As shown in FIGS. 58A-58D, in aspects of the disclosure a guidewire 4140 and a tensioning suture 4135 may be inserted into an eye 115. As shown in FIG. 58A, a cannula 4120 of an ophthalmic device 4000 (FIG. 64) may be inserted into the eye 115 and aligned with the canal 108 (e.g., Schlemm's Canal). A guidewire 4140 may then pierce the canal 108 and be extended to track through the canal 108 to encircle a perimeter of the eye 115, as shown in FIG. 58B. As shown in FIG. 58C, a catheter 4150 may be inserted and extended to follow the guidewire 4140 around the perimeter through the canal 108. In aspects of the disclosure, the catheter 4150 may inject or dispense fluid (e.g., visco) as it is moved through the canal 108. The guidewire 4140 may then be disconnected from the ophthalmic device 4000, leaving the guidewire 4140 positioned throughout the canal

108 encircling the eye 115, as shown in FIG. 58D. Here, the disconnected guidewire 4140 may provide an inward tension.

In aspects of the disclosure, the guidewire 4140 may be set into a shape slightly smaller that the diameter of the canal 108. In aspects of the disclosure, the guidewire 4140 may be formed of any suitable material (e.g., super-elastic nitinol). In aspects of the disclosure, the guidewire 4140 may be extended greater than 360 degrees so that the ends of the guidewire 4140 are overlapped, as shown in FIG. 58D, in order to avoid or minimize stress concentration and/or tearing at the ends of the guidewire 4140. In aspects of the disclosure, the catheter 4150 may be extended through the canal 108 around the perimeter of the eye 115 prior to insertion of a wire 4170 (FIG. 59), such as if guiding the catheter 4150 by guidewire 4140 is not beneficial. Here, the wire 4170 may be deployed after the catheter 4150 is fully inserted.

In aspects of the disclosure, a simple push wire 4160 may be supported by the interior diameter of the catheter 4150 in order to deploy the wire 4170 (e.g., extend the wire 4170 through the canal 108), as shown in FIG. 59. Here, the push wire 4160 may not be retractable into the catheter 4150, so any suitable manner of cutting or breaking the push wire 4160 and/or wire 4170 may be used in order to leave the push wire 4160 and/or wire 4170 behind in the canal 108.

As shown in FIGS. 60A and 60B, any suitable tensioning device 4180 may be used as the wire implanted into the canal 108 of the eye 115. For example, the tensioning device 4180 may be a shape memory polymer helical coil suture 4180*a* that is deployed into the canal 108, whereupon body temperature in the eye 115 may activate the suture 4180*a* and cause it to contract in an arch against the trabecular meshwork 106 and stretching the suture 4180*a* towards the anterior chamber 100.

Figure 62A:
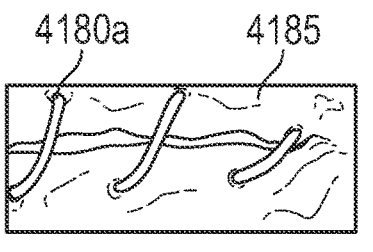
FIGS. 62A-62C depict a tensioning device at different levels of contraction.
Figure 62B:
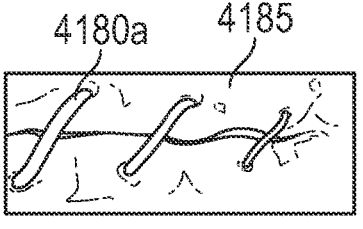
Figure 62C:
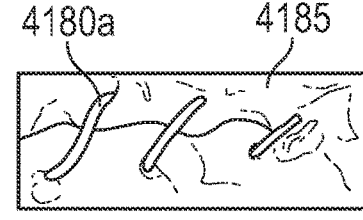

As shown in FIGS. 62A to 62C, a helical coil suture 4180*a* disposed in tissue 4185 is shown in various stages of contraction. Here, the shape memory polymer suture 4180*a* in FIG. 62A may have just been placed in the canal 108 and thus may be at a temperature of 20 degrees Celsius. In FIG. 62B, the body temperature in the eye 115 may warm the shape memory polymer suture 4180*a* to 37 degrees Celsius, causing the shape memory polymer suture 4180*a* to contract. The shape memory polymer suture 4180*a* may contract further when the temperature rises to 40 degrees Celsius, as shown in FIG. 62C, for example.

Figure 61:
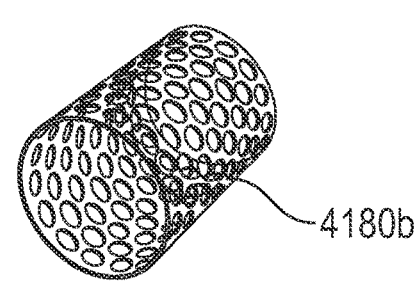
FIG. 61 depicts a tensioning device.

As shown in FIG. 61, the tensioning device 4180 may be a shape memory polymer tube 4180*b* that expands when deployed into the canal 108. Here again, the body temperature of the eye 115 activates the shape memory polymer tube 4180*b* to expand against the canal 108 and stretch the trabecular meshwork 106 and stretching the shape memory polymer tube 4180*b* towards the anterior chamber 100. In aspects of the disclosure, the tensioning device 4180 may be a nitinol wire overmolded in silicone, for example.

Figure 63A:
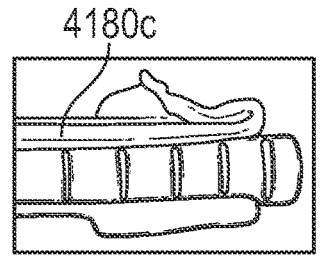
FIGS. 63A-63C depict another tensioning device at different levels of contraction.
Figure 63B:
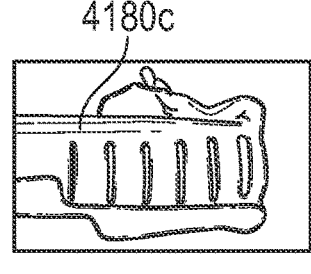
Figure 63C:
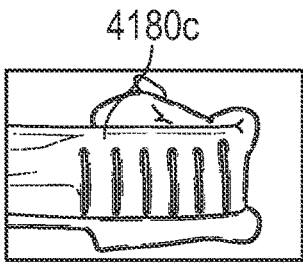

In yet another example as shown in FIGS. 63A-63C, the tensioning device 4180 may be a shape memory polymer cylindrical device 4180*c*. As shown in FIG. 63A, the shape memory polymer cylindrical device 4180*c* may be in a temporary packaged state (e.g., at initial placement in the canal 108). In FIG. 63B, the shape memory polymer cylindrical device 4180*c* may be in a partially recovered state (e.g., after activation by the body temperature of the eye 115). In FIG. 63C, the shape memory polymer cylindrical device 4180*c* may be in a fully recovered state (e.g., after full activation by the body temperature of the eye 115).

In aspects of the disclosure, the tensioning device may be formed of shape memory polymers and/or shape memory alloys. In aspects of the disclosure, the tensioning device may be an injectable bio erodible or biodegradable stenting device that dissolves or vanishes after a set period of time (e.g., 1 week or longer).

In aspects of the disclosure, the tensioning device may be a suture folded in on itself at least once, braided or holding an architecture that allows for viscoelastic to bridge the suture material and be retained for follow on steps. In aspects of the disclosure, a viscoelastic may be placed onto the folded suture so that the viscoelastic is retained between the strands of the suture prior to placing the suture in the inserter and then inserting the combined suture and viscoelastic into the canal of Schlemm (e.g., the suture and the viscoelastic may both be inserted and retained in the canal long term).

In aspects of the disclosure, the shape memory tube and/or the shape memory suture may be selectively expandable along its length, wherein when a portion of the tube/suture along 90 degrees expands, portions of the tube/suture at 0 and 90 degrees may be pressed against the outer wall of Schlemm's canal while the portion of the tube/suture at 45 degrees may stretch the TM toward the AC.

In aspects of the disclosure, an ophthalmic device may include one or multiple lumens. In aspects of the disclosure, an ophthalmic device may include different sized slots and/or shaped holes. In aspects of the disclosure, an ophthalmic device may include delivery of OVD forward, backward, or both (e.g., relative to the tip). In aspects of the disclosure, an ophthalmic device may include a dynamic shaped front to help navigate through the canal. In aspects of the disclosure, an ophthalmic device may include click-wheel delivery (e.g., like on a computer mouse). In aspects of the disclosure, an ophthalmic device may include a dynamic delivery button (e.g., not a click but can titrate based on how far the button is pressed). In aspects of the disclosure, an ophthalmic device may include sealing feature(s) to help contain viscous fluid. In aspects of the disclosure, an ophthalmic device may include the ability to dial delivery volume on the handpiece.

Figure 64:
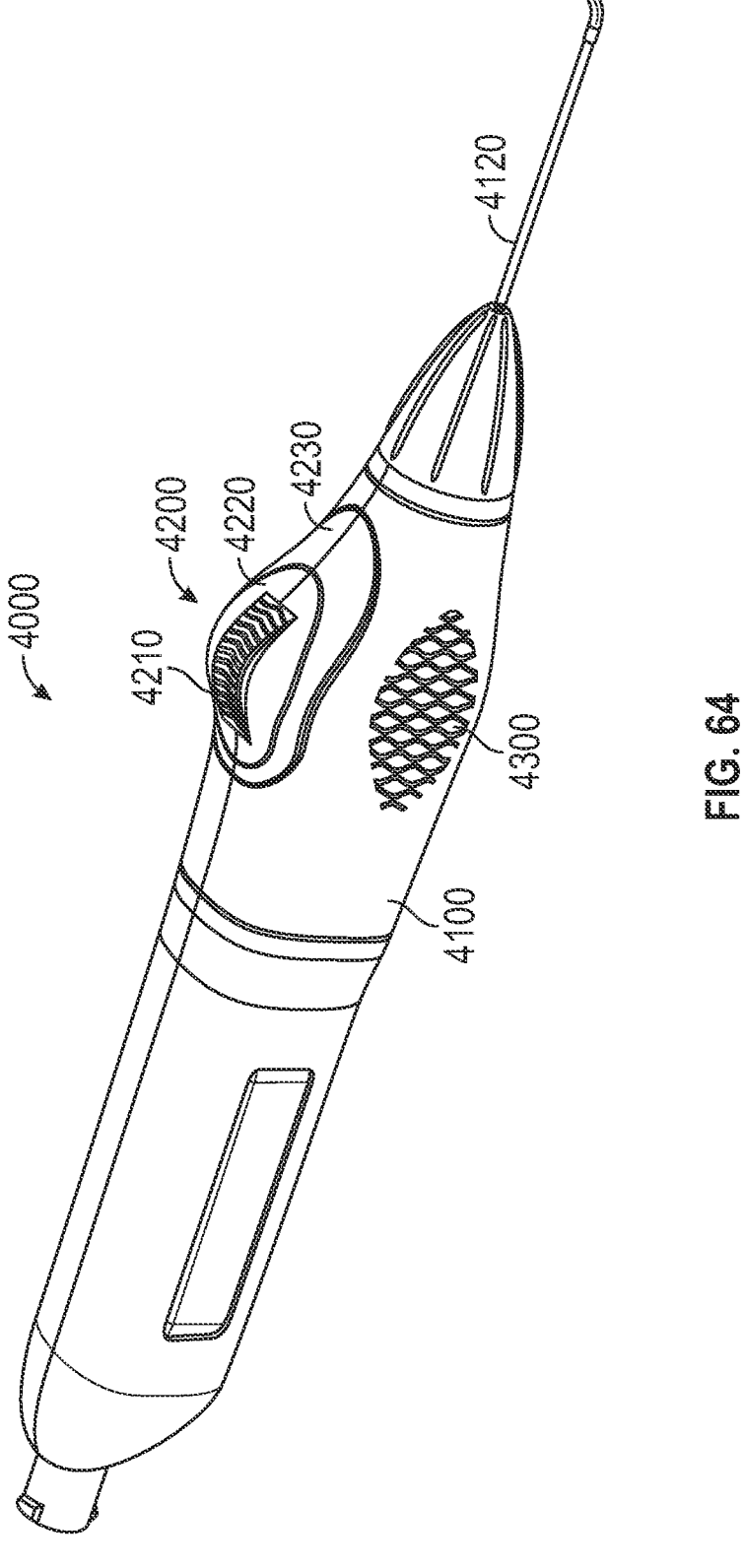
FIG. 64 depicts a perspective view of an ophthalmic device.

As shown in FIG. 64, an ophthalmic device 4000 has a housing 4100 and a cannula 4120 extending from the housing 4100. An activation assembly 4200 may be disposed on and/or within the housing 4100. The activation assembly 4200 may include a wheel 4210 (e.g., scroll wheel) configured to rotate around in place within the housing 4100. A movable housing ring 4220 may be disposed on the housing 4100 around some or all of the wheel 4210. The movable housing ring 4220 may be coupled to the wheel 4210 so that the movable housing ring 4220 and the wheel 4210 move in tandem when the wheel 4210 is pushed inward into the housing 4100.

A fixed housing ring 4230 may be disposed on the housing 4100 around some or all of the movable housing ring 4220. The fixed housing ring 4230 remains fixed to the housing 4100 and thus remains in a fixed position as the moveable housing ring 4220 moves inward and outward. For example, when the wheel 4210 is pushed inward or is biased outward (e.g., springs out) when pressure on the wheel 4210 is released. In aspects of the disclosure, the housing 4100 itself may be disposed on the around some or all of the movable housing ring 4220 instead of a fixed housing ring 4230.

A tactile portion 4300 may be disposed on the housing 4100 or may be formed as a part of the housing 4100. For example, the tactile portion 4300 may be a soft-touch rubber coating configured to provide for a solid and ergonomic grip on the ophthalmic device 4000. The tactile portion 4300 may be formed of any suitable material (e.g., rubber, silicone) and may be disposed on the housing 4100 by any suitable process (e.g., overmolding, molding, welding, adhesive).

In use, the ophthalmic device 4000 may be gripped by a user's hand, where rotation of the wheel 4210 may cause extension or retraction of a wire (e.g., guidewire 4140) or a catheter (e.g., catheter 4150) from or into the cannula 4120. For example, the user's finger or thumb may be used to scroll the wheel 4210 forward to extend a guidewire 4140 and/or a catheter 4150. Similarly, the wheel 4210 may be scrolled backwards in order to retract the guidewire 4140 and/or catheter 4150, for example. In addition, the user may push inward on the wheel 4210, causing the wheel 4210 and the moveable housing ring 4220 to displace inwards into the housing 4100, which may cause a pumping action to eject fluid through the cannula 4120, for example. In aspects of the disclosure, the above described use of ophthalmic device 4000 may be performed for any suitable reason unrelated to medical processes or treatment of a person, such as maintenance or testing of the ophthalmic device 4000. Accordingly, the ophthalmic device 4000 is not limited to medical treatment of a person, such as for medical treatment of a person's eye.

Thus, the activation assembly 4200 provides for multiple functions of the ophthalmic device 4000, such as advancing and/or retracting items (e.g., guidewire 4140, catheter 4150, tensioning device 4180) through the cannula 4120, as well as pumping fluid through the cannula 4120.

In some embodiments according to the disclosure, an ophthalmic device, comprises: a housing; a cannula extending from the housing, the cannula having a lumen for fluid flow; a reservoir for holding fluid; and an activation assembly, comprising: a rotatable wheel; and a moveable housing ring coupled to the wheel, wherein the rotatable wheel and the moveable housing ring are configured to move inward together towards an interior of the housing when a first force is applied inward on the wheel and to move outward together away from the interior of the housing when a second force is applied outward on one of the wheel and the moveable housing ring.

In some aspects of the disclosure, a fixed housing ring is fixedly coupled to the housing and moveably coupled to the moveable housing ring, wherein the moveable housing ring is configured to move inward and outward relative to the fixed housing ring. In some aspects of the disclosure, the housing comprises a fixed housing ring coupled to the moveable housing ring, wherein the moveable housing ring is configured to move inward and outward relative to the fixed housing ring. In some aspects of the disclosure, the rotatable wheel is configured to move a catheter through the cannula. In some aspects of the disclosure, the rotatable wheel is configured to move a wire through the catheter. In some aspects of the disclosure, the rotatable wheel is configured to move a wire through the cannula. In some aspects of the disclosure, the rotatable wheel is configured to move a tensioning device through the cannula. In some aspects of the disclosure, the rotatable wheel is configured to advance one of a catheter, a wire and a tensioning device when the rotatable wheel is rotated in a forward direction towards the cannula. In some aspects of the disclosure, the rotatable wheel is configured to retract one of a catheter, a wire and a tensioning device when the rotatable wheel is rotated in a rearward direction away from the cannula.

In some aspects of the disclosure, the activation assembly is configured to pump fluid through the lumen of the cannula when the coupled rotatable wheel and moveable housing ring are moved inward. In some aspects of the disclosure, the activation assembly is configured to draw fluid from the fluid reservoir when the coupled rotatable wheel and moveable housing ring are moved outward. In some aspects of the disclosure, a spring is coupled to one of the rotatable wheel and the moveable housing ring, wherein the spring is biased to provide the second force. In some aspects of the disclosure, the housing comprises a tactile portion that is one of formed with the housing and disposed on the housing, the tactile portion configured to provide an ergonomic grip.

In some aspects of the disclosure, a catheter is configured to slidably move through the cannula, the catheter comprising an internal lumen for fluid flow. In some aspects of the disclosure, a portion of the catheter comprises one or more side ports disposed in a wall of the catheter, the one or more side ports configured to provide fluid flow external to the catheter from the internal lumen. In some aspects of the disclosure, the catheter comprises one or more O-rings disposed around the catheter, the one or more O-rings configured to provide a constrained fluid zone external to the catheter. In some aspects of the disclosure, the catheter comprises a bulb disposed at a tip of the catheter, the bulb having a leading feature comprising one of a flat surface extending from the bulb and a pointed portion extending from the bulb. In some aspects of the disclosure, the catheter comprises a hole disposed at a tip of the catheter, the hole configured to provide one of: fluid passage from the internal lumen; slidable movement of a suture disposed within the internal lumen; and slidable movement of a tensioning device disposed within the internal lumen. In some aspects of the disclosure, the catheter comprises an axial indentation disposed in an external surface of a catheter wall, the axial indentation configured to receive one of a suture and a tensioning device.

In some embodiments according to the disclosure, a method of operating an ophthalmic device comprises: gripping a housing of the ophthalmic device; applying a rotational force to a wheel of an activation assembly of the ophthalmic device; slidably moving one of a catheter, a wire and a tensioning device through a cannula of the ophthalmic device based on the rotational force; applying an inward orthogonal force to the wheel; moving the wheel and a moveable housing ring coupled to the wheel inward together towards an interior of the housing based on the inward orthogonal force; pumping fluid through a lumen of the cannula based on the inward movement of the coupled wheel and moveable housing ring; applying an outward orthogonal force to the coupled wheel and moveable housing ring; and drawing fluid from a reservoir based on the outward movement of the coupled wheel and moveable housing ring.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An ophthalmic device, comprising:
   a housing;
   a cannula extending from the housing, the cannula having a lumen for fluid flow;
   a reservoir for holding fluid; and
   an activation assembly, comprising:
      a rotatable wheel; and
      a moveable housing ring coupled to the wheel, wherein the rotatable wheel and the moveable housing ring are configured to move inward together towards an interior of the housing when a first force is applied inward on the wheel and to move outward together away from the interior of the housing when a second force is applied outward on one of the wheel and the moveable housing ring.

2. The ophthalmic device of claim 1, further comprising a fixed housing ring fixedly coupled to the housing and moveably coupled to the moveable housing ring, wherein the moveable housing ring is configured to move inward and outward relative to the fixed housing ring.

3. The ophthalmic device of claim 1, wherein the housing comprises a fixed housing ring coupled to the moveable housing ring, wherein the moveable housing ring is configured to move inward and outward relative to the fixed housing ring.

4. The ophthalmic device of claim 1, wherein the rotatable wheel is configured to move a catheter through the cannula.

5. The ophthalmic device of claim 4, wherein the rotatable wheel is configured to move a wire through the catheter.

6. The ophthalmic device of claim 1, wherein the rotatable wheel is configured to move a wire through the cannula.

7. The ophthalmic device of claim 1, wherein the rotatable wheel is configured to move a tensioning device through the cannula.

8. The ophthalmic device of claim 1, wherein the rotatable wheel is configured to advance one of a catheter, a wire and a tensioning device when the rotatable wheel is rotated in a forward direction towards the cannula.

9. The ophthalmic device of claim 1, wherein the rotatable wheel is configured to retract one of a catheter, a wire and a tensioning device when the rotatable wheel is rotated in a rearward direction away from the cannula.

10. The ophthalmic device of claim 1, wherein the activation assembly is configured to pump fluid through the lumen of the cannula when the coupled rotatable wheel and moveable housing ring are moved inward.

11. The ophthalmic device of claim 1, wherein the activation assembly is configured to draw fluid from the fluid reservoir when the coupled rotatable wheel and moveable housing ring are moved outward.

12. The ophthalmic device of claim 1, further comprising a spring coupled to one of the rotatable wheel and the moveable housing ring, wherein the spring is biased to provide the second force.

13. The ophthalmic device of claim 1, wherein the housing comprises a tactile portion that is one of formed with the housing and disposed on the housing, the tactile portion configured to provide an ergonomic grip.

14. The ophthalmic device of claim 1, further comprising a catheter configured to slidably move through the cannula, the catheter comprising an internal lumen for fluid flow.

15. The ophthalmic device of claim 14, wherein a portion of the catheter comprises one or more side ports disposed in a wall of the catheter, the one or more side ports configured to provide fluid flow external to the catheter from the internal lumen.

16. The ophthalmic device of claim 15, wherein the catheter comprises one or more o-rings disposed around the catheter, the one or more o-rings configured to provide a constrained fluid zone external to the catheter.

17. The ophthalmic device of claim 14, wherein the catheter comprises a bulb disposed at a tip of the catheter, the bulb having a leading feature comprising one of a flat surface extending from the bulb and a pointed portion extending from the bulb.

18. The ophthalmic device of claim 14, wherein the catheter comprises a hole disposed at a tip of the catheter, the hole configured to provide one of
   fluid passage from the internal lumen;
   slidable movement of a suture disposed within the internal lumen; and
   slidable movement of a tensioning device disposed within the internal lumen.

19. The ophthalmic device of claim 14, wherein the catheter comprises an axial indentation disposed in an external surface of a catheter wall, the axial indentation configured to receive one of a suture and a tensioning device.

20. A method of operating an ophthalmic device, the method comprising:
   gripping a housing of the ophthalmic device;
   applying a rotational force to a wheel of an activation assembly of the ophthalmic device;

slidably moving one of a catheter, a wire and a tensioning device through a cannula of the ophthalmic device based on the rotational force;

applying an inward orthogonal force to the wheel;

moving the wheel and a moveable housing ring coupled to the wheel inward together towards an interior of the housing based on the inward orthogonal force;

pumping fluid through a lumen of the cannula based on the inward movement of the coupled wheel and moveable housing ring;

applying an outward orthogonal force to the coupled wheel and moveable housing ring; and drawing fluid from a reservoir based on the outward movement of the coupled wheel and moveable housing ring.

* * * * *